(12) United States Patent
Huang et al.

(10) Patent No.: US 10,267,775 B2
(45) Date of Patent: Apr. 23, 2019

(54) EXTRACTION, DERIVATIZATION, AND QUANTIFICATION OF ANALYTES

(71) Applicant: SPEware Corporation, Baldwin Park, CA (US)

(72) Inventors: Qi Huang, Camarillo, CA (US); Philip A. Dimson, San Pedro, CA (US); Karsten R. Liegmann, Altadena, CA (US)

(73) Assignee: TECAN SP, INC., Baldwin Park, CA (US)

( * ) Notice: Subject to any disclaimer, the term of this patent is extended or adjusted under 35 U.S.C. 154(b) by 234 days.

(21) Appl. No.: 14/726,530

(22) Filed: May 30, 2015

(65) Prior Publication Data

US 2015/0346170 A1 Dec. 3, 2015

Related U.S. Application Data

(60) Provisional application No. 62/005,676, filed on May 30, 2014.

(51) Int. Cl.
| | |
|---|---|
| *G01N 30/00* | (2006.01) |
| *G01N 30/72* | (2006.01) |
| *G01N 30/84* | (2006.01) |
| *H01J 49/00* | (2006.01) |
| *G01N 1/40* | (2006.01) |
| *G01N 30/02* | (2006.01) |
| *B01D 15/24* | (2006.01) |

(52) U.S. Cl.
CPC ......... *G01N 30/7233* (2013.01); *G01N 1/405* (2013.01); *G01N 30/84* (2013.01); *H01J 49/0031* (2013.01); *B01D 15/24* (2013.01); *G01N 30/72* (2013.01); *G01N 2030/027* (2013.01); *G01N 2030/8435* (2013.01); *Y10T 436/142222* (2015.01); *Y10T 436/173845* (2015.01); *Y10T 436/24* (2015.01)

(58) Field of Classification Search
CPC .................................................. G01N 30/7233
USPC ......................................................... 436/173
See application file for complete search history.

(56) References Cited

U.S. PATENT DOCUMENTS

2011/0033946 A1 2/2011 Berenson et al.
2011/0306144 A1 12/2011 Goldman et al.

OTHER PUBLICATIONS

A.M. Botero-Coy, M. Ibáanez, J.V. Sancho, F. Hernández "Improvements in the analytical methodology for the residue determination of the herbicide glyphosate in soils by liquid chromatography coupled to mass spectrometry" Journal of Chromatography A, 1292 (2013) 132-141.*

H. Bruckner, M. Lupke "Use of chromogenic and fluorescent oxycarbonyl chlorides as reagents for amino acid analysis by high-performance liquid chromatography" Journal of Chromatography A, 697 (1995) 295-307.*

(Continued)

*Primary Examiner* — Christine T Mui
*Assistant Examiner* — Emily R. Berkeley
(74) *Attorney, Agent, or Firm* — Entralta P.C.; Jeffrey M. McQuiston; Peter D. Weinstein

(57) ABSTRACT

The present specification discloses methods for determining the presence one or more analytes in a test sample, materials useful to perform the disclosed methods, and kits comprising reagents useful to practice the disclosed methods.

20 Claims, 19 Drawing Sheets

(56) References Cited

OTHER PUBLICATIONS

A. A. Descombes / W. Haerdi "HPLC Separation of Catecholamines after Derivatization with 9"Fluorenylmethyl Chloroformate" Chromatographia vol. 33, No. 1/2, Jan. 1992.*

José Maria Fernández-Molina, Manuel Silva "Improved solid-phase extraction/micellar procedure for the derivatization/preconcentration of benzaldehyde and methyl derivatives from water samples" Talanta 85 (2011) 449-454 (Year: 2011).*

Alexander Leitner, Peter Zoll''ner, Wolfgang Lindner "Determination of the metabolites of nitrofuran antibiotics in animal tissue by high-performance liquid chromatography—tandem mass spectrometry" Journal of Chromatography A, 939 (2001) 49-58 (Year: 2001).*

Pan et al. Journal of Food, Agriculture & Environment, vol. 11 Issue: 3 & 4, pt. 1, p. 115-118, 2013 (Year: 2013).*

Chan et al., High-performance liquid chromatographic assay for catecholamines and metanephrines using flurimetric detection with pre-column 9-fluorenylmethyloxycarbonyl chloride derivatization, Journal of Chromatography B, 749 (2000) 179-189.

International Search Report and Written Opinion, PCT/US2015/033437, dated Aug. 12, 2015.

\* cited by examiner

EXTRACTION, DERIVATIZATION, AND QUANTIFICATION OF ANALYTES

This application claims priority under 35 U.S.C. § 119(e) to U.S. Provisional Application 62/005,676 filed May 30, 2014, the entire contents of which are hereby expressly incorporated by reference.

There is a need to obtain fast, streamlined, and automated methods for detection of particular analytes. In the medical context, such methods would facilitate the detection of analytes, such as drugs, hormones, signaling agents, and amino acids. In the agricultural and public health context, the detection of residual levels of antibiotics, pesticides or other contaminants is integral to the safety of the food we eat and water we drink. Furthermore, recent changes in the standards for food labeling, such as "hormone free" or "organic" have created a need for streamlined testing in the agricultural realm.

Catecholamines are essential hormones or neurotransmitters that are important in maintaining a body's healthy conditions. Neurological disorders such as Parkinson's disease, or Alzheimer's disease often may alter the levels of these substances in the blood. Elevated levels of metanephrines (derivatives of catecholamines) may be indicative of onset of certain cancers such as pheochromocytoma. Similarly, metanephrines (metanephrine and normetanephrine), thyroid hormones (thyroxine T4, 3,5,5'-triiodothyronine T3, and 3,3',5-triiodothyronine rT3), estrogen hormones (estrone, esterol, estradiol, and estriol), delta-9-tetrahydrocannabinol (THC) its derivatives and metabolites, etc., are among many other biologically interesting molecular markers that are important for clinicians to determine the status of a patient.

Traditionally, clinical quantification of catecholamines were carried out via radio immunoassays (RIA). In recent years, due to the technology advancement in Mass Spectroscopy, there is a gradual shift in testing platform from RIA to liquid chromatography mass spectrometry (LCMS). Often times, the LCMS based assays provide a fast, sensitive, and analyte specific readout, which an RIA assay may lack. However, catecholamines are difficult to detect as they are prone to be oxidized and degraded. Further, the current art in catecholamines/metanephrine quantification often involves complex and cumbersome extraction procedures with unstable extraction recovery, thus giving rise to results which are often unreliable, and with high lower limits of quantification (LLOQ); for example an LLOQ in >10 ng/mL range. Also, the existing extraction process is unable to provide a reliable sample for derivatization.

Drugs include both illegal and legal drugs and metabolites or derivatives thereof. The detection of these compounds for forensic or prescription compliance are very important. Again, these drugs may not be stable in bodily fluids and therefore, detection may be difficult. In any event, there is a great need for a fully automated and simplified detection/quantification procedure which minimizes the room for human involvement or error.

SUMMARY

This invention document provides materials and methods that can be used measure the levels of catecholamines (Dopamine, epinephrine, norepinephrine), metanephrines (metanephrine and normetanephrine), thyroid hormones (T4, T3, and rT3), estrogen hormones (estrone, estradiol, estriol), cannabinoids such as Δ-9-tetrahydrocannabinol (THC), serotonin, amino acids, BPA, and many other primary and secondary amine containing, or phenol containing molecules in a biological sample. The desired analyte can be selectively and sensitively detected and measured by mass spectrometry, including tandem mass spectrometry technologies. The entire quantification process includes a sample preparation process that employs a solid phase extraction to capture the analyte, followed by a chemical derivatization of the analyte, then quantification via LC-MS/MS technologies, as described herein.

It was discovered during this work that the combination of solid phase extraction with a chemical derivatization with Fmoc chloride and LC-MS/MS provides analyte specific, sensitive, accurate, stable and robust measurements of levels of catecholamines at 10 pg/ml or lower in blood plasma/serum sample. Quantification methods for metanephrines and thyroid hormones were also developed with similar sensitivity and accuracy.

Sensitive and accurate measurements of these analytes at levels relevant to the clinical setting is useful, particularly at low pico-gram per milliliter range, at small sample size (100 uL or less of blood plasma/serum sample), with a simple process which can be easily configured to be automated, with an analyte specific results, without any analyte crossovers that are often seen under other analytical techniques such as radioimmunoassay (RIA).

DETAILED DESCRIPTION

Figure 1A:
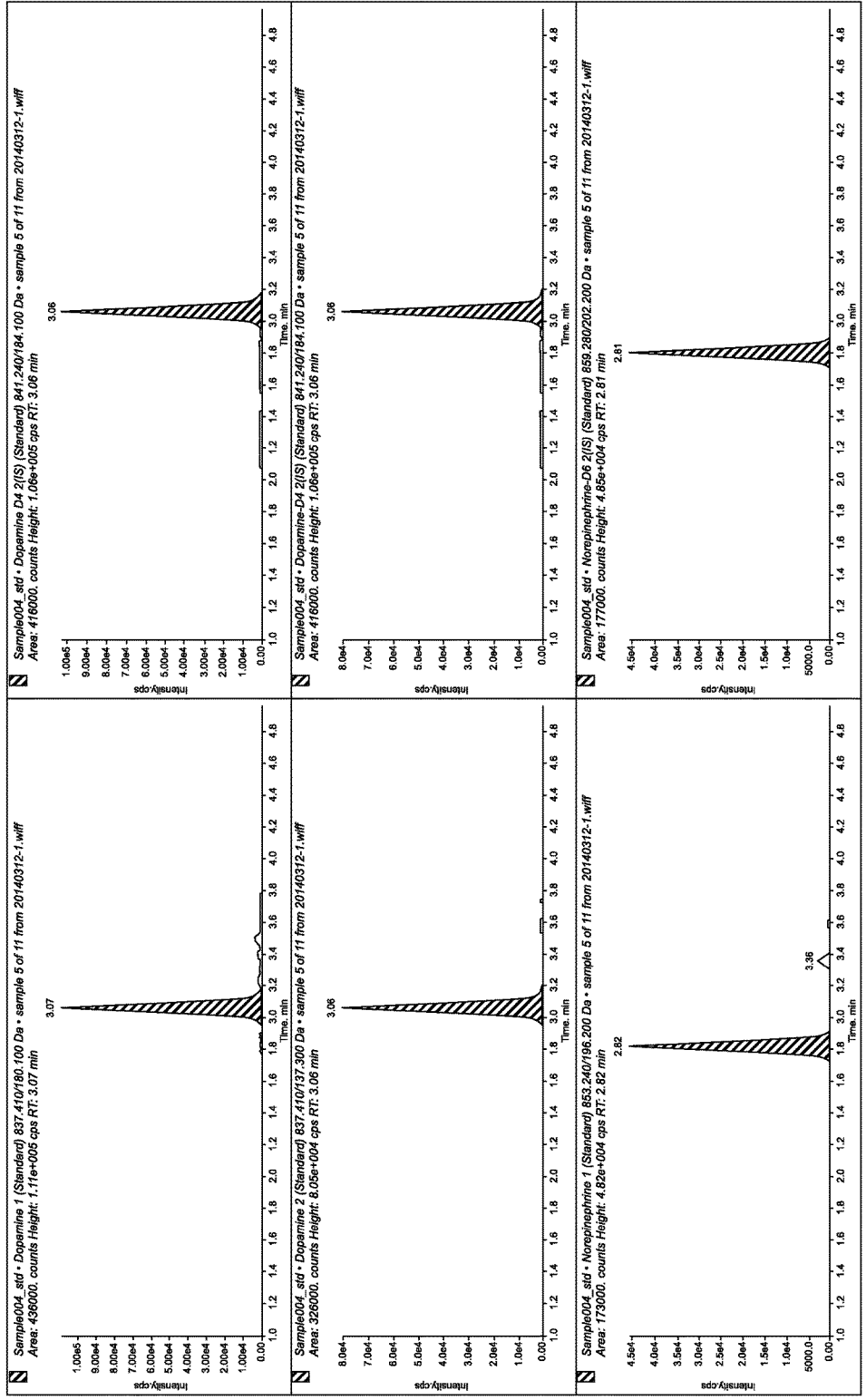
FIGS. 1A and 1B present example data showing the chromatograms for the internal standard equivalent 100 pg (FIG. 1A) and for the catecholamine spiked plasma (FIG. 1B).

The present methods are directed to methods of extraction, derivatization, and detection and/or quantification of analytes from a sample. The present methods employ a sample clean-up process via solid phase extraction (SPE), chemical derivatization process in conjunction with detection or quantification of analytes of interest to obtain analyte specific, robust, fast, sensitive, and accurate results. The derivatization of the analyte of interest shifts the analyte out of the region where it might potentially overlap with other biological agents found in the sample. Thus, during detection, other biological molecules or contaminants which would ordinarily interfere with the accurate quantification of the analyte of interest are detected at a significantly different range of the spectrum (or eluted completely), allowing the accurate quantification of the analyte of interest. Such analyte detection is useful, e.g., in a clinical, a veterinarian, a forensic, and/or an environmental setting.

The present methods may include derivatization of the analytes of interest, and determination of the amount of one or more of the analytes by at least one of chromatography and/or mass spectrometry. In one embodiment, the present methods may also include a solid phase extraction (SPE) of the analyte from a biological sample. In one aspect, it is recommended that cation exchange based SPE may be used for capture amine containing analytes. For non-amine containing analytes, a reverse phase silica sorbent based SPE may be employed with a protein crash with or without a phospholipid removal process, where such sorbent may be C4-C18 alkyl bounded silica, or phenyl bounded silica, or biphenyl bonded silica. In other embodiments the final elution buffer with high pH (8≤pH≤14) may be used to elute the amine containing analyte(s) from the cation exchange solid phase and optionally in situ derivatization of the amine containing analyte(s) of interest, cleanly preparing the derivative of the analyte for detection and/or quantification.

In additional embodiments, the non-amine containing analytes may be elute off from the SPE sorbent via a non-alcoholic, water miscible, organic solvent, such as acetonitrile, DMF, acetone, 1,4-dioxane, THF, NMP, DMSO, and etc., followed by direct derivatization of the analyte under a pH buffered condition. In a preferred embodiment, the present methods for detection of an amine containing analyte include cation exchange SPE, high pH elution of amine analyte from cation exchange sorbent, direct quantification via LC-MS/MS or in situ derivatization, and then quantification via LC-MS of the analyte of interest; permitting inline transitioning from biological sample to initial analyte extraction to detection and/or quantification. Similarly, for the preferred embodiment for detection of a non-amine containing analyte, present methods include reverse phase based SPE, organic elution followed by direct derivatization under high pH buffer conditions, then completed by LC-MS/MS quantification. Or in another embodiment, an anion exchange based SPE may be used for detection of an analyte with a carboxylic function group, with a high pH elution buffer mixed with suitable organic solvents such as acetonitrile, DMF, acetone, 1,4-dioxane, THF, NMP, DMSO, and etc., followed by direct derivatization of the analyte under a pH buffered condition.

Also presented are kits for a detection and/or quantification assay. Such kits may include SPE columns (cartridges) and a derivatization reagent. Optionally, such kits may also include a SPE conditioning solvent, loading buffer, washing buffer, and an eluent buffer, separately or together, and an HPLC column.

The present methods may detect the presence of a wide array of analytes. An analyte is any compound or composition of interest to be found in the sample of interest. More specifically, an analyte of interest is a compound having primary and or secondary amine groups, and or, a phenolic moiety. An analyte as disclosed herein may be a drug (illegal and FDA approved) and a derivative or a metabolite thereof, a pesticide and a derivative or metabolite thereof, an environmental contaminant and a derivative or metabolite thereof, or a biologic compound such as, e.g., a hormone, a cytokine, a signaling agent, an amino acid, cholesterol or one of its derivatives, a fatty acid or a glycolipid, and a derivative or metabolite thereof.

In one embodiment, an analyte is a monoamine neurotransmitter, or one of its derivatives or metabolites. Examples of monoamines include catecholamines [Dopamine (DA), Epinephrine (EP), Norepinephrine (NEP)], or its derivatives or metabolites: metanephrines [Metanephrine (MNE), Normetanephrine (NMN)], other trace amines 3-Methoxytyramine (3-MT), p-Octopamine, Synephrine, Tyramine, 3,4-dihydroxybenzylamine, 3,4-Dihydroxymandelic acid, Dihydroxyphenylethylene glycol, DOPAL, DOPAC, Homovanillic acid, Hydroxytyrosol, 3-Methoxy-4-hydroxyphenylglycol, MOPET, or Normetanephrine, Vanillylmandelic acid, Catechol, Dopa, histamine, serotonin (5-HT), 3-iodothyronamine, beta-phenethylamine, N-methylphenethylamine, tryptamine, N-methyltryptamine.

In another embodiment, an analyte is an estrogen including Estrone (E1), Estradiol (E2), Estriol (E3), and Estetrol (E4).

In another embodiment, an analyte is a phytoestrogen, including daidzein, formononetin, genistein, biochanin A, coumestrol, 4'-methoxycoumestrol, repensol, trifoliol, or 17-beta-estradiol.

In another embodiment, an analyte is a cannabinoid or one of its derivatives or metabolites. Examples of cannabinoids or one of its derivatives or metabolites include a Cannabigerol-type (CBG) cannabinoid such as, e.g., Cannabigerol, Cannabigerol monomethyl ether, Cannabinerolic acid A, Cannabigerovarin, Cannabigerolic acid A, Cannabigerolic acid A monomethyl ether, and Cannabigerovarinic acid A; a Cannabichromene-type (CBC) cannabinoid, such as, e.g., (±)-Cannabichromene, (±)-Cannabichromenic acid A, (±)-Cannabivarichromene, (±)-Cannabichromevarin, or (±)-Cannabichromevarinic acid A; a Cannabidiol-type (CBD) cannabinoid such as, e.g., (−)-Cannabidiol, Cannabidiol momomethyl ether, Cannabidiol-C4, (−)-Cannabidivarin, Cannabidiorcol, Cannabidiolic acid, Cannabidivarinic acid; a Cannabinodiol-type (CBND) cannabinoid such as, e.g., Cannabinodiol or Cannabinodivarin; a Tetrahydrocannabinol-type (THC) cannabinoid such as, e.g., Δ9-Tetrahydrocannabinol, Δ9-Tetrahydrocannabinol-C4, Δ9-Tetrahydrocannabivarin, Δ9-Tetrahydrocannabiorcol, Δ9-Tetrahydrocannabinolic acid A, Δ9-Tetrahydro-cannabinolic acid B, Δ9-Tetrahydro-cannabinolic acid-C4 A, Δ9-Tetrahydro-cannabinolic acid-C4 B, Δ9-Tetrahydro-cannabivarinic acid A, Δ9-Tetrahydro-cannabiorcolic acid A, Δ9-Tetrahydro-cannabiorcolic acid B, (−)-Δ8-trans-(6aR,10aR)-Δ8-Tetrahydrocannabinol, (−)-Δ8-trans-(6aR,10aR)-Tetrahydrocannabinolic acid A, (−)-(6aS,10aR)-Δ9-Tetrahydrocannabinol; a Cannabinol-type (CBN) cannabinoid such as, e.g., Cannabinol, Cannabinol-C4, Cannabivarin, Cannabinol-C2, Cannabiorcol, Cannabinolic acid A, Cannabinol methyl ether; a Cannabitriol-type (CBT) cannabinoid such as, e.g., (−)-(9R,10R)-trans-Cannabitriol, (+)-(9S,10S)-Cannabitriol, (±)-(9R,10S/9S,10R)-Cannabitriol, (−)-(9R,10R)-trans-10-O-Ethyl-cannabitriol, (±)-(9R,10R/9S,10S)-Cannabitriol-C3, 8,9-Dihydroxy-Δ6a(10a)-tetrahydrocannabinol, Cannabidiolic acid A cannabitriol ester, (−)-(6aR,9S,10S,10aR)-9,10-Dihydroxy-hexahydrocannabinol, (−)-6a,7,10a-Trihydroxy-Δ9-tetrahydrocannabinol, 10-Oxo-Δ6a(10a)-tetrahydrocannabinol; a Cannabielsoin-type (CBE) cannabinoid such as, e.g., (5aS,6S,9R,9aR)-Cannabielsoin, (5aS,6S,9R,9aR)-C3-Cannabielsoin, (5aS,6S,9R,9aR)-Cannabielsoic acid A, (5aS,6S,9R,9aR)-Cannabielsoic acid B, (5aS,6S,9R,9aR)-C3-Cannabielsoic acid B, Cannabiglendol-C3, Dehydrocannabifuran, or Cannabifuran; an Isocannabinoid such as, e.g., (−)-Δ7-trans-(1R,3R,6R)-Isotetrahydrocannabinol, (±)-Δ7-1,2-cis-(1R,3R,6S/1S,3S,6R)-Isotetrahydrocannabivarin, or (−)-Δ7-trans-(1R,3R,6R)-Isotetrahydrocannabivarin; a Cannabicyclol-type (CBL) cannabinoid such as, e.g., (±)-(1aS,3aR,8bR,8cR)-Cannabicyclol, (±)-(1aS,3aR,8bR,8cR)-Cannabicyclolic acid A, or (±)-(1aS,3aR,8bR,8cR)-Cannabicyclovarin; a Cannabicitran-type (CBT) cannabinoid such as, e.g., Cannabicitran; and a Cannabichromanone-type (CBCN) cannabinoid such as, e.g., Cannabichromanone, Cannabichromanone-C3, or Cannabicoumaronone.

In another embodiment, an analyte is a thyroid hormone or one of its derivatives or metabolites. Examples of thyroid hormones or one of its derivatives or metabolites include 3,3',5-triiodothyronine (T3), 3,5,5'-triiodothyronine (rT3), and thyroxine (T4).

In another embodiment, an analyte is an opiate, opioid or one of its derivatives or metabolites. Examples, of opiates or opioids or one of its derivatives or metabolites include the naturally-occurring benzylisoquinoline alkaloids (morphine, and oripavine), the semi-synthetic derivatives (hydromorphone, and oxymorphone), and the synthetic opioids (e.g., buprenorphine, etorphine, pentazocine).

In another embodiment, an analyte is arylcyclohexylamine or one of its derivatives or metabolites. Examples of an arylcyclohexylamine include Tiletamine, 3-Methoxetamine (MXE), Methoxyketamine, N-ethylnorletamine (Ethketamine)

In another embodiment, an analyte is an Amphetamine. Examples of Amphetamines are Amphetamine (itself), methamphetamine, ephedrine, cathinone, 3,4-methylenedioxy-N-methylamphetamine (MDMA, "Ecstasy"), and 2,5-Dimethoxy-4-methylamphetamine (DOM, or "STP").

In another embodiment, an analyte is an amino acid, an artificial amino acid, or a small peptide. Examples of the amino acid include but are not limited to: glycine, alanine, phenylalanine, tyrosine, GABA, tryptophan, cysteine, serine, valine, leucine, isoleucine, lysine, methionine, histidine, arginine, aspartic acid, asparagine, glutamic acid, glutamine, proline, and threonine.

In another embodiment, an analyte is bisphenol A (BPA).

Aspects of the present specification disclose, in part, a test sample. A test sample refers to any sample that may contain an analyte of interest. A test sample may be a biological sample, that is, a sample obtained from any biological source, such as an animal, a plant, a fungus, a microorganism, a cell culture, an organ culture, etc. In aspects of this embodiment, a biological sample includes a blood sample including a whole blood sample, a dry blood sample, a plasma sample, or a serum sample, a saliva sample, a lachrymal sample, a semen sample, a urine sample, cerebrospinal fluid sample, a bile sample, an embryonic fluid sample, a tissue sample, or any other sample that can be obtained, extracted or isolated from a biological source. Such biological samples may be obtained, for example in a medical or clinical setting, from a patient; that is, a living person, male or female, presenting oneself in a clinical setting for diagnosis, prognosis, or treatment of a disease or condition. The sample is preferably obtained from a patient, for example, a plasma specimen. The plasma specimen may be taken with or without the use of anticoagulants.

Such biological samples may be obtained, for example in a veterinarian setting, from an animal; that is, a pet animal, or a farm animal or livestock, a fish, or any other creatures that live in fresh water, ocean or sea, male or female, presenting oneself in a veterinarian setting for diagnosis, prognosis, prevention, or treatment of a disease or condition. The sample is preferably obtained from an animal, for example, a plasma specimen. The plasma specimen may be taken with or without the use of anticoagulants.

A test sample may be obtained from a plant or any vegetation source, in agricultural or environmental setting, from a leaf, or a flower, or a stem, or a fruit, or a seed, or sprout, or a bark, or a root, etc.

A test sample may be obtained from a dead human body, or a dead animal, or a dead plant, or remains of a once living body, as in a forensic setting, or in an agricultural setting, or in an environmental setting, or in an archeological setting. A testing sample may be a blood sample, or a dry blood sample, or any other body fluid sample, or any other dry body fluid sample, or a body tissue sample taken from anywhere of the body or remains of a dead human, animal, or plant.

A test sample may be an environmental sample. Environmental samples are samples taken from dirt, plant matter, or fluid sources (such as ground water, oceans, or rivers etc.). Dirt (aka "soil samples") may be taken from agricultural sites or sites of environmental interest and may have the analyte extracted, including the removal of particulate matter.

Samples may be obtained by any known means. The sample may be preserved or pre-treated to ensure stability of the analyte of interest. Such preservation may be accomplished by chemical (such as hydrolysis or pH adjustment) or physical processes (such as refrigeration or freezing). When a sample is a solid or a tissue, it can be grounded, or extracted, or purified, or filtered, or centrifuged, to isolate the analyte of interest from the interfering components. Or a sample is a liquid, preferably, it is dissolved, or suspended, in a solution (or "loading buffer") having a pH range from weakly basic to neutral to weakly acidic; for example having a pH ranging from 10-3, or more preferably 9-4, or more preferably 8-5, or even more preferably 7-6, depending on the analyte of interest and the sorbent chemistry.

Any sample volume may be obtained as long as it is of sufficient volume to be useful in the methods disclosed herein. In aspects of this embodiment, a sample volume may be e.g., about 10 μL, about 25 μL, about 50 μL, about 75 μL, about 100 μL, about 125 μL, about 150 μL, about 175 μL, about 200 μL, about 225 μL, about 250 μL, about 275 μL, about 300 μL, about 325 μL, about 350 μL, about 375 μL, about 400 μL, about 425 μL, about 450 μL, about 475 μL, or about 500 μL. In other aspects of this embodiment, a sample volume may be e.g., at least 10 μL, at least 25 μL, at least 50 μL, at least 75 μL, at least 100 μL, at least 125 μL, at least 150 μL, at least 175 μL, at least 200 μL, at least 225 μL, at least 250 μL, at least 275 μL, at least 300 μL, at least 325 μL, at least 350 μL, at least 375 μL, at least 400 μL, at least 425 μL, at least 450 μL, at least 475 μL, or at least 500 μL. In yet other aspects of this embodiment, a sample volume may be e.g., at most 10 μL, at most 25 μL, at most 50 μL, at most 75 μL, at most 100 μL, at most 125 μL, at most 150 μL, at most 175 μL, at most 200 μL, at most 225 μL, at most 250 μL, at most 275 μL, at most 300 μL, at most 325 μL, at most 350 μL, at most 375 μL, at most 400 μL, at most 425 μL, at most 450 μL, at most 475 μL, or at most 500 μL. In still other aspects of this embodiment, a sample volume may be between e.g., about 10 μL and about at most 100 μL, about 10 μL and about at most 200 μL, about 10 μL and about at most 300 μL, about 10 μL and about at most 400 μL, about 10 μL and about at most 500 μL, about 10 μL and about at most 600 μL, about 10 μL and about at most 700 μL, about 10 μL and about at most 800 μL, about 10 μL and about at most 900 μL, about 10 μL and about at most 1000 μL, about 50 μL and about at most 100 μL, about 50 μL and about at most 200 µL, about 50 µL and about at most 300 µL, about 50 µL and about at most 400 µL, about 50 µL and about at most 500 µL, about 50 µL and about at most 600 µL, about 50 µL and about at most 700 µL, about 50 µL and about at most 800 µL, about 50 µL and about at most 900 µL, about 50 µL and about at most 1000 µL, about 100 µL and about at most 200 µL, about 100 µL and about at most 300 µL, about 100 µL and about at most 400 µL, about 100 µL and about at most 500 µL, about 100 µL and about at most 600 µL, about 100 µL and about at most 700 µL, about 100 µL and about at most 800 µL, about 100 µL and about at most 900 µL, or about 100 µL and about at most 1000 µL.

A test sample disclosed herein may be purified. As used herein, the terms "purified", "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions of the selected analyte by mass spectrometry. Relative reduction as this term is used does not require that any substance, present with the analyte of interest in the material to be purified, is entirely removed by purification. When detecting some analytes (particularly drugs) in a urine sample, hydrolysis may be necessary to remove the glucoronide bonding which prevents the solubility and extraction of the analyte. This purification technique is usually performed by enzyme or acid hydrolysis of the urine. Alternatively, removing particulate matter (e.g., by centrifugation or filtration), protein precipitation (optionally by a "protein crash" method) with or without phospholipid removal, may be useful purification techniques.

Purification may also be performed to create or make available reactive amino or phenolic groups, suitable for the derivatization reaction. These methods include hydrolysis of esters or amines, or acid hydrolysis of sugars.

Such purification by pre-processing is not limited, but serves to prepare the sample for solid phase extraction.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis.

SPE using an ion exchange extraction procedure is applied to extract the analytes of interest from the sample. Such analyte can be ionized under certain ranges of pH of a buffer. SPE may be performed with a range of characteristics suitable depending on the analyte. Analytes such as monoamine neurotransmitters, or catecholamines, or metanephrines, or amino acids, or thyroid hormones, or carboxylic acids, maybe extracted, or retained, or purified, via ion exchange extraction based SPE. More specifically strong to weak cation exchange may be used. SPE using a cation exchange is one example applied in the present methods of extracting analyte of interest from a blood plasma sample. Weak cation exchange cartridges with a divinylbenzene- (DVB-) based polymer sorbent are particularly exemplified for the SPE of catecholamines and metanephrines. SPE using a strong cation exchange extraction based SPE may also be used to purify catecholamines and metanephrines from the blood plasma sample with an SPE cartridge filled with a DVB-based polymer sorbent via stronger elution solvent. Moreover, silica based carboxylic acid sorbents may also be useful to extract catecholamines and metanephrines from the plasma samples.

A strong cation exchange (sulfonic acid chemistry) sorbent either based on silica or one or more polymers may also be useful to extract catecholamines and metanephrines in the SPE process. SPE with a strong cation exchange sorbent are particularly exemplified for the SPE of thyroid hormones (T3/rT3/T4). An amino acid analyte may be similarly extracted with a strong cation exchange sorbent, either polymer based, or silica based.

An anion exchange polymer may also be used to extract a carboxylic acid analyte, or an amino acid analyte, or a sulfonic acid analyte, or a phosphonic acid analyte.

Particular columns of interest for use in the present methods to extract catecholamines and metanephrines include the CEREX® PWCX, 1 mL Columns, 10 mg, 96/Pk (catalog number 6750-0101R. For thyroid hormones the CEREX® PSCX, 1 mL Columns, 10 mg, 96/Pk (catalog number 687-0101R) are suitable.

In yet another embodiment, a reverse phase silica based SPE column or cartridge may be used to extract, or purify, or retain the analyte of choice when the analyte does not have an amino group, such as estrogen hormones, or cannabinoids, or flavonoids. The sorbent of choice during this SPE/purification may include alkyl bounded silica (C4, C8, C12, and C18), cyano bounded silica, phenyl bounded silica, or biphenyl bounded silica.

Sizes of the columns may range, but in particular, a column volume may preferably range from 50 µL to 3000 µL, with a sorbent loading between 100 µg to 50 mg. In another embodiment, the more preferred column size ranges from 100 µL to 2000 µL with a sorbent loading between 1 mg to 20 mg. In another embodiment, the more preferred column size ranges from 200 µL to 1000 µL with a sorbent loading between 2 mg to 10 mg. Shape and size of the SPE columns (cartridges) may be varied to fit a specific platform.

The particle size of the sorbent may further assist in the separation of the analyte of interest. In aspects of this embodiment, a particle size of a sorbent may have a mean diameter of, e.g., about 0.5 µm, about 1 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, or about 75 µm. In other aspects of this embodiment, a particle size of a sorbent may have a mean diameter of, e.g., at least 0.5 µm, at least 1 µm, at least 5 µm, at least 10 µm, at least 15 µm, at least 20 µm, at least 25 µm, at least 30 µm, at least 35 µm, at least 40 µm, at least 45 µm, at least 50 µm, at least 55 µm, at least 60 µm, at least 65 µm, at least 70 µm, or at least 75 µm. In yet other aspects of this embodiment, a particle size of a sorbent may have a mean diameter of, e.g., at most 0.5 µm, at most 1 µm, at most 5 µm, at most 10 µm, at most 15 µm, at most 20 µm, at most 25 µm, at most 30 µm, at most 35 µm, at most 40 µm, at most 45 µm, at most 50 µm, at most 55 µm, at most 60 µm, at most 65 µm, at most 70 µm, or at most 75 µm. In still other aspects of this embodiment, a particle size of a sorbent may have a mean diameter in the range of, e.g., about 0.5 μm to about 10 μm, about 0.5 μm to about 20 μm, about 0.5 μm to about 30 μm, about 0.5 μm to about 40 μm, about 0.5 μm to about 50 μm, about 0.5 μm to about 60 μm, about 0.5 μm to about 70 μm, about 0.5 μm to about 80 μm, about 1 μm to about 10 μm, about 1 μm to about 20 μm, about 1 μm to about 30 μm, about 1 μm to about 40 μm, about 1 μm to about 50 μm, about 1 μm to about 60 μm, about 1 μm to about 70 μm, about 1 μm to about 80 μm, about 5 μm to about 10 μm, about 5 μm to about 20 μm, about 5 μm to about 30 μm, about 5 μm to about 40 μm, about 5 μm to about 50 μm, about 5 μm to about 60 μm, about 5 μm to about 70 μm, about 5 μm to about 80 μm, about 10 μm to about 20 μm, about 10 μm to about 30 μm, about 10 μm to about 40 μm, about 10 μm to about 50 μm, about 10 μm to about 60 μm, about 10 μm to about 70 μm, or about 10 μm to about 80 μm.

A sample may be loaded on the SPE column with a loading solvent, or a loading buffer. The loading solvent may be deionized water, or a pH buffered aqueous solution, or an organic solvent, or a mixture of organic solvents, or a mixture of an organic solvent and deionized water, or a mixture of organic solvents with deionized water, or a pH buffered aqueous solution mixed with an organic solvent or a mixture of organic solvents. The pH buffered aqueous solution may be a phosphate buffered saline (PBS), or a phosphate buffer, or a carbonate buffer, or a succinate buffer, or a tartrate buffer, or a citric buffer, or a formic buffer, or an acetic buffer, or another commonly used buffer solution in a typical biochemical lab, or a mixture of any of the two, or more of the following, a phosphate buffer, or a carbonate buffer, or an acetic buffer, or a formic buffer, or a citric buffer, or a succinate buffer, or a tartrate buffer, or, with a pH range from weakly basic to neutral to weakly acidic; for example having a pH ranging from 10-3, or more preferably 9-4, or more preferably 8-5, or even more preferably 7-6, at a concentration range from 0.1 mM to 100 mM, or more preferably 0.5 mM to 50 mM, or more preferably 1 mM to 25 mM, or more preferably 5 mM to 10 mM. An organic solvent may be selected from acetonitrile, or acetone, or 1,4-dioxane, or DMF, or tetrahydrofuran (THF), or diethylether, or ethyl acetate, or methyl acetate, or ethyl formate, methyl formate, or a mixture of thereof.

Upon loading the sample to the SPE column, the fluid is allowed to pass through the sorbent, via gravity, or a vacuum pulling through a vacuum manifold, or a nitrogen or inert gas pressure push through a positive pressure manifold, with or without an air drying process. The sample loaded cartridge may be further washed with a solvent. The selection of the washing solvent may be deionized water, or a pH buffered aqueous solution, or organic solvent, or a mixture of organic solvents, or a mixture of organic solvents with an aqueous buffer. An organic solvent may be acetonitrile, or methanol, or ethanol, or isopropanol, or butanol, or diethyl ether, or acetone, or 1,4-dioxane, or THF, or DMF, ethyl acetate, or methyl acetate, or ethyl formate, methyl formate, or a mixture of any of the above solvents.

Upon loading and washing, the loaded cartridge may be treated with an elution fluid directly, or dried first via a stream of, dry nitrogen, or another dry inner gas, passing through the cartridge.

Aspects of the present specification disclose, in part, a method of in situ derivatization of the analyte of interest using a derivatizing agent. The analyte of interest reacts with a derivatizing reagent to provide a derivative of the analyte. This derivative displays an improved HPLC behavior, and significantly improved tandem MS/MS sensitivity. For instance the present method unexpectedly provides nearly, or over 1000-fold improvement in detection limitation and/or quantification sensitivity when quantifying catecholamines, metanephrines, thyroid hormone T3, rT3, and T4, from blood serum samples, by using LC-tandem MS/MS technologies.

A derivatizing reagent disclosed herein is a compound that can react with a primary or secondary amino, and/or a phenolic hydroxy group, and/or a primary alcohol (hydroxyl) group, and/or an aryl or alkyl thiol group, present in an analyte disclosed herein. Derivatizing agents of interest include, without limitation, an acylating agent, as in Formula I. Acylating reagents may include acyl chlorides or other acyl halides. Derivatizing agents may also fluoresce or participate in a colorimetric reaction to assist with the detection of the bound analyte.

(I)

In one embodiment, the derivatization is performed using FMoc chloride and variants thereof. The word "variants" is applied here to distinguish variations of FMoc chloride, examples thereof are partially represented in the Formula II. It is to be understood that a variety of variants of FMoc chloride are suitable for derivatization of the analyte according to the present methods. Thus, the specific embodiments discussed below are not an exclusive listing.

In one embodiment, the present methods employ a FMoc Chloride of Formula II:

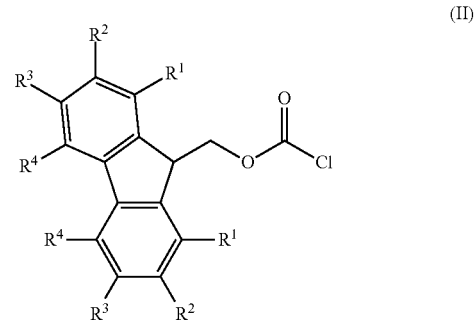
(II)

wherein each $R^1$, $R^2$, $R^3$, and $R^4$ are each independently H, a halogen atom such as a fluorine, or a chlorine, or a bromine, or an iodine, a cyano group, an acetylene group, a propylene group, a vinyl group, low alkyl (linear, branched, or cyclic C1-8 alkyl), a substituted vinyl group, a linear or branched or cyclic C1-8 alkoxy group. Examples of a linear or branched $C_{1-8}$ alkyl include, e.g., methyl, ethyl, propyl, butyl, cyclic propyl, cyclic pentyl, hexane, heptyl, and octyl etc.

In aspects of this embodiment, and FMOC chloride compound is:

Scheme 1

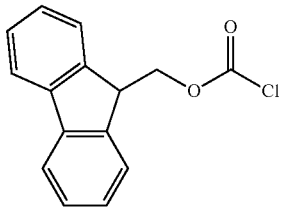

Chloroformic acid 9H-fluoren-9-ylmethyl ester

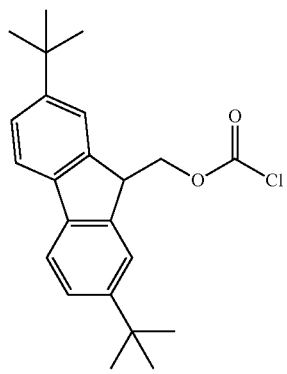

(2,7-di-tert-butyl-9H-fluoren-9-yl)
methyl carbonochloridate

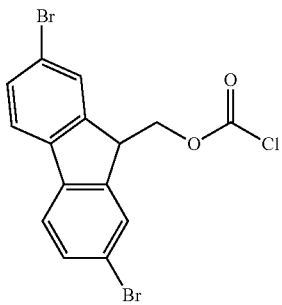

(2,7-dibromo-9H-fluoren-9-yl)
methyl carbonochloridate

Multiple variants of FMoc chloride such as represented above Scheme 1 may be used as a parallel derivatization reagent panel, to provide opportunities for simultaneously quantifying multiple samples in one LCMS run.

In another embodiment, the derivatizing reagent may be benzyl carbonyl chloride (CBZ chloride), or a variant thereof (Scheme 2). A variant is a CBZ chloride with substitutions on the phenyl ring, or a substituted CBZ chloride with a fused ring system, wherein each $R^1$, $R^2$, $R^3$, $R^4$, $R^5$, $R^6$, and $R^7$ are each independently H, a halogen atom such as a fluorine, or a chlorine, or a bromine, or an iodine, a cyano group, an acetylene group, a propylene group, a vinyl group, low alkyl (linear or branched or cyclic $C_{1-8}$ alkyl), a substituted vinyl group, a linear or branched or cyclic $C_{1-8}$ alkyl group. Examples of a linear or branched $C_{1-8}$ alkyl include, e.g., methyl, ethyl, propyl, butyl, cyclic propyl, cyclic pentyl, hexane, heptyl, and octyl etc. The fused ring system may be an all carbocyclic or a heterocyclic aromatic system, such as a naphthalene, or a benzofuran, or an indole, with a 5-7 membered fused ring, or a nonaromatic all carbocyclic, or heterocyclic fused ring system such as 3,4-dihydro-1H-indene, or a 3,4,dihydro-2H-chromene, with a 4-8 membered fused ring. The fused ring may be substituted when appropriate with one or more of a halogen atom such as a fluorine, or a chlorine, or a bromine, or an iodine, a cyano group, an acetylene group, a propylene group, a vinyl group, low alkyl (linear or branched or cyclic $C_{1-8}$ alkyl), a substituted vinyl group, a linear or branched or cyclic $C_{1-8}$ alkoxy group. Examples of a linear or branched $C_{1-8}$ alkyl include, e.g., methyl, ethyl, propyl, butyl, cyclic propyl, cyclic pentyl, hexane, heptyl, and octyl etc.

Scheme 2

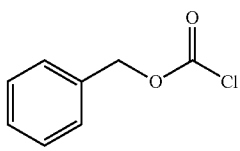

CBZ Chloride

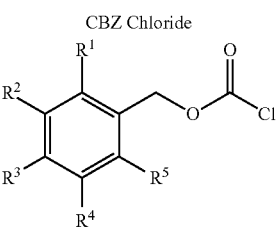

Substituted CBZ Chloride

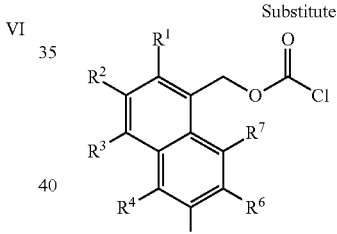

Substituted Fused Ring CBZ Chloride

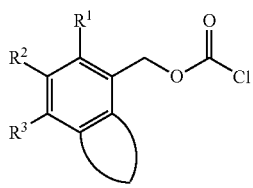

Substituted Fused Ring CBZ Chloride

In another embodiment, as shown in Scheme 3, the derivatization reagent may be a benzoyl chloride, or a variant thereof. A variant of benzoyl chloride is benzoyl chloride with substitutions on the phenyl ring, or a substituted benzoyl chloride with a fused ring system, wherein each $R^1$, $R^2$, $R^3$, $R^4$, $R^5$, $R^6$, and $R^7$ are each independently a Hydrogen, a halogen atom such as a fluorine, or a chlorine, or a bromine, or an iodine, a cyano group, an acetylene group, a propylene group, a vinyl group, low alkyl (linear or branched or cyclic $C_{1-6}$ alkyl), a substituted vinyl group, a linear or branched or cyclic $C_{1-8}$ alkyl group. Examples of a linear or branched $C_{1-8}$ alkyl include, e.g., methyl, ethyl, propyl, butyl, cyclic propyl, cyclic pentyl, hexane, heptyl, and octyl etc. The fused ring system may be an all carbocyclic or a heterocyclic aromatic system, such as a naphthalene, or a benzofuran, or an indole, with a 5-7 membered fused ring, or a nonaromatic all carbocyclic, or heterocyclic 4-8 membered fused ring system such as 3,4-dihydro-1H-indene, or a 3,4,dihydro-2H-chromene. The fused ring may be substituted when appropriate with one or more of a halogen atom such as a fluorine, or a chlorine, or a bromine, or an iodine, a cyano group, an acetylene group, a propylene group, a vinyl group, low alkyl (linear or branched or cyclic $C_{1-8}$ alkyl), a substituted vinyl group, a linear or branched or cyclic $C_{1-8}$ alkyl group. Examples of a linear or branched $C_{1-8}$ alkyl include, e.g., methyl, ethyl, propyl, butyl, cyclic propyl, cyclic pentyl, hexane, heptyl, and octyl etc.

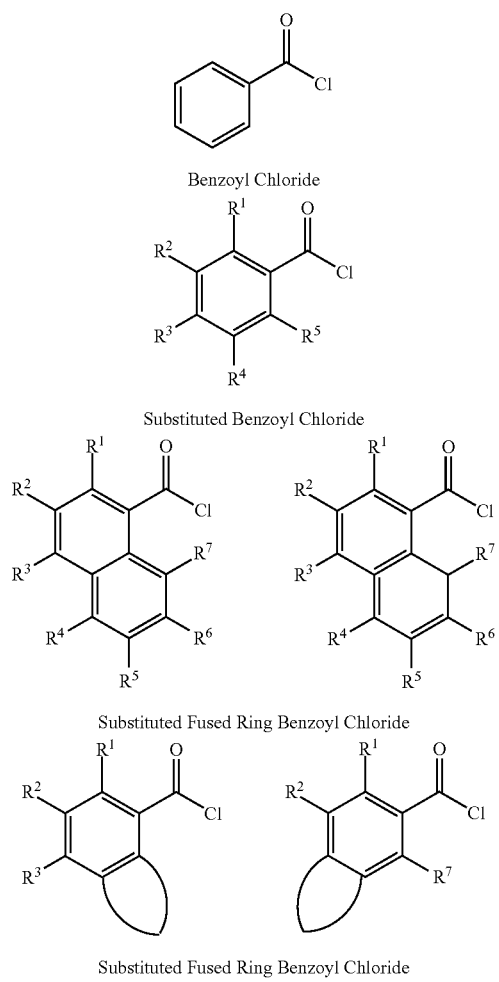

alkyl group. Examples of a linear or branched $C_{1-8}$ alkyl include, e.g., methyl, ethyl, propyl, butyl, cyclic propyl, cyclic pentyl, hexane, heptyl, and octyl etc. In a fused ring system, the system may be an all carbocyclic or heterocyclic aromatic system, such as a naphthalene, or a benzofuran, or an indole, with a fused ring sized from 5-7 membered, or a nonaromatic all carbocyclic, or heterocyclic fused ring system such as 3,4-dihydro-1H-indene, or a 3,4,dihydro-2H-chromene, with a fused ring sized from 4-8 membered. The fused ring may be substituted when appropriate one or more of a halogen atom such as a fluorine, or a chlorine, or a bromine, or an iodine, a cyano group, an acetylene group, a propylene group, a vinyl group, low alkyl (linear or branched or cyclic $C_{1-8}$ alkyl), a substituted vinyl group, a linear or branched or cyclic $C_{1-8}$ alkyl group. Examples of a linear or branched $C_{1-8}$ alkyl include, e.g., methyl, ethyl, propyl, butyl, cyclic propyl, cyclic pentyl, hexane, heptyl, and octyl etc.

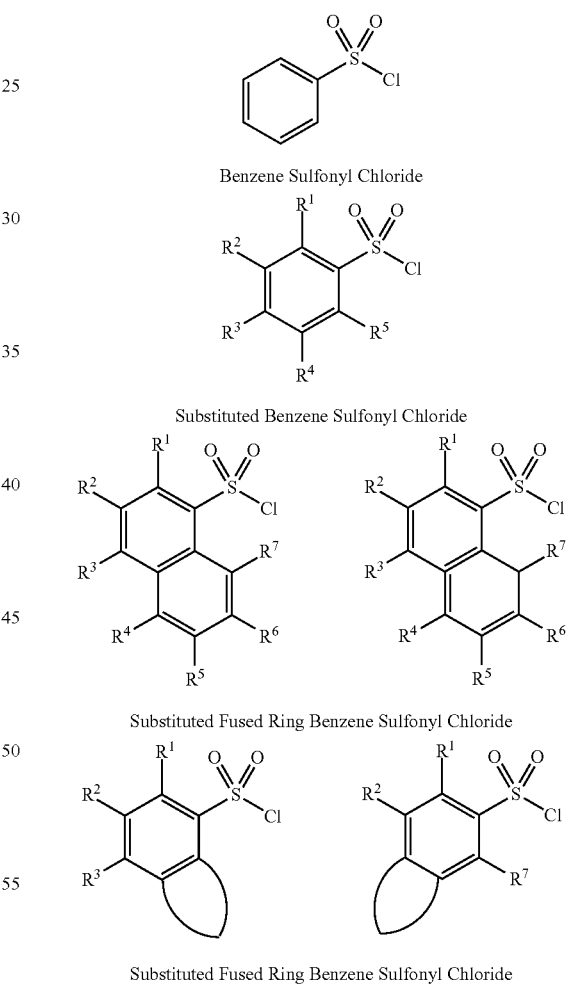

Another embodiment of the derivatization reagent as shown in Scheme 4 may be a benzenesulfonyl chloride, and a variant thereof. A variant of a benzenesulfonyl chloride may be a benzenesulfonyl chloride with substitutions on the benzene ring, or a substituted benzenesulfonyl chloride with a fused ring system, wherein $R^1$, $R^2$, $R^3$, $R^4$, $R^5$, $R^6$, and $R^7$ are each independently a Hydrogen, a halogen atom such as a fluorine, or a chlorine, or a bromine, or an iodine, a cyano group, an acetylene group, a propylene group, a vinyl group, low alkyl (linear or branched or cyclic $C_{1-8}$ alkyl), a substituted vinyl group, a linear or branched or cyclic C1-8

In another embodiment of the acylating reagent, it may be an acyl bromide, or an acyl fluoride, or a 4-nitrophenol ester, or a pentafluorophenol ester, or an acylimidazole, or a hydroxysuccimide ester (OSu), or a hydroxysuccimide sodium sulfonate ester (sulfo OSu), or a hydroxybenzotrizole ester (OBt), or a hydroxyl-aza-benzotriazole ester (OAt). The activated acyl reagents may be formed prior to the derivatization reaction, or may also be formed in situ during the derivatization reaction process via appropriate precursors and activation reagents that a skilled person will know. Acylating reagents provided in Scheme 5 are examples of the scope of the reagent, and not the limits to the scope.

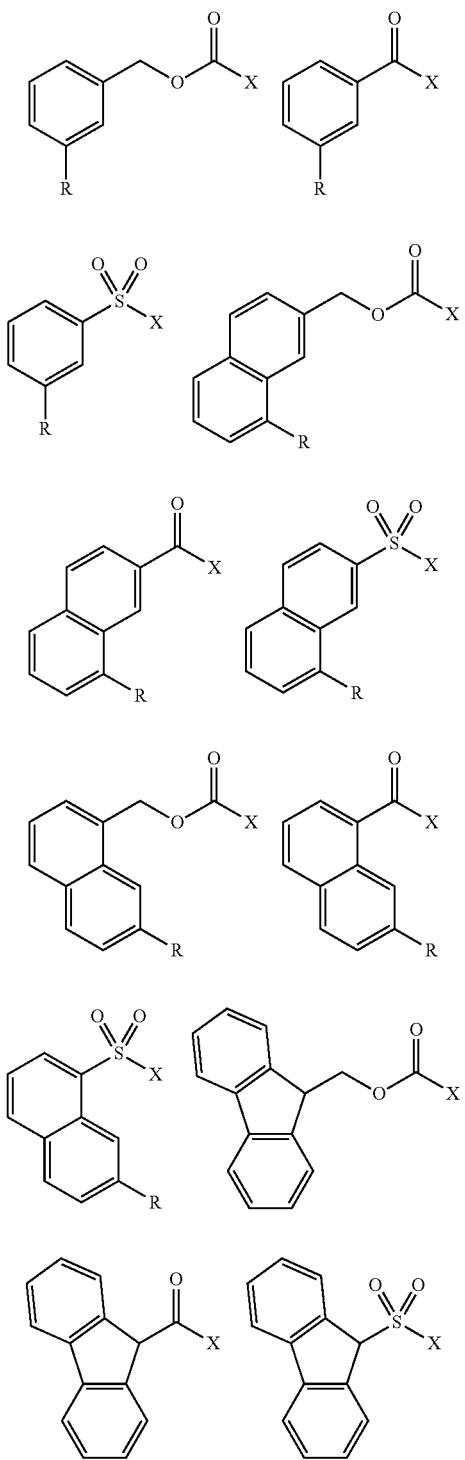

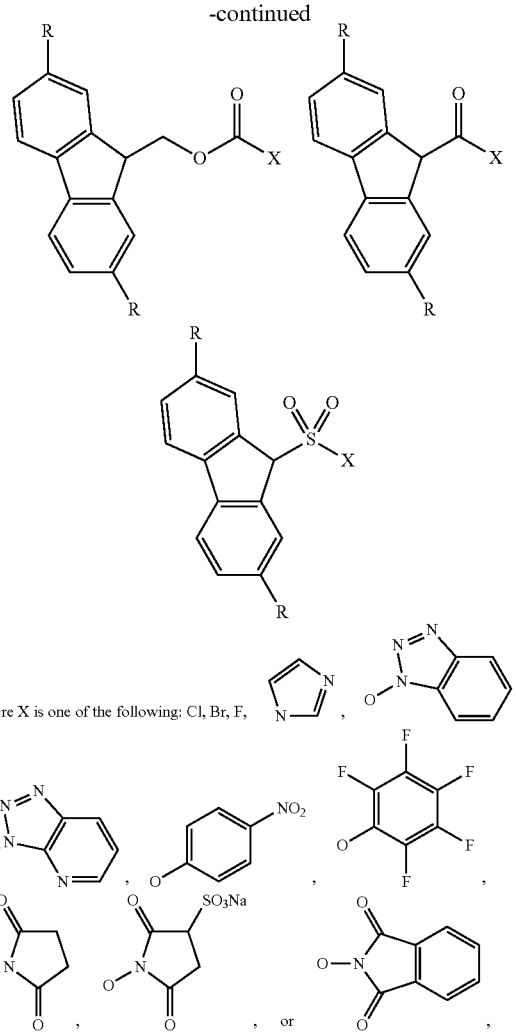

Such acylating reagents may be formed prior to the derivatization, may also be formed in situ during the derivatization process from appropriate precursors and coupling reagents.

Notably, multiple acylating reagents may be used in parallel fashion to derivatize the same analytes in multiple samples then combined into one LCMS quantification process, so called multiplex analysis, to significantly improve instrument operational efficiency and save solvents for LC. These acylating reagents may be from the same chemical class or from different chemical classes, as discussed above.

In situ derivatization is performed either just before elution, during elution, or right after elution, or from just before the elution continued until after the elution, from the solid phase extraction column. The elution is performed with a high pH elution solution. As used herein, "high pH" includes elution solutions having a basic pH. In an aspect of this embodiment, an elution solution may have a pH of, e.g., about 8, about 8.5, about 9, about 9.5, about 10, about 10.5, about 11, about 11.5, about 12, about 12.5, or about 13. In other aspect of this embodiment, an elution solution may have a pH of, e.g., at least 8, at least 8.5, at least 9, at least 9.5, at least 10, at least 10.5, at least 11, at least 11.5, at least 12, at least 12.5, or at least 13. In yet other aspect of this embodiment, an elution solution may have a pH of, e.g., at most 8, at most 8.5, at most 9, at most 9.5, at most 10, at most 10.5, at most 11, at most 11.5, at most 12, at most 12.5, or at most 13. In yet other aspect of this embodiment, an elution solution may have a pH in the range of, e.g., about 8 to about 9, about 8 to about 9.5, about 8 to about 10, about 8 to about 10.5, about 8 to about 11, about 8 to about 11.5, about 8 to about 12, about 8 to about 12.5, about 8 to about 13, about 8.5 to about 9, about 8.5 to about 9.5, about 8.5 to about 10, about 8.5 to about 10.5, about 8.5 to about 11, about 8.5 to about 11.5, about 8.5 to about 12, about 8.5 to about 12.5, about 8.5 to about 13, about 9 to about 9.5, about 9 to about 10, about 9 to about 10.5, about 9 to about 11, about 9 to about 11.5, about 9 to about 12, about 9 to about 12.5, about 9 to about 13, about 9.5 to about 10, about 9.5 to about 10.5, about 9.5 to about 11, about 9.5 to about 11.5, about 9.5 to about 12, about 9.5 to about 12.5, about 9.5 to about 13, about 10 to about 10.5, about 10 to about 11, about 10 to about 11.5, about 10 to about 12, about 10 to about 12.5, about 10 to about 13, about 10.5 to about 11, about 10.5 to about 11.5, about 10.5 to about 12, about 10.5 to about 12.5, about 10.5 to about 13, about 11 to about 11.5, about 11 to about 12, about 11 to about 12.5, or about 11 to about 13.

In another embodiment, the elution is performed with a lower pH elution solution. As used herein, "low pH" includes elution solutions having an acidic pH. In an aspect of this embodiment, an elution solution may have a pH of, e.g., about 2, about 2.5, about 3, about 3.5, about 4, about 4.5, about 5, about 5.5, about 6, or about 6.5. In other aspect of this embodiment, an elution solution may have a pH of, e.g., at least 2, at least 2.5, at least 3, at least 3.5, at least 4, at least 4.5, at least 5, at least 5.5, at least 6, or at least 6.5. In yet other aspect of this embodiment, an elution solution may have a pH of, e.g., at most 2, at most 2.5, at most 3, at most 3.5, at most 4, at most 4.5, at most 5, at most 5.5, at most 6, or at most 6.5. In yet other aspect of this embodiment, an elution solution may have a pH in the range of, e.g., about 2 to about 3, about 2 to about 3.5, about 2 to about 4, about 2 to about 4.5, about 2 to about 5, about 2 to about 5.5, about 2 to about 6, about 2 to about 6.5, about 2.5 to about 3, about 2.5 to about 3.5, about 2.5 to about 4, about 2.5 to about 4.5, about 2.5 to about 5, about 2.5 to about 5.5, about 2.5 to about 6, about 2.5 to about 6.5, about 3 to about 3.5, about 3 to about 4, about 3 to about 4.5, about 3 to about 5, about 3 to about 5.5, about 3 to about 6, about 3 to about 6.5, about 3.5 to about 4, about 3.5 to about 4.5, about 3.5 to about 5, about 3.5 to about 5.5, about 3.5 to about 6, about 3.5 to about 6.5, about 4 to about 4.5, about 4 to about 5, about 4 to about 5.5, about 4 to about 6, about 4 to about 6.5, about 4.5 to about 5, about 4.5 to about 5.5, about 4.5 to about 6, about 4.5 to about 6.5, about 5 to about 5.5, about 5 to about 6, about 5 to about 6.5, about 5.5 to about 6, about 5.5 to about 6.5, or about 6 to about 6.5.

In another embodiment, the elution is performed with a neutral pH elution solution. In an aspect of this embodiment, an elution solution may have a pH of, e.g., about 6.5, about 7, about 7.5 or about 8. In another aspect of this embodiment, an elution solution may have a pH of, e.g., at least 6.5, at least 7, at least 7.5 or at least 8. In yet another aspect of this embodiment, an elution solution may have a pH of, e.g., at most 6.5, at most 7, at most 7.5 or at most 8. In yet other aspect of this embodiment, an elution solution may have a pH in the range of, e.g., about 6.5 to about 7, about 6.5 to about 7.5, about 6.5 to about 8, about 7 to about 7.5, about 7 to about 8, or about 7.5 to about 8.

An elution solution disclosed herein may be buffered using any buffer having an alkaline buffering capacity. In aspects of this embodiment, an elution solution disclosed herein may be buffered using one or a mixture of the organic or inorganic buffering agents, e.g., POPSO, TEA, phosphate. In other aspects of this embodiment, an elution solution disclosed herein may be buffered using, e.g., a trialkylammonium buffer comprising, e.g., trialkylammonium bicarbonate, trialkylammonium borate, trialkylammonium carbonate, or a trialkylammonium phosphate; a cesium buffer comprising, e.g., cesium bicarbonate, cesium borate, cesium carbonate, cesium hydroxide, or dibasic cesium phosphate, or tribasic cesium phosphate; a potassium buffer comprising, e.g., potassium bicarbonate, potassium borate, potassium carbonate, potassium hydroxide, or dibasic potassium phosphate, or tripotassium phosphate; a sodium buffer comprising, e.g., sodium bicarbonate, sodium borate, sodium carbonate, dibasic sodium phosphate, tribasic sodium phosphate, sodium hydroxide, or sodium tetraborate; a tetraalkylammonium buffer, comprising, e.g., tetraalkylammonium bicarbonate, tetraalkylammonium borate, tetraalkylammonium carbonate, or a tetraalkylammonium phosphate, in water, with or without the use of one of more of the following organic co-solvents such as acetonitrile, or acetone, or tetrahydrofuran (THF), or 1,4-dioxane, or dimethylformamide (DMF), or N-methyl pyrrolidone (NMP), or dimethyl sulfoxide (DMSO), or hexamethylphosphoramide (HMPA), or diethyl ether, or isopropyl alcohol (IPA), or t-butanol, or 2-butanol, etc., in a desired ratio, such as at/below/or above, 5%, or 10%, or 15%, or 20%, or 25%, or 30%, or 35%, or 40%, or 45%, or 50%, or 55%, or 60%, or 70%, or 75%, or 80%, or 85%, or 90%, or 95%, of organic in water.

The amount of buffer used in an elution solution may be any concentration that can effectively maintain the alkaline buffering capacity of the buffer. In aspects of this embodiment, an effective concentration of buffer may be, e.g., about 1.0 mM, about 5.0 mM, about 10 mM, about 20 mM, about 30 mM, about 40 mM, about 50 mM, about 60 mM, about 70 mM, about 80 mM, about 90 mM, about 100 mM, about 200 mM, about 300 mM, about 400 mM, about 500 mM, about 600 mM, about 700 mM, about 800 mM, or about 900 mM, or about 1 M. In other aspects of this embodiment, an effective concentration of buffer may be, e.g., at least 1.0 mM, at least 5.0 mM, at least 10 mM, at least 20 mM, at least 30 mM, at least 40 mM, at least 50 mM, at least 60 mM, at least 70 mM, at least 80 mM, at least 90 mM, at least 100 mM, at least 200 mM, at least 300 mM, at least 400 mM, at least 500 mM, at least 600 mM, at least 700 mM, at least 800 mM, or at least 900 mM, or at least 1 M. In yet other aspects of this embodiment, an effective concentration of buffer may be, e.g., at most 1.0 mM, at most 5.0 mM, at most 10 mM, at most 20 mM, at most 30 mM, at most 40 mM, at most 50 mM, at most 60 mM, at most 70 mM, at most 80 mM, at most 90 mM, at most 100 mM, at most 200 mM, at most 300 mM, at most 400 mM, at most 500 mM, at most 600 mM, at most 700 mM, at most 800 mM, or at most 900 mM, or at most 1 M.

In still other aspects of this embodiment, an effective concentration of elution buffer may be in the range of, e.g., about 0.1 mM to about 10 mM, about 0.1 mM to about 25 mM, about 0.1 mM to about 50 mM, about 0.1 mM to about 75 mM, about 0.1 mM to about 100 mM, about 0.1 mM to about 200 mM, about 0.1 mM to about 300 mM, about 0.1 mM to about 400 mM, about 0.1 mM to about 500 mM, about 0.1 mM to about 1000 mM, about 1 mM to about 10 mM, about 1 mM to about 25 mM, about 1 mM to about 50 mM, about 1 mM to about 75 mM, about 1 mM to about 100 mM, about 1 mM to about 200 mM, about 1 mM to about 300 mM, about 1 mM to about 400 mM, about 1 mM to about 500 mM, about 1 mM to about 1000 mM, about 5 mM to about 25 mM, about 5 mM to about 50 mM, about 5 mM to about 75 mM, about 5 mM to about 100 mM, about 5 mM to about 200 mM, about 5 mM to about 300 mM, about 5 mM to about 400 mM, about 5 mM to about 500 mM, about 5 mM to about 1000 mM, about 10 mM to about 25 mM, about 10 mM to about 50 mM, about 10 mM to about 75 mM, about 10 mM to about 100 mM, about 10 mM to about 200 mM, about 10 mM to about 300 mM, about 10 mM to about 400 mM, about 10 mM to about 500 mM, about 10 mM to about 1000 mM, about 25 mM to about 50 mM, about 25 mM to about 75 mM, about 25 mM to about 100 mM, about 25 mM to about 200 mM, about 25 mM to about 300 mM, about 25 mM to about 400 mM, about 25 mM to about 500 mM, about 25 mM to about 1000 mM, about 50 mM to about 75 mM, about 50 mM to about 100 mM, about 50 mM to about 200 mM, about 50 mM to about 300 mM, about 50 mM to about 400 mM, about 50 mM to about 500 mM, about 50 mM to about 1000 mM, about 75 mM to about 100 mM, about 75 mM to about 200 mM, about 75 mM to about 300 mM, about 75 mM to about 400 mM, about 75 mM to about 500 mM, about 75 mM to about 1000 mM, about 100 mM to about 150 mM, about 100 mM to about 200 mM, about 100 mM to about 300 mM, about 100 mM to about 400 mM, about 100 mM to about 500 mM, about 100 mM to about 1000 mM, about 200 mM to about 300 mM, about 200 mM to about 400 mM, about 200 mM to about 500 mM, about 200 mM to about 1000 mM, about 250 mM to about 300 mM, about 250 mM to about 400 mM, about 250 mM to about 500 mM, or about 250 mM to about 1000 mM. In another embodiment, an effective concentration of the elution buffer may be in the range of about 5 mM to about 250 mM.

An elution solution disclosed herein may comprise a derivatizing agent disclosed herein. The amount of derivatizing agent added to an elution solution disclosed herein is an amount in sufficient access to enable a complete derivatization of the analyte of interest for subsequent detection. The derivatizing reagent may be mixed with the elution buffer prior to the elution as in an in situ derivatization process, it may also be added to the eluent right after the elution to fashion a post elution derivatization process.

In one embodiment, the simultaneous elution and derivatization of the analyte may be accomplished by applying to the analyte bound to a solid sorbent support matrix a high pH elution buffer which includes a derivatizing agent. Upon application of the elution solution, a derivatization reaction occurs that converts the analyte to its derivative and then the derivative is eluted off the sorbent matrix at the same time as the elution of the analyte from the solid support matrix.

The derivatization reaction may be conducted under any condition suitable for the acylation of the analyte. In one embodiment, a derivatization reaction is performed under temperature conditions suitable for the attachment of the derivatizing agent to the analyte. In aspects of this embodiment, a derivatization reaction may be performed at a temperature range from about or above 0° C. to about or below 100° C., more preferably from about 5° C. to about 90° C., more preferably from 10° C. to 80° C., more preferably from 15° C. to 70° C., more preferably from 20° C. to 60° C., more preferably from 20° C. to 50° C.

A derivatization reaction is performed under time conditions suitable for the attachment of the derivatizing agent to the analyte. In aspects of this embodiment, the derivatization reaction is performed at duration range from 1 minute to about 24 hours, more preferably from 3 minutes to about 5 hours, more preferably from 5 minutes to 60 minutes, more preferably from 10 minutes to 30 minutes.

Of course, changing the temperature may change the reaction time. For instance, if the reaction is heated, for example, to 40° C., reaction time may be shortened.

The derivatization reaction may be quenched by addition of a buffered solution, which contains one or more of buffer agents. In one embodiment, the buffer is an ammonium buffer, such as ammonium formate, or ammonium acetate, or ammonium carbonate, or triammonium phosphate, or ammonium sulfate, or ammonium borate, ammonium hydroxide, ammonium chloride, ammonium sulfate, ammonium bicarbonate, ammonium bisulfate, bisammonium phosphate, etc. In another embodiment, the quenching reagent may also be a buffered □-amino acid solution, such as glycine, alanine, or a buffered □-alanine, or a buffered primary amine solution such as in a concentration range from 1 mM to 500 mM, in water, or a mixed solvent of water and an organic solvent, such as an alcohol, e.g., methanol, or ethanol, or propanol, or butanol, or glycol, or glycerol, or etc., or acetonitrile, or acetone, or ether, or THF, or 1,4-dioxanes, or DMF, or NMP, or DMSO, or HMPA. The quenching process neutralizes most of any excess derivatizing reagent that may remain in the eluent solution and also stabilizes the product by lowering the pH of the reaction mixture. In aspects of this embodiment, the pH of the eluent containing the derivatized analyte may be lowered to a range from about 4 to about 9.5.

After quenching, the reaction mixture containing derivatized analyte may then be directly analyzed for the presence of the analyte of interest. Such analysis may be either qualitative or quantitative in nature. In aspects of this embodiment, eluent containing derivatized analyte may be directly analyzed for the presence of the analyte of interest using, e.g., chromatography and/or mass spectroscopic detection.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), ultra-high pressure liquid chromatography (UHPLC), and turbulent flow liquid chromatography (TFLC) (sometimes known as high turbulence liquid chromatography) (HTLC) or high throughput liquid chromatography, or nano-flow liquid chromatography, or nano LC As used herein, the term "high performance liquid chromatography" or "HPLC" refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography (HTLC) or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., J Chromatogr. A 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., Turbulent Flow Analysis Measurement and Prediction, P. S. Bernard & J. M. Wallace, John Wiley & Sons, Inc., (2000); An Introduction to Turbulent Flow, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%.

Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select HPLC instruments and columns that are suitable for use with the analytes of interest. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded, a cyano bonded, or a pentafluorophenylpropyl (F5) surface, or phenyl/bonded, or biphenyl bonded surface. Alkyl bonded surfaces may include C-4, C-8, C-12, or C-18 bonded alkyl groups. In preferred embodiments, the column is a C-18 column. The chromatographic column includes an inlet port for receiving a sample directly or indirectly from a solid-phase extraction or HTLC column and an outlet port for discharging an effluent that includes the fractionated sample.

In certain embodiments, an analyte may be enriched in a sample by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be enriched in a sample by applying a sample to a column under mobile phase conditions where the analyte of interest elutes at a differential rate in comparison to one or more other materials. Such procedures may enrich the amount of one or more analytes of interest relative to one or more other components of the sample. In another embodiment, the reaction mixture of the analyte may be first loaded onto a guard column with a weak solvent to retain the desired analyte product on the guard column, then an LC elution solvent is to carry the substrate onto the analytical column for separation and analysis.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In one preferred embodiment, HPLC is conducted with a hydrophobic column chromatographic system. In certain preferred embodiments, a C18 analytical column (e.g., a TARGA® C18, 3 μm 50×2.1, or equivalent) is used. In certain preferred embodiments, HPLC are performed using HPLC Grade 5.0 mM ammonium formate with 0.1% formic acid at a pH of 3.0 and 0.1% formic acid in acetonitrile as the mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, the solid phase extraction may be used in a high throughput platform for enrichment of the derivatized analyte of interest prior to mass spectrometry. In such embodiments, samples may be extracted using a high throughput SPE cartridge, or a guard column which captures the derivatized analyte, then eluted onto an analytical HPLC column, such as a C-18 column, prior to mass spectrometry (MS) analysis. Because the steps involved in these chromatography procedures may be linked in an automated fashion, the requirement for operator involvement during the purification of the analyte can be minimized. This feature may result in savings of time and costs, and eliminate or reduce the opportunity for an operator error.

Direct quantification is "inline" or "on-line" use of the extracted and derivatized analyte for quantification. As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "sample injection" refers to introducing an aliquot of a single sample into an analytical instrument, for example a mass spectrometer. This introduction may occur directly or indirectly. An indirect sample injection may be accomplished, for example, by injecting an aliquot of a sample into a HPLC column that is connected to a mass spectrometer in an on-line fashion.

As used herein, the term "same sample injection" with respect to multiple analyte analysis by mass spectrometry means that the molecular ions for two or more different analytes are determined essentially simultaneously by measuring molecular ions for the different analytes from the same (i.e. identical) sample injection.

In various embodiments, the analytes of interest present in a test sample may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 1999, 2: 264-76; and Merchant and Weinberger, Electrophoresis 2000, 21: 1164-67.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which may be heated to prevent condensation and to facilitate solvent evaporation. As the droplets get smaller the electrical surface charge density increases until such time that the natural repulsion between like charges causes ions as well as neutral molecules to be released. In one embodiment, the detection is performed after ESI.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated N2 gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., Anal. Chem. 2000, 72(15): 3653-3659.

As used herein, the term "desorption" refers to translocation of an analyte from a liquid surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS filter and detector (quadrupole). By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g. m/z: 5-1250 for API 5000) The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples, and a standard curve constructed based on ions generated from those standards. Using such a standard curve, the relative abundance of a given ion may be converted into an absolute amount of the original molecule. In certain preferred embodiments, one or more internal standards may be used to generate standard curves for calculating the quantity of the analytes of interest. Methods of generating and using such standard curves are well known in the art and one of ordinary skill is capable of selecting appropriate internal standards. For example, an isotopically labeled catecholamine may be used as an internal standard; in certain preferred embodiments, d6-epinephrine and/or d6-norepinephrine and/or d4-dopamine may be used as internal standards. Numerous other methods for relating the amount of an ion to the amount of the original molecule will be well known to those of ordinary skill in the art.

In particularly preferred embodiments, the analytes of interest are quantified in a sample using MS/MS as follows. One or more of the analytes of interest in samples are first filtered through and eluted from a solid phase extraction column at a high pH in the presence of FMOC-Cl or a variant thereof. The resulting eluent is then subjected to liquid chromatography, preferably HPLC. The flow mobile phase from the chromatographic column enters the heated ESI probe of an MS/MS analyzer and the analytes ionized. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios the analytes of interest. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. This process is called collision activated dissociation (CAD), or collision induced dissociation (CID). The fragment ions generated are passed into quadrupole 3 (Q3), where the fragment ions are selected while other ions are eliminated. During analysis of a single sample, Q1 and/or Q3 may be adjusted such that mass/charge ratios of one or more precursor ion/fragment ion pairs specific to one catecholamine is first selected, followed at some later time by the selection of mass/charge ratios of one or more precursor ion/fragment ion pairs specific to a second catecholamine, optionally followed at some later time by the selection of mass/charge ratios of one or more precursor ion/fragment ion pairs specific to a third catecholamine and so on. In particularly preferred embodiments, mass to charge ratios of precursor/fragment ion pairs specific to epinephrine, mass to charge ratios of precursor/fragment ion pairs specific to norepinephrine, mass to charge ratios of precursor/fragment ion pairs specific to dopamine, mass to charge ratios of precursor/fragments of metanephrine, and mass to charge ratios of precursor/fragments of normetanephrine, are detected during analysis of a single sample, although the sequence of detection may occur in any order.

The methods may involve MS/MS performed in either positive or negative ion mode; preferably positive ion mode. Using standard methods well known in the art, one of ordinary skill is capable of identifying one or more fragment ions of a particular precursor ion of the analyte of interest that may be used for selection in quadrupole 3 (Q3).

In various embodiments, the analyte of interest is subjected to a mass spectrometry for detection and quantification. A mass spectrometry technique may employ atmospheric pressure chemical ionization (APCI) or electrospray ionization (ESI) to generate charged ions. The analyte of interest can present as a proton adduct or a protonated molecular ion, i.e. $[M+H^+]$ in the mobile phase. The analyte can also be shown the ammonium adduct $[M+NH_4^+]$ as a molecular ion when abundant ammonium ion is present in the mobile phase, or other cation adduct when corresponding cations are present in the mobile phase. Different adducts are also possible and can be recognized by the skilled artisan, and are generally shown by $[M+A+H]^+$, where A is the adduct. The adducts may or may not be solvated. During the ionization process, the molecular ions are desorbed into the gaseous phase, and then focused into the mass spectrometer for analysis and detection. See U.S. Pat. No. 6,692,971 for more information on APCI, as it is known to those of skill of the art.

MS analysis can be done with a single mass analyzer such as a single quadrupole mass spectrometer (MS), or a tandem mass analyzer such as a triple quadrupole tandem mass spectrometer (MS/MS). In a tandem mass spectrometry mode, the first mass filter or quadrupole (Q1) can be tuned to select independently, one or more of the molecular ions of the analyte of interest and internal standards of choice. The molecular ions (precursor ions) can undergo collision-induced dissociation (CID) at second quadrupole (Q2) to produce fragment or product ions. The fragment ions can be detected and analyzed at the second mass filter at Q3. This process can be referred to as product optimization. The second mass filter is then tuned to selectively monitor one or more of the most abundant product ions produced from a particular molecular ion. This technique is called multiple reaction monitoring (MRM).

Molecular ions [M+NH$_4^+$] of Fmoc derivatives of catecholamines are shown at below as MRM transitions of precursor-product ion pair can be monitored for catecholamines are listed below as examples:

| Dopamine-3Fmoc—NH$_4$ | | Epinephrine-3Fmoc—NH$_4$ | | Norepinephrine-3Fmoc—NH$_4$ | |
|---|---|---|---|---|---|
| 837.411 | 179.1 | 867.19 | 298.4 | 853.239 | 196.2 |
| 837.411 | 180.1 | 867.19 | 166.0 | 853.239 | 178.0 |
| 837.411 | 178.0 | 867.19 | 179.1 | 853.239 | 152.1 |
| 837.411 | 137.3 | 867.19 | 178.0 | 853.239 | 179.1 |
| 837.411 | 91.0 | 867.19 | 210.2 | 853.239 | 107.1 |
| 837.411 | 119.0 | 867.19 | 192.1 | 853.239 | 135.2 |
| 837.117 | 196.7 | 867.342 | 850.2 | | |
| 837.117 | 183.0 | | | | |
| 837.117 | 261.8 | | | | |
| 837.117 | 198.5 | | | | |

Internal standards, such as deuterated catecholamines, can be applied in the methods described herein. In one embodiment, Dopamine-d4 is used. In another embodiment, Epinephrine-d6 is employed. Yet in another embodiment, Norepinephrine-d6 is employed. The MRM transition pairs are listed as below:

| Dopamine-D4 | (+) | 841 | 179 |
|---|---|---|---|
| | (+) | 841 | 184 |
| Epinephrine-D6 | (+) | 873 | 304 |
| | (+) | 873 | 179 |
| Norepinephrine-D6 | (+) | 859 | 290 |
| | (+) | 859 | 202 |

Molecular ions [M+NH4+] of Fmoc derivatives of metanephrine and Normetanephrine are shown with the MRM transitions of precursor-product ion pairs as examples:

| Metanephrine-2FMOC—NH3 | | Normetanephrine-2FMOC—NH3 | |
|---|---|---|---|
| 659.21 | 268.4 | 645.1 | 166.1 |
| 659.21 | 624.3 | 645.1 | 210.2 |
| 659.21 | 179.1 | 645.1 | 254.3 |
| 659.21 | 642.5 | 645.1 | 178.0 |
| 659.21 | 180.1 | 645.1 | 179.0 |
| 659.21 | 178.0 | 645.1 | 149.3 |
| 659.21 | 446.5 | 645.1 | 121.2 |
| 659.21 | 224.3 | 645.1 | 134.0 |
| 659.21 | 165.0 | 645.1 | 106.0 |

Internal standards, such as deuterated Metanephrines, can be applied in the methods described herein. In one embodiment, Metanephrines-d6 is used. In another embodiment, Normetanephrines-d6 is employed. The MRM transition pairs are listed as below.

Molecular ions [M+NH$_4^+$] of Fmoc derivatives of thyroid hormones are shown at below as MRM transitions of precursor-product ion pair can be monitored for thyroid hormones are listed below as examples:

| rT3-2FMoc NH4 | | T3-2FMoc NH4 | | T4-2FMoc NH4 | |
|---|---|---|---|---|---|
| 1112.79 | 695.9 | 1112.9 | 696.1 | 1239.01 | 179.1 |
| 1112.79 | 179.2 | 1112.9 | 179.0 | 1239.01 | 821.8 |
| 1112.79 | 874.3 | 1112.9 | 634.6 | 1239.01 | 278.4 |
| 1112.79 | 178.1 | 1112.9 | 178.2 | 1239.01 | 178.0 |
| 1112.79 | 207.0 | 1112.9 | 649.9 | 1239.01 | 1008.3 |
| 1112.79 | 1029.8 | 1112.9 | 650.0 | 1239.01 | 708.6 |
| 1112.79 | 281.0 | 1112.9 | 517.4 | 1239.01 | 1006.4 |
| 1112.79 | 262.9 | 1112.9 | 263.0 | 1239.01 | 731.9 |
| 1112.79 | 283.2 | 1112.9 | 768.3 | 1239.01 | 337.0 |
| 1112.9 | 507.8 | 1113 | 479.0 | | |
| | | 1113.01 | 177.2 | | |
| | | 1113.01 | 605.7 | | |
| | | 1113.01 | 606.1 | | |
| | | 1113.01 | 855.4 | | |

Molecular ions [M+H$^+$] of Fmoc derivatives of thyroid hormones are shown at below as MRM transitions of precursor-product ion pair can be monitored for thyroid hormones are listed below as examples:

| rT3-2FMoc—H | | T3-2FMoc—H | | T4-2FMoc—H | |
|---|---|---|---|---|---|
| 1096.07 | 1012.7 | 1096.11 | 1012.8 | 1221.96 | 1054.7 |
| 1096.07 | 928.5 | 1096.11 | 928.6 | 1221.96 | 970.5 |
| 1096.07 | 844.5 | 1096.11 | 844.5 | 1221.96 | 337.1 |
| 1096.07 | 506.7 | 1096.11 | 506.7 | 1221.96 | 260.9 |
| 1096.07 | 206.9 | 1096.11 | 516.7 | 1221.96 | 262.9 |
| 1096.07 | 291.2 | 1096.11 | 265.0 | 1221.96 | 484.6 |
| 1096.07 | 263.1 | 1096.11 | 262.9 | 1221.96 | 206.9 |
| 1096.07 | 265.0 | 1096.11 | 207.1 | 1221.96 | 291.2 |
| 1096.07 | 273.0 | 1096.11 | 281.1 | 1221.96 | 1180.3 |
| 1096.6 | 508.8 | 1096.11 | 479.0 | | |

Internal standards can be applied in the methods described herein. In one embodiment, 3,3',5-triiodo-L-thyronine-$^{13}$C$_6$ (T3-$^{13}$C$_6$) is used. The MRM transition pairs are listed as below.

| 3,3',5-Triiodo-L-thyronine-$^{13}$C$_6$ (T3-$^{13}$C$_6$) | (+) | Quantitative | 1118.9 | 701.8 |
|---|---|---|---|---|
| | (+) | Confirmatory | 1118.9 | 655.9 |

Molecular ions [M+NH$_4^+$] of Fmoc derivatives of THC are shown at below as MRM transitions of precursor-product ion pair can be monitored for THC are listed below as examples:

| THC-FMoc—NH$_4^+$ | |
|---|---|
| 554.33 | 537.2 |
| 554.33 | 371.0 |
| 554.33 | 179.3 |
| 554.33 | 355.0 |
| 554.33 | 178.1 |
| 554.33 | 206.9 |

The methods disclosed herein can be evaluated by several parameters including, e.g., accuracy, precision, limit of detection (LOD), limits of quantitation (LOQ), linear range, specificity, selectivity, linearity, ruggedness, and system suitability. The accuracy of a method is the measure of exactness of an analytical method, or the closeness of agreement between the measured value and the value that is accepted as a conventional true value or an accepted reference value. The precision of a method is the degree of agreement among individual test results, when the procedure is applied repeatedly to multiple samplings of a homogeneous sample. As such, precision evaluates 1) within assay variability; 2) within-day variability (repeatability); and 3) between-day variability (intermediate precision); and 4) between-lab variability (reproducibility). Coefficient of variation (CV %) is a quantitative measure of precision expressed relative to the observed or theoretical mean value. The limit of detection (LOD) of a method refers to the concentration of analyte which gives rise to a signal that is significantly different from the negative control or blank and represents the lowest concentration of analyte that can be distinguished from background.

The limits of quantitation (LOQ) are the lowest and the highest concentrations of analyte in a sample that can be measured with an acceptable level of accuracy and precision. The lower limit of quantitation refers to the lowest dose that a detection method can measure consistently from the background. The upper limit of quantitation is the highest dose that a detection method can measure consistently before saturation of the signal occurs. The linear range of the method is the area between the lower and the upper limits of quantitation. The linear range is calculated by subtracting lower limit of quantitation from the upper limit of quantitation. As used herein, the term "signal to noise ratio for the lower asymptote" refers to the signal detected in the method at the lower limit of detection divided by the background signal. As used herein, the term "signal to noise ratio for the upper asymptote" refers to the signal detected in the method at the upper limit of detection divided by the background signal.

As used herein, an "amount" of an analyte in a body fluid sample refers generally to an absolute value reflecting the mass of the analyte detectable in volume of body fluid. However, an amount also contemplates a relative amount in comparison to another analyte amount. For example, an amount of analyte in a body fluid can be an amount which is greater than a control or normal level of analyte normally present.

The present methods and kits may be used for the quantification or the detection of an analyte of interest.

Aspects of the present specification may also be described as follows:

1. A method for determining the presence one or more analytes in a test sample, the method comprising: a) solid phase extraction of the one or more analytes from the test sample, b) elution of the one or more analytes from the solid phase extraction with an elution solution having a basic pH, or an acidic pH or a neutral pH c) in situ derivatization of the one or more analytes with a derivatizing agent, and d) detecting the one or more derivatized analytes using liquid chromatography and/or mass spectrometry.
2. A method for optimizing solid phase extraction (SPE) protocols of one or more analytes in a biological sample via in situ derivatization and LC-MS/MS detection.
3. The method of embodiment 1 or embodiment 2, wherein the one or more analytes is a compound having a primary amine, a secondary amine, or a phenolic hydroxyl group.
4. The method of any one of embodiments 1-3, wherein the one or more analytes is a drug, a hormone, a signaling agent, an amino acid, or a pesticide.
5. The method of any one of embodiments 1-4, wherein the one or more analytes is a monoamine neurotransmitter including catecholamine or one of its derivatives or metabolites, a sex hormone or one of its derivatives or metabolites, a cannabinoid or one of its derivatives or metabolites, a thyroid hormone or one of its derivatives or metabolites, an opiate, opioid or one of its derivatives or metabolites or an arylcyclohexylamine or one of its derivatives or metabolites, an Amphetamine or one of its derivatives or metabolites.
6. The method of any one of embodiments 1-5, wherein the catecholamine or one of its derivatives or metabolites is Catechol, Dopa, Dopamine, Epinephrine, Norepinephrine, 3-Methoxytyramine, p-Octopamine, Synephrine, Tyramine, 3,4-dihydroxybenzylamine, 3,4-Dihydroxymandelic acid, Dihydroxyphenylethylene glycol, DOPAL, DOPAC, Homovanillic acid, Hydroxytyrosol, 3-Methoxy-4-hydroxyphenylglycol, 3-Methoxytyramine (3-MT), MOPET, Normetanephrine, metanephrine, or Vanillylmandelic acid.
7. The method of embodiment 5, wherein monoamine neurotransmitter is Histamine, Tryptamine, Serotonin, or Agmatine.
8. The method of embodiment 5, wherein the sex hormone or one of its derivatives or metabolites is an estrogen.
9. The method of embodiment 8, wherein the estrogen is Estrone, Estradiol, Estriol, or Estetrol.
10. The method of embodiment 5, wherein the cannabinoid or one of its derivatives or metabolites is a Cannabigerol-type (CBG) cannabinoid, a Cannabichromene-type (CBC) cannabinoid, a Cannabidiol-type (CBD) cannabinoid, a Cannabinodiol-type (CBND) cannabinoid, a Tetrahydrocannabinol-type (THC) cannabinoid, a Cannabinol-type (CBN) cannabinoid, a Cannabitriol-type (CBT) cannabinoid, a Cannabielsoin-type (CBE) cannabinoid, an Isocannabinoid, a Cannabicyclol-type (CBL) cannabinoid, a Cannabicitran-type (CBT) cannabinoid, or a Cannabichromanone-type (CBCN) cannabinoid.
11. The method of embodiment 5, wherein the thyroid hormone or one of its derivatives or metabolites is 3, 3', 5-triiodothyronine (T3), 3, 3', 5'-triiodothyronine (rT3), or thyroxine (T4).
12. The method of embodiment 5, wherein the opiate, the opioid or the derivative or metabolite of the opiate or opioid, is morphine, oripavine, morphinone, hydromorphone, or oxymorphone.
13. The method of embodiment 5, wherein the opiate, the opioid, or the derivative or metabolite of the opiate or opioid is a benzylisoquinoline alkaloid, a semi-synthetic benzylisoquinoline alkaloid derivative, or an opioid.
14. The method of embodiment 5, wherein the arylcyclohexylamine or one of its derivatives or metabolites is Tiletamine, 3-Methoxetamine (MXE), Methoxyketamine, N-Ethylnorletamine (Ethketamine), Amphetamine, Ephedrine, or Methamphetamine.
15. The method of embodiment 5, wherein the Amphetamine or one of its derivatives or metabolites is Amphetamine (itself), methamphetamine, ephedrine, cathinone, 3,4-methylenedioxy-N-methylamphetamine (MDMA, "Ecstasy"), and 2,5-Dimethoxy-4-methylamphetamine (DOM, or "STP").
16. The method of any one of embodiments 1 or 3-15, wherein the solid phase extraction is performed with an ion exchange column or cartridge.
17. The method of embodiment 16, wherein the ion exchange column is a cation exchange column.
18. The method of embodiment 17, wherein the cation exchange column is a weak cation exchange column.
19. The method of embodiment 17, wherein the cation exchange column is a strong cation exchange column.
20. The method of embodiment 16, wherein the ion exchange column is an anion exchange column.

21. The method of any one of embodiments 1 or 3-20, wherein the solid phase extraction is performed with a reverse phase silica column or cartridge.
22. The method of embodiment 21, wherein the reverse phase silica is an alkyl bounded (C4, C8, C12, or C18) silica, a cyano bounded silica, a phenyl bounded silica, or a biphenyl bounded silica.
23. The method of one any of embodiments 1-22, wherein the sample is a biological sample, a soil sample, or a sample of food stuff.
24. The method of embodiment 23, wherein the biological sample is a blood sample, a saliva sample, a lachrymal sample, a urine sample, or a tissue sample.
25. The method of embodiment 24, wherein the blood sample is a full blood sample, a plasma sample, or a serum sample.
26. The method of any one of embodiments 1 or 3-25, wherein the basic pH is a pH of greater than about 8.
27. The method of embodiment 26, wherein the basic pH is a pH in the range of about 8 to about 13.
28. The method of any one of embodiments 1-27, wherein the derivatizing reagent is an acylating agent of Formula I:

(I)

29. The method of embodiment 28, wherein the acylating agent is an acyl chloride or acyl halide.
30. The method of embodiment 29, wherein the acyl chloride is Fmoc chloride Formula II.

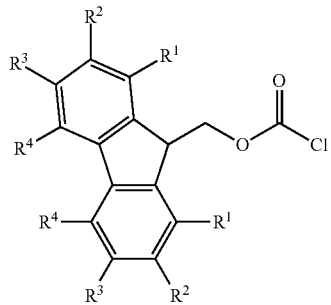
(II)

31. The method of embodiment 30, wherein $R^1$, $R^2$, $R^3$, and $R^4$ are each independently, H, fluorine, chlorine, bromine, iodine, a cyano group, an acetylene group, a propylene group, a vinyl group, a linear, branched, or cyclic $C_{1-8}$ alkyl, a substituted vinyl group, or a linear or branched or cyclic $C_{1-8}$ alkoxy group.
32. The method of embodiment 31, wherein the FMOC compound is shown in Formula III:

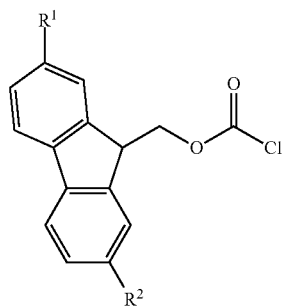
(III)

wherein $R^1$ and $R^2$ are each independently, H, fluorine, chlorine, bromine, iodine, a cyano group, an acetylene group, a propylene group, a vinyl group, a linear, branched, or cyclic $C_{1-8}$ alkyl, a substituted vinyl group, or a linear or branched or cyclic $C_{1-8}$ alkoxy group.
32. The method of embodiment 31, wherein the Fmoc chloride is represented as follows:

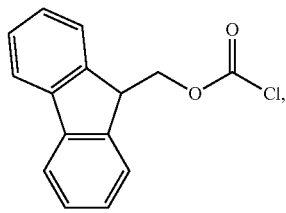

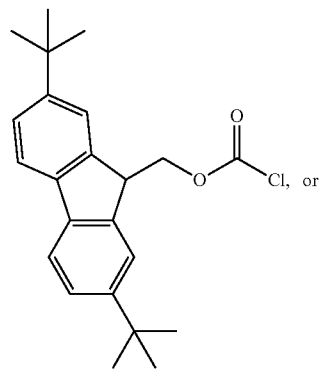

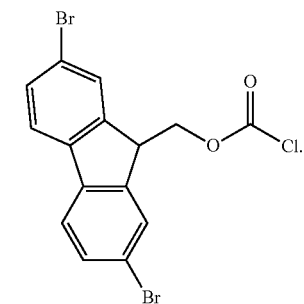

33. The method of embodiment 29, wherein the acyl chloride is Fmoc chloride Formula VII:

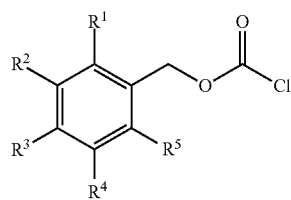

(VII)

34. The method of embodiment 33, wherein $R^1$, $R^2$, $R^3$, $R^4$, and $R^5$ are each independently H, a halogen atom such as a fluorine, or a chlorine, or a bromine, or an iodine, a cyano group, an acetylene group, a propylene group, a vinyl group, a linear or branched, or members of a cyclic $C_{1-8}$ alkyl, a substituted vinyl group, or a linear or branched $C_{1-8}$ alkoxy group or members of a cyclic $C_{1-8}$ alkoxy group.

35. The method of embodiment 33, wherein formula VII is represented as:

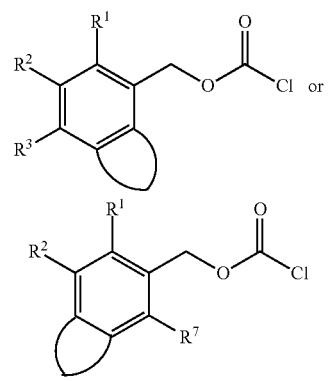

wherein the fused ring system is an all carbocyclic or a heterocyclic aromatic system, optionally a naphthalene, a quinolone, an isoquinoline, a quinzoline, a benzofuran, an indole, or a benzimidazole, with a 5-7 membered substituted or unsubstituted fused ring, or a nonaromatic carbocyclic, or heterocyclic fused ring system such as 3,4-dihydro-1H-indene, or a 3,4,dihydro-2H-chromene, with a 4-8 membered fused ring, wherein the fused ring may be substituted when appropriate by one or more of a halogen atoms, optionally fluorine, chlorine, bromine, or iodine, a cyano group, an acetylene group, a propylene group, a vinyl group, a linear, branched, or cyclic $C_{1-8}$ alkyl, a substituted vinyl group, or a linear, branched, or cyclic $C_{1-8}$ alkoxy group.

36. The method of embodiment 33, wherein Formula VII is

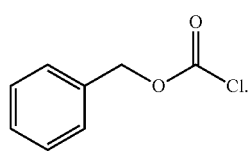 [SMILES: O=C(Cl)OCc1ccccc1]

37. The method of embodiment 29, wherein the acylation reagent is:

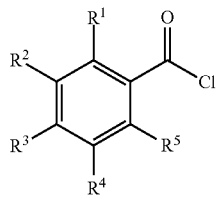

(VIII)

wherein $R^1$, $R^2$, $R^3$, $R^4$, and $R^5$ are each independently H, a halogen atom, optionally, fluorine, or a chlorine, or a bromine, or an iodine, a cyano group, an acetylene group, a propylene group, a vinyl group, a linear or branched $C_{1-8}$ alkyl, or members of a cyclic $C_{1-8}$ alkyl, a substituted vinyl group, a linear or branched $C_{1-8}$ alkoxy group, or members of a cyclic $C_{1-8}$ alkoxy group.

39. The method of embodiment 37, wherein Formula VIII may be represented as:

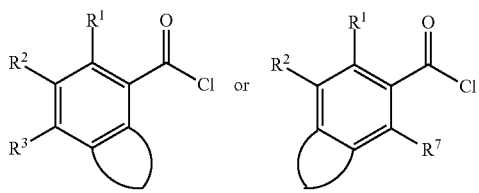

wherein the fused ring system may be an all carbocyclic or a heterocyclic aromatic system, having a 5-7 membered fused ring, or a nonaromatic carbocyclic, or heterocyclic fused ring system such as 3,4-dihydro-1H-indene, or a 3,4,dihydro-2H-chromene, or having a 4-8 membered fused ring, and wherein the fused ring may be substituted when appropriate with one or more of a halogen atom, a cyano group, an acetylene group, a propylene group, a vintyl group, a linear, branche or cyclic $C_{1-8}$ alkyl, a substituted vinyl group, or a linear or branched or cyclic $C_{1-8}$ alkoxy group.

40. The method of embodiment 37, wherein Formula VIII is benzoyl chloride:

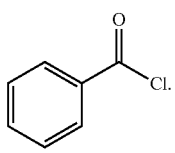

41. The method of embodiment 29, wherein the acylating reagent is Formula IX:

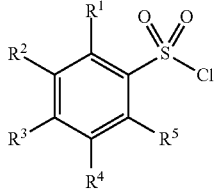

wherein $R^1$, $R^2$, $R^3$, $R^4$, and $R^5$ are each independently, a hydrogen, a halogen atom, optionally fluorine, chlorine, bromine, or iodine, a cyano group, an acetylene group, a propylene group, a vinyl group, a linear, branched, or cyclic $C_{1-8}$ alkyl, a substituted vinyl group, or a linear or branched or cyclic $C_{1-8}$ alkoxy group.

43. The method of embodiment 41, wherein Formula IX is:

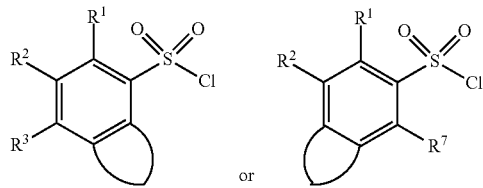

wherein the fused ring system may be an all carbocyclic or a heterocyclic aromatic system, optionally a naphthalene, a quinolone, an isoquinoline, a quinzoline, a benzofuran, an indole, or a benzimidazole, having a 5-7 membered fused ring, or a nonaromatic carbocyclic, or heterocyclic fused ring system optionally 3,4-dihydro-1H-indene, 3,4,dihydro-2H-chromene, having a 4-8 membered fused ring, and wherein the fused ring may be substituted when appropriate by one or more of a halogen atoms, optionally fluorine, chlorine, bromine, iodine, a cyano group, an acetylene group, a propylene group, a vinyl group, a linear, branched, or cyclic $C_{1-8}$ alkyl, a substituted vinyl group, or a linear or branched or cyclic $C_{1-8}$ alkoxy group.

44. The method of embodiment 28, wherein X is: Cl, Br, F,

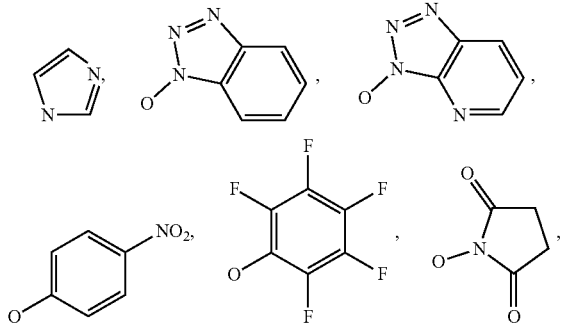

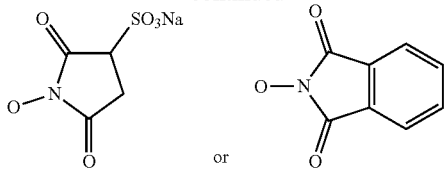

45. The method of any one of embodiments 1-44, wherein the mass spectrometry comprises tandem mass spectrometry techniques 46. The method of any one of embodiments 1-45, wherein the mass spectrometry comprises LC-MS/MS techniques.

47. The method of embodiment 46, wherein the LC-MS/MS techniques comprise Atmospheric Pressure Chemical Ionization (APCI), or Electrospray Ionization (ESI) technique.

48. The method of embodiment 46, wherein the LC-MS/MS techniques comprise the use of a triple quadrupole mass spectrometer instrument in Multiple Reaction Monitoring (MRM), or Selected Reaction Monitoring (SRM), positive-ion mode.

49. The method of embodiment 48, wherein the LC-MS/MS techniques comprise a Q1 scan tuned to select a precursor ion that corresponds to the $[M+H]^+$, or $[M+NH_4]^+$, or $[M+A+H]^+$ of the acylated derivatives of the desired one or more analytes for product optimization, wherein A is a molecular adduct, such as an acetonitrile, or an $H_2O$.

50. The method of embodiment 49, wherein the one or more analytes are at least one of Dopamine, Epinephrine, and Norepinephrine, the acylated derivatives of the one or more analytes are tri-Fmoc Dopamine ($[M+H]=820$, or $[M+NH_4]=837$), tri-Fmoc Epinephrine ($[M+H]=850$, or $[M+NH_4]=867$), and tri-Fmoc Norepinephrine ($[M+H]=836$, or $[M+NH_4]=853$).

51. The method of embodiment 49, wherein the one or more analytes are at least one of Metanephrine, and Normetanephrine and the acylated derivatives of the one or more analytes are bis-Fmoc Metanephrine ($[M+H]=642$, or $[M+NH_4]=659$), and bis-Fmoc Normetanephrine ($[M+H]=628$, or $[M+NH_4]=645$).

52. The method of embodiment 49, wherein the one or more analytes are at least one of Thyroxine (T4), and 3,3',5-triiodothyroine (T3), and 3,3',5'-triiodothyronine (rT3), the acylated derivatives of the one or more analytes are bis-Fmoc T4 $[M+H]=1222$, or $[M+NH_4]=1239$), bis-Fmoc T3 ($[M+H]=1096$, or $[M+NH_4]=1113$), and bis-Fmoc rT3 ($[M+H]=1096$, or $[M+NH_4]=1113$).

53. The method according to embodiment 49, wherein the one or more analytes are at least one of δ-9-tetrahydrocannabinol (THC) and 11-nor-9-carboxyl-d-9-tetrahydrocannabinol (9-carboxyl-THC) and the acylated derivative of δ-9-tetrahydrocannabinol (THC) is Fmoc-THC ($[M+H]=537$, or $[M+NH_4]=554$), and the acylated derivative of 11-nor-9-carboxyl-d-9-tetrahydrocannabinol (9-carboxyl-THC) is Fmoc-9-carboxyl-THC ($[M+H]=567$, $[M+NH_4]=584$).

54. The method of any one of embodiments 1-53, wherein the detection of the analyte is qualitative or quantitative.

55. A method for determining the amount of one or more one or more analytes in a sample the method comprising: elution of at least one of the one or more analytes from a solid phase extraction with an elution buffer comprising a derivatization agent under conditions that allow the derivatization the at least one of the one or more analytes.

56. A solid phase extraction kit for determining the amount of one or more analytes, the kit comprising: a) a solid phase extraction column, and b) an elution solution having a high pH with a derivatizing reagent in the same or a separate container.
57. The kit of embodiment 56, wherein the derivatization agent is an acylating reagent.
58. The kit of embodiment 57, wherein the acylating agent is an acyl chloride or acyl halide.
59. The kit of embodiment 58, wherein the acyl chloride is an FMOC-Cl or a variant thereof.
60. The kit of embodiment 58, wherein the acyl chloride is a CBZ-Cl or a variant thereof.
61. The kit of any one of embodiments 56-60, wherein the solid phase extraction column is a weak cation exchange column.
62. The kit of any one of embodiments 56-60, wherein the solid phase extraction column is a strong cation exchange column.
63. The kit of any one of embodiments 56-60, wherein the solid phase extraction column is a reverse phase column.
64. The kit of any one of embodiments 56-60, wherein the solid phase extraction column is an anion exchange column.

EXAMPLES

The following non-limiting examples are provided for illustrative purposes only in order to facilitate a more complete understanding of the disclosed subject matter. These examples should not be construed to limit any of the embodiments described in the present specification, including those pertaining to the methods for detecting an analyte and kits comprising the components necessary to perform the disclosed methods.

Example 1

Quantification of Catecholamines in Blood Plasma

Plasma samples were obtained from human patients' blood. Samples were drawn (plasma sodium heparin & EDTA) into pre-chilled Vacutainers. Vacutainers were inverted 5× and refrigerated until centrifuged. Plasma was separated in a refrigerated centrifuge (1000×g for 10 minutes) within 30 minutes of collection and then frozen immediately at −20° C. in plastic vials. Plasma was thawed and diluted before use in solid phase extraction. The blanks, calibration samples, and plasma samples were spiked with internal standards (e.g., dopamine-D4, epinephrine-D6, and norepinephrine-D6). Standard curves were generated with plasma solutions spiked with a known amount of catecholamine. The spiking solution was serially diluted before being added to the plasma taken from the same plasma sample.

CEREX® PWCX HP (1 cc/10 mg) columns (catalog number 675-0101R) were conditioned with 0.5 ml of methanol, followed by 0.5 ml of 10 mM Phosphate Buffer pH 6.8. Another 0.5 ml of 10 mM phosphate buffer at pH 6.8 was added to the column. Then 0.5 ml 10 mM Phosphate buffer was mixed with 100 μL of the Sample. The Sample/buffer mix was loaded onto the column at a pressure of 2-3 psi. The column was washed with 1 ml deionized water at 2-3 psi and subsequently washed with 1 ml Acetonitrile at 6 psi.

The sample was eluted from the column with 0.5 ml of Elution Buffer; a 4% w/v FMoc-Cl in 25 mM $K_2CO_3$ solute in a solution of water and acetonitrile. ($H_2O$: Acetonitrile=1: 3). The derivatization reaction was permitted to proceed for 12 minutes at room temperature. The derivatization reaction was stopped with 20 μL of 10 mM ammonium formate. 25 μL of the solution obtained from the ammonium formate reaction was used directly as the sample injected in the LC-MS/MS analysis.

For LC-MS/MS analysis, 25 μL of the solution obtained from the ammonium formate reaction was automatically injected into a TARGA® C18 3 μm particle size 50×2.1 mm analytical column. A binary HPLC gradient was applied to the analytical column to separate the FMoc derivatives of epinephrine, norepinephrine and dopamine from other analytes contained in the sample. Mobile phase A was 5.0 mM ammonium formate with 0.1% formic acid pH 3.0 and mobile phase B was Acetonitrile with 0.1% formic acid. The HPLC gradient proceeded at a temperature of 35° C. with a flow rate of 500 μl/min over five minutes as follows: 0.01 min, 50% B; 3.0 min, 100% B, 4.0 min 100% B, 4.5 min, 50% B, 5.0 min, 50% B.

MS/MS was performed using an API 5000 triple quadrupole mass spectrometer controlled by Analyst Software Version 1.52 (ABI-SCIEX, Toronto, Canada). Analyte exiting the HPLC analytical column through the mobile phase flowed to the heated nebulizer interface of the MS/MS analyzer. The solvent/analyte mixture was converted to vapor in the heated tubing of the interface. Analytes in the nebulized solvent were ionized by heated Electrospray Ionization source.

Ions passed to the first quadrupole (Q1), which selected ions with a mass to charge ratio of parent ions generated from one of the analytes. Ions entering quadrupole 2 (Q2) collided with collision gas to generate ion fragments, which were passed to quadrupole 3 (Q3) for further selection. Simultaneously, the same process using isotope dilution mass spectrometry was carried out with internal standards, dopamine-D4 and/or epinephrine-D6, and/or norepinephrine-D6. The following mass transitions were used for detection and quantitation of epinephrine, norepinephrine and dopamine (and their corresponding internal standards) during validation on positive polarity from the same sample injection.

TABLE 1

| Ions Monitored | | | |
| --- | --- | --- | --- |
| Compound | Polarity | Precursor m/z | Product m/z |
| Dopamine | (+) | 837 | 180 |
|  | (+) | 837 | 137 |
| Dopamine-D4 | (+) | 841 | 179 |
|  | (+) | 841 | 184 |
| Epinephrine | (+) | 867 | 298 |
|  | (+) | 867 | 166 |
| Epinephrine-D6 | (+) | 873 | 304 |
|  | (+) | 873 | 179 |
| Norepinephrine | (+) | 853 | 196 |
|  | (+) | 853 | 152 |
| Norepinephrine-D6 | (+) | 859 | 290 |
|  | (+) | 859 | 202 |

The structure of the derivatized catecholamines is provided below (the ammonium adducts).

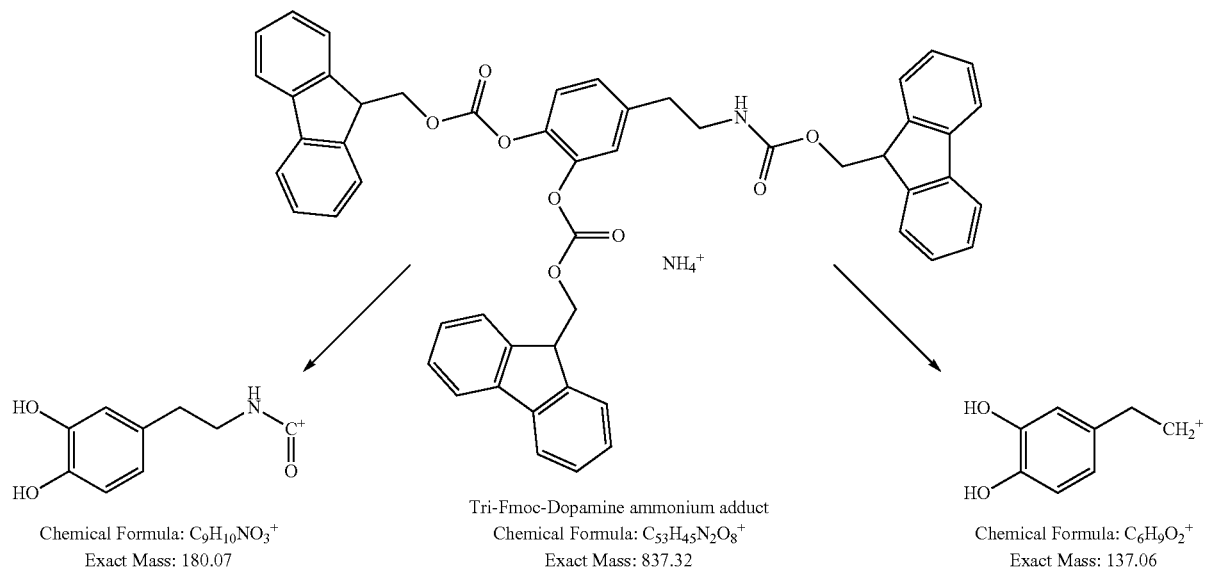
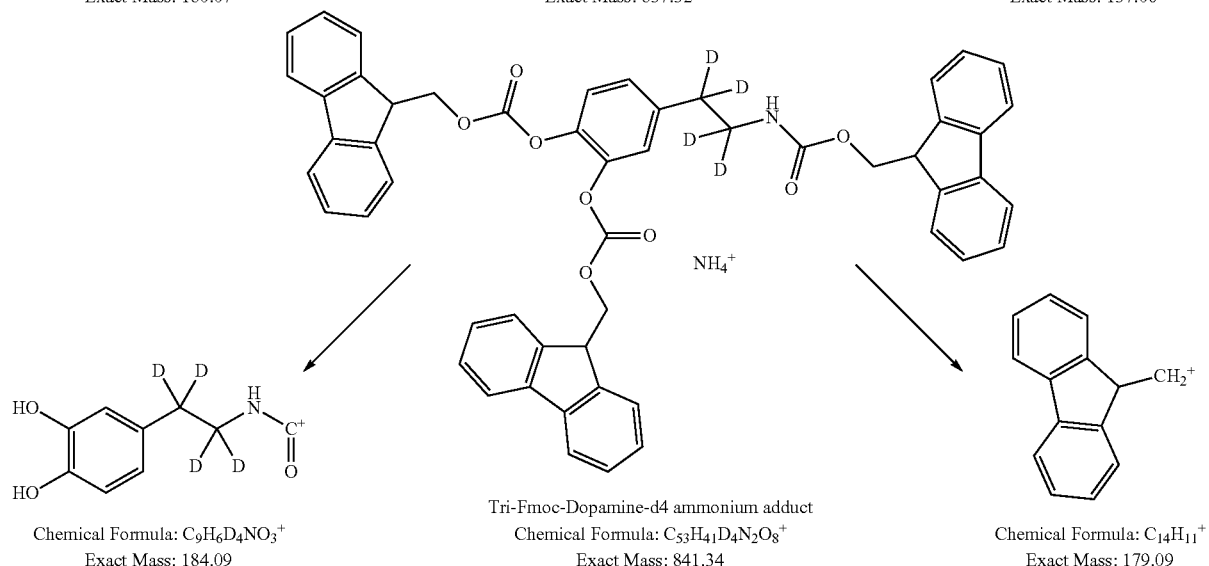
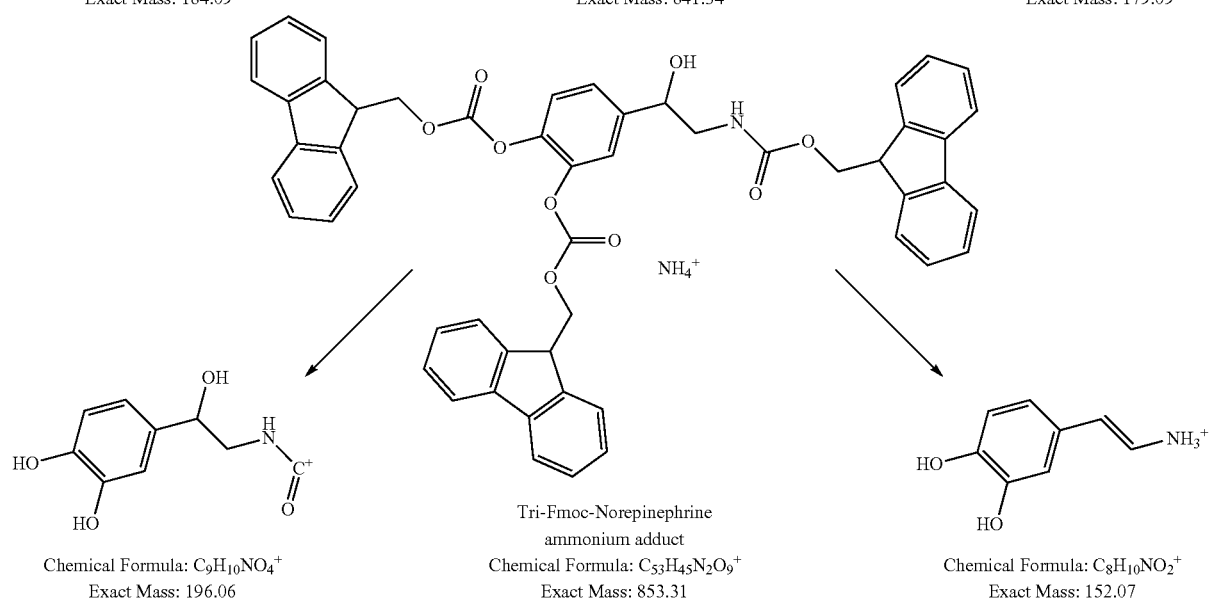

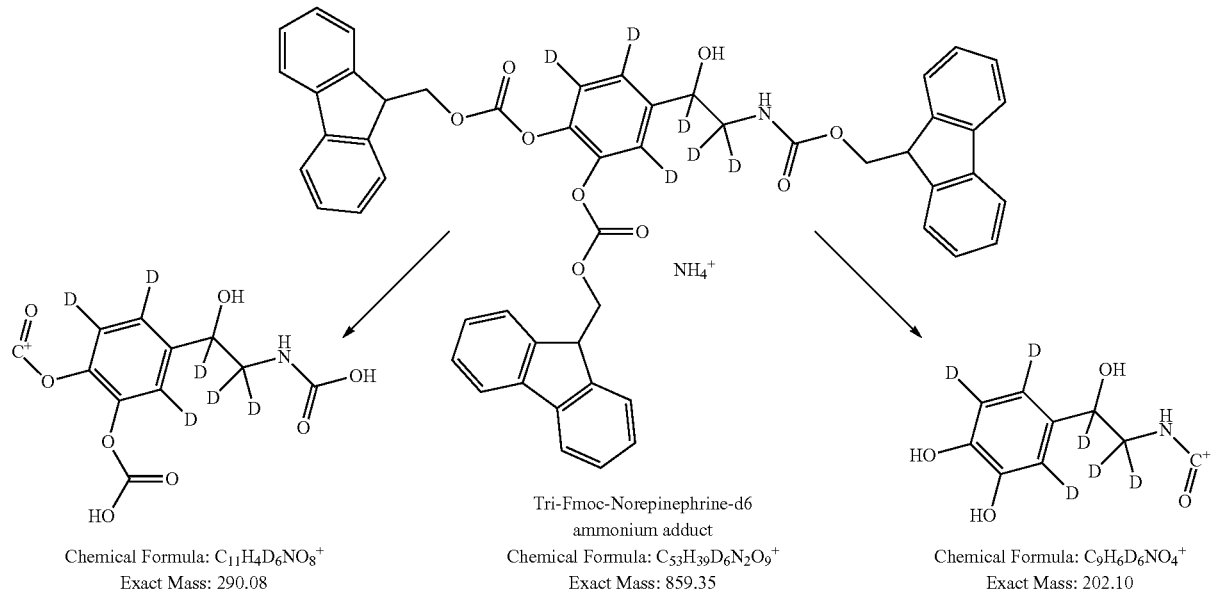
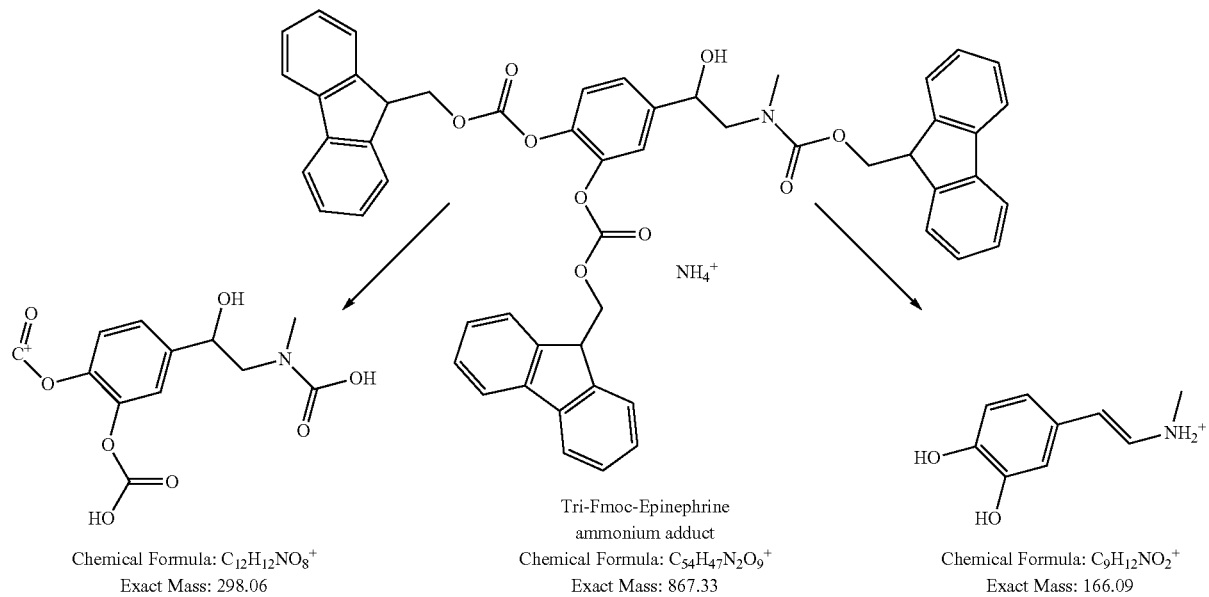

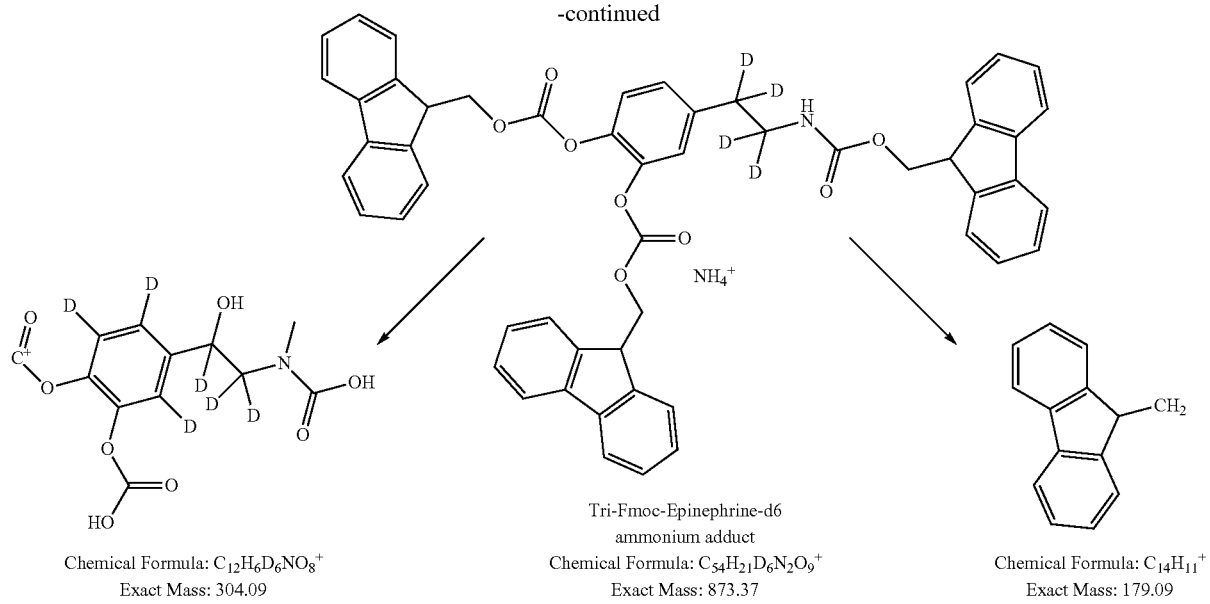

Figure 1B:
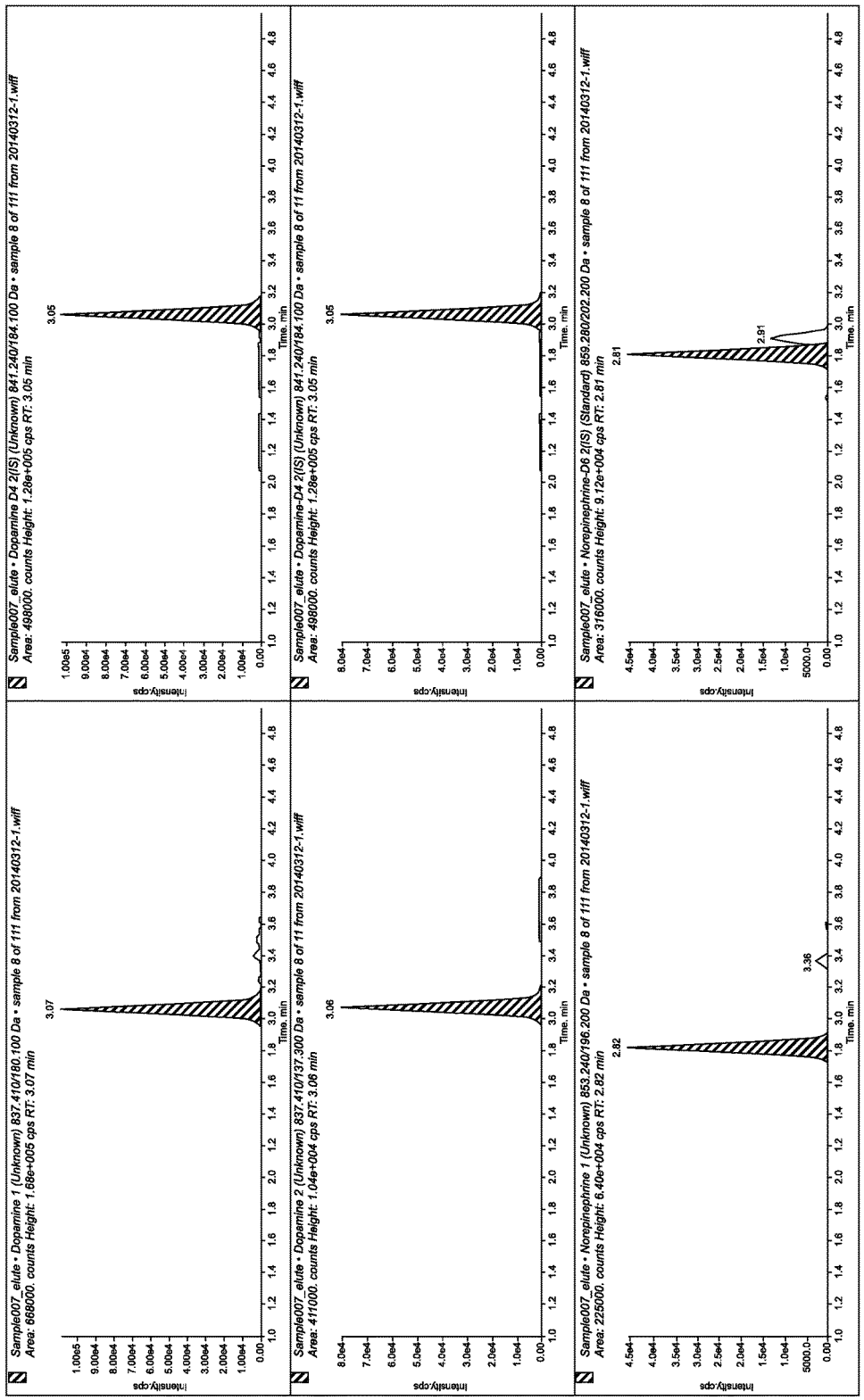

Table 2 shows the data representing the percent recovery of catecholamine from a plasma sample spiked with 1 ng/ml catecholamine. FIGS. 1A and 1B present example data showing the chromatograms for the internal standard equivalent (FIG. 1A) and for the catecholamine spiked plasma (FIG. 1B).

TABLE 2

Absolute Recovery: 1 ng/ml in Plasma

| Sample | Analyte | Analyte Peak Area (counts) | IS Peak Area (counts) | Area Ratio | Mean (Area Ratio) | SD (Area Ratio) | % C.V. (Area Ratio) | % Recovery |
|---|---|---|---|---|---|---|---|---|
| Std. 1 | DA-1 | 436000 | 416000 | 1.05 | 1.06 | 0.0404 | 3.8 | |
| Std. 2 | | 114000 | 112000 | 1.02 | | | | |
| Std. 3 | | 378000 | 342000 | 1.1 | | | | |
| Elution 1 | | 668000 | 498000 | 1.34 | 1.26 | 0.0883 | 7.0 | 119.2 |
| Elution 2 | | 636000 | 558000 | 1.14 | | | | |
| Elution 3 | | 696000 | 558000 | 1.25 | | | | |
| Elution 4 | | 699000 | 535000 | 1.31 | | | | |
| Std. 1 | DA-2 | 326000 | 416000 | 0.784 | 0.75 | 0.0454 | 6.1 | |
| Std. 2 | | 77800 | 112000 | 0.697 | | | | |
| Std. 3 | | 261000 | 342000 | 0.763 | | | | |
| Elution 1 | | 411000 | 498000 | 0.825 | 0.77 | 0.0568 | 7.4 | 103.3 |
| Elution 2 | | 386000 | 558000 | 0.692 | | | | |
| Elution 3 | | 437000 | 558000 | 0.783 | | | | |
| Elution 4 | | 423000 | 535000 | 0.791 | | | | |
| Std. 1 | EP-1 | 383000 | 319000 | 1.2 | 1.14 | 0.0666 | 5.8 | |
| Std. 2 | | 160000 | 138000 | 1.16 | | | | |
| Std. 3 | | 398000 | 372000 | 1.07 | | | | |
| Elution 1 | | 509000 | 393000 | 1.3 | 1.17 | 0.1163 | 9.9 | 102.3 |
| Elution 2 | | 487000 | 473000 | 1.03 | | | | |
| Elution 3 | | 558000 | 456000 | 1.22 | | | | |
| Elution 4 | | 497000 | 441000 | 1.13 | | | | |
| Std. 1 | EP-2 | 283000 | 319000 | 0.887 | 0.78 | 0.0954 | 12.2 | |
| Std. 2 | | 96900 | 138000 | 0.704 | | | | |
| Std. 3 | | 278000 | 372000 | 0.749 | | | | |
| Elution 1 | | 327000 | 393000 | 0.833 | 0.75 | 0.0787 | 10.5 | 95.6 |
| Elution 2 | | 304000 | 473000 | 0.642 | | | | |
| Elution 3 | | 342000 | 456000 | 0.749 | | | | |
| Elution 4 | | 334000 | 441000 | 0.759 | | | | |
| Std. 1 | NE-1 | 173000 | 177000 | 0.976 | 0.97 | 0.0220 | 2.3 | |
| Std. 2 | | 51700 | 51900 | 0.996 | | | | |

TABLE 2-continued

Absolute Recovery: 1 ng/ml in Plasma

| Sample | Analyte | Analyte Peak Area (counts) | IS Peak Area (counts) | Area Ratio | Mean (Area Ratio) | SD (Area Ratio) | % C.V. (Area Ratio) | % Recovery |
|---|---|---|---|---|---|---|---|---|
| Std. 3 | | 162000 | 170000 | 0.952 | | | | |
| Elution 1 | | 225000 | 316000 | 0.711 | 0.78 | 0.0680 | 8.8 | 79.6 |
| Elution 2 | | 228000 | 313000 | 0.73 | | | | |
| Elution 3 | | 262000 | 306000 | 0.857 | | | | |
| Elution 4 | | 256000 | 317000 | 0.807 | | | | |
| Std. 1 | NE-2 | 127000 | 177000 | 0.719 | 0.74 | 0.0312 | 4.2 | |
| Std. 2 | | 38100 | 51900 | 0.734 | | | | |
| Std. 3 | | 133000 | 170000 | 0.779 | | | | |
| Elution 1 | | 187000 | 316000 | 0.591 | 0.64 | 0.0568 | 8.9 | 85.4 |
| Elution 2 | | 182000 | 313000 | 0.582 | | | | |
| Elution 3 | | 208000 | 306000 | 0.681 | | | | |
| Elution 4 | | 218000 | 317000 | 0.688 | | | | |

As shown by Table 2, the extraction efficiency with FMOC-Cl derivatized catecholamines was very high.

When testing the linearity of the present detection methods, duplicates of each plasma sample spiked with the catecholamine of interest were tested.

TABLE 3

Linearity - 10 pg/ml to 100 ng/ml in Plasma

| Analyte Peak | Analyte Conc. (pg/mL) | Analyte Peak Area (counts) | Area Ratio | IS Peak Area (counts) | Calculated Conc. (pg/mL) | Accuracy (%) |
|---|---|---|---|---|---|---|
| DA-1 | 10 | 6510 | 0.0179 | 364000 | 9.22 | 92.2 |
| DA-1 | 10 | 7280 | 0.0216 | 337000 | 11.7 | 117 |
| DA-1 | 100 | 57000 | 0.16 | 357000 | 103 | 103 |
| DA-1 | 100 | 50800 | 0.142 | 358000 | 91 | 91 |
| DA-1 | 1000 | 506000 | 1.59 | 317000 | 1050 | 105 |
| DA-1 | 1000 | 449000 | 1.39 | 323000 | 916 | 91.6 |
| DA-1 | 10000 | 3780000 | 14.4 | 263000 | 9680 | 96.8 |
| DA-1 | 10000 | 4400000 | 15.4 | 286000 | 10400 | 104 |
| DA-1 | 100000 | 20600000 | 113 | 183000 | 93000 | 93 |
| DA-1 | 100000 | 20300000 | 125 | 162000 | 107000 | 107 |
| DA-2 | 10 | 5130 | 0.0141 | 364000 | 11.4 | 114 |
| DA-2 | 10 | 4800 | 0.0142 | 337000 | 11.5 | 115 |
| DA-2 | 100 | 37900 | 0.106 | 357000 | 98.8 | 98.8 |
| DA-2 | 100 | 33300 | 0.0931 | 358000 | 86.3 | 86.3 |
| DA-2 | 1000 | 319000 | 1.01 | 317000 | 953 | 95.3 |
| DA-2 | 1000 | 302000 | 0.936 | 323000 | 887 | 88.7 |
| DA-2 | 10000 | 2830000 | 10.8 | 263000 | 10400 | 104 |
| DA-2 | 10000 | 2890000 | 10.1 | 286000 | 9760 | 97.6 |
| DA-2 | 100000 | 14400000 | 79 | 183000 | 91000 | 91 |
| DA-2 | 100000 | 14800000 | 90.8 | 162000 | 109000 | 109 |
| EP-1 | 10 | 4410 | 0.0234 | 189000 | 9.29 | 92.9 |
| EP-1 | 10 | 4790 | 0.0246 | 195000 | 10 | 100 |
| EP-1 | 100 | 35100 | 0.184 | 190000 | 106 | 106 |
| EP-1 | 100 | 36900 | 0.182 | 203000 | 104 | 104 |
| EP-1 | 1000 | 319000 | 1.73 | 184000 | 1040 | 104 |
| EP-1 | 1000 | 278000 | 1.55 | 179000 | 927 | 92.7 |
| EP-1 | 10000 | 2690000 | 17.5 | 153000 | 10800 | 108 |
| EP-1 | 10000 | 2610000 | 15 | 174000 | 9220 | 92.2 |
| EP-1 | 100000 | 15300000 | 117 | 131000 | 93000 | 93 |
| EP-1 | 100000 | 16300000 | 128 | 127000 | 108000 | 108 |
| EP-2 | 10 | 3430 | 0.0181 | 189000 | 10.3 | 103 |
| EP-2 | 10 | 3590 | 0.0184 | 195000 | 10.6 | 106 |
| EP-2 | 100 | 22900 | 0.12 | 190000 | 113 | 113 |
| EP-2 | 100 | 20300 | 0.1 | 203000 | 92.6 | 92.6 |
| EP-2 | 1000 | 161000 | 0.877 | 184000 | 874 | 87.4 |
| EP-2 | 1000 | 173000 | 0.964 | 179000 | 962 | 96.2 |
| EP-2 | 10000 | 1470000 | 9.61 | 153000 | 9800 | 98 |
| EP-2 | 10000 | 1770000 | 10.2 | 174000 | 10400 | 104 |
| EP-2 | 100000 | 10500000 | 80.1 | 131000 | 94700 | 94.7 |
| EP-2 | 100000 | 11100000 | 87.3 | 127000 | 105000 | 105 |
| NE-1 | 10 | 993 | 0.00567 | 175000 | 9.42 | 94.2 |
| NE-1 | 10 | 955 | 0.00555 | 172000 | 9.18 | 91.8 |
| NE-1 | 100 | 9160 | 0.0513 | 178000 | 98.8 | 98.8 |
| NE-1 | 100 | 10600 | 0.0476 | 223000 | 91.6 | 91.6 |
| NE-1 | 1000 | 91800 | 0.629 | 146000 | 1230 | 123 |
| NE-1 | 1000 | 82700 | 0.526 | 157000 | 1030 | 103 |
| NE-1 | 10000 | 722000 | 4.9 | 147000 | 9790 | 97.9 |
| NE-1 | 10000 | 765000 | 4.96 | 154000 | 9920 | 99.2 |
| NE-1 | 100000 | 4750000 | 37.5 | 126000 | 90300 | 90.3 |
| NE-1 | 100000 | 4530000 | 43.5 | 104000 | 110000 | 110 |
| NE-2 | 10 | 1030 | 0.00586 | 175000 | 9.55 | 95.5 |
| NE-2 | 10 | 864 | 0.00502 | 172000 | 7.47 | 74.7 |
| NE-2 | 100 | 7540 | 0.0422 | 178000 | 99.3 | 99.3 |
| NE-2 | 100 | 9620 | 0.0432 | 223000 | 102 | 102 |
| NE-2 | 1000 | 70300 | 0.482 | 146000 | 1190 | 119 |
| NE-2 | 1000 | 72700 | 0.462 | 157000 | 1140 | 114 |
| NE-2 | 10000 | 572000 | 3.88 | 147000 | 9730 | 97.3 |
| NE-2 | 10000 | 609000 | 3.95 | 154000 | 9900 | 99 |
| NE-2 | 100000 | 4220000 | 33.3 | 126000 | 97600 | 97.6 |
| NE-2 | 100000 | 3610000 | 34.7 | 104000 | 102000 | 102 |

Figure 2A:
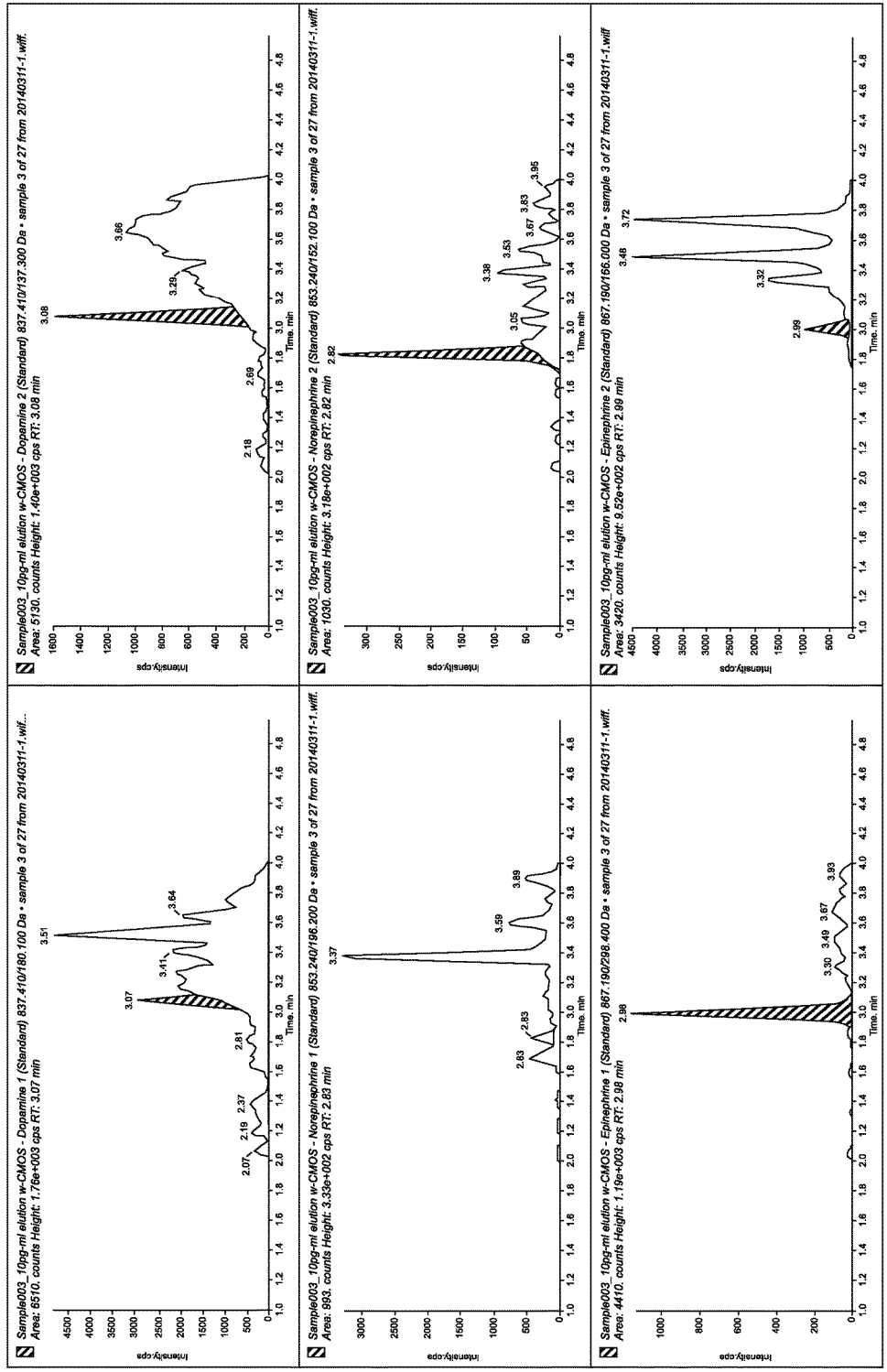
FIGS. 2A and 2B represent data obtained at 10 and 100 pg/ml of each catecholamine.
Figure 2B:
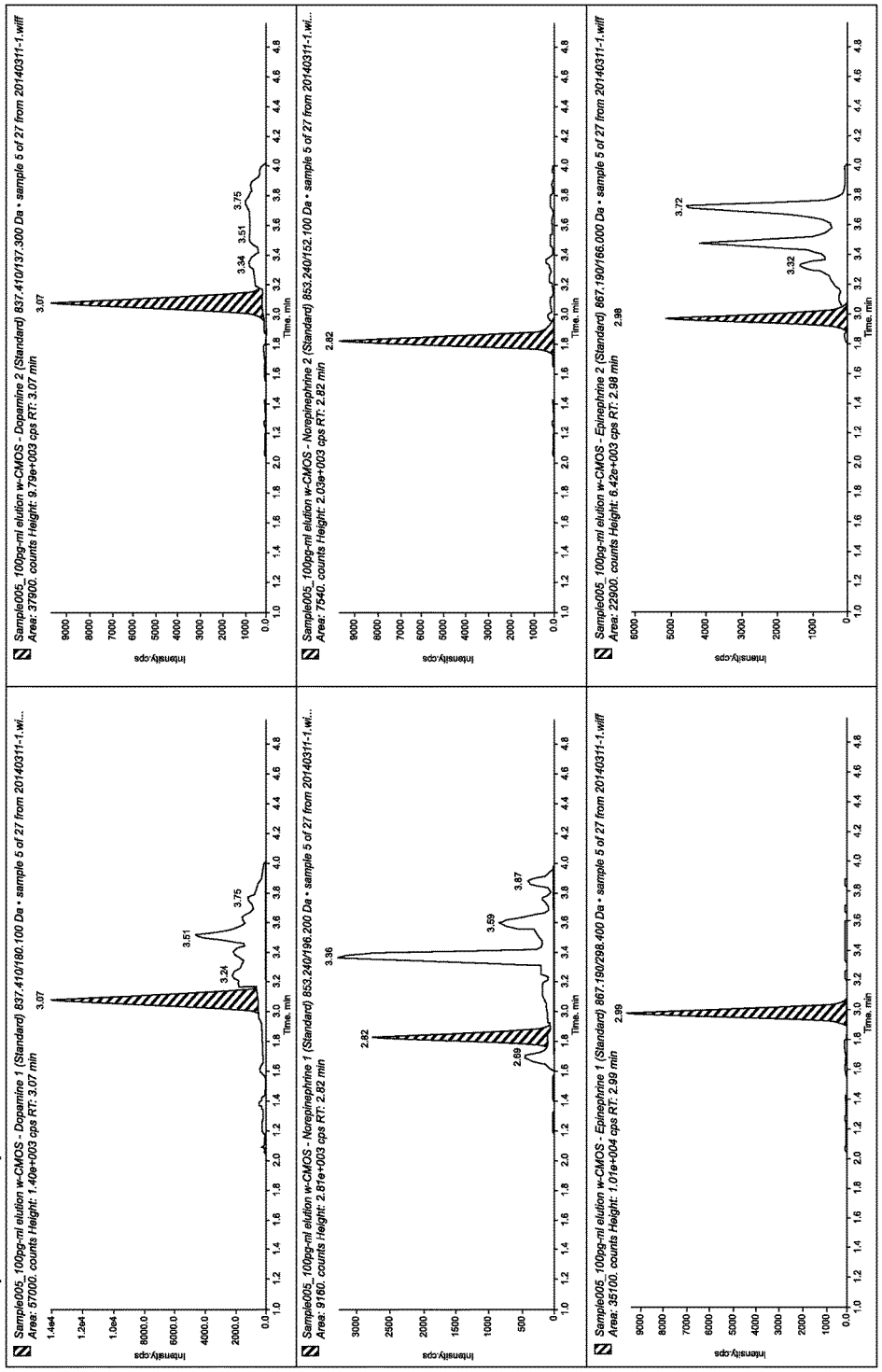
Figure 3:
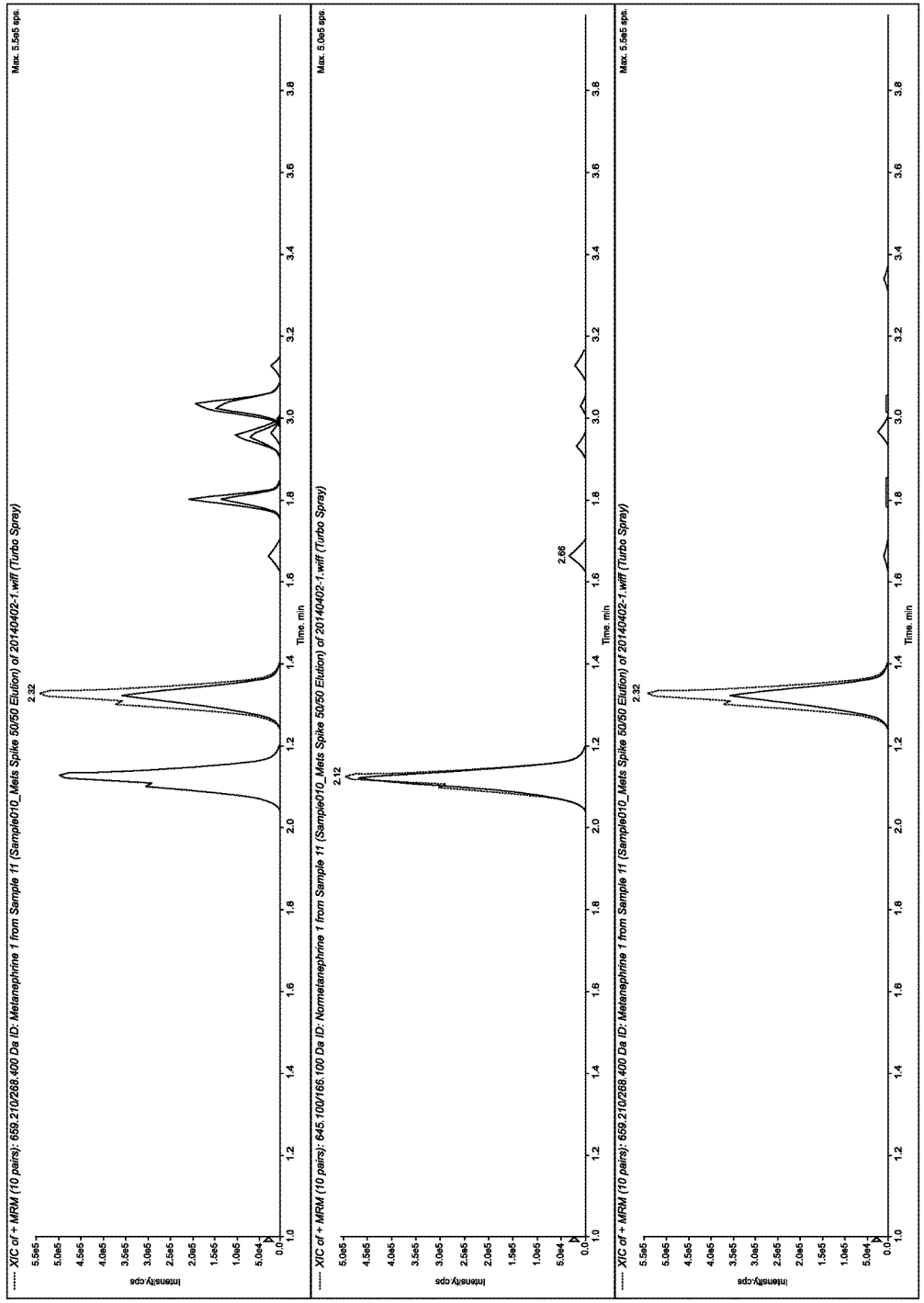
FIG. 3 provides the chromatograms for the metanephrines: top being metanephrine (659.210/268.400), middle being normetanephrine (645.100/166.100) and lower being metanephrine (659.210/268.400).
Figure 4A:
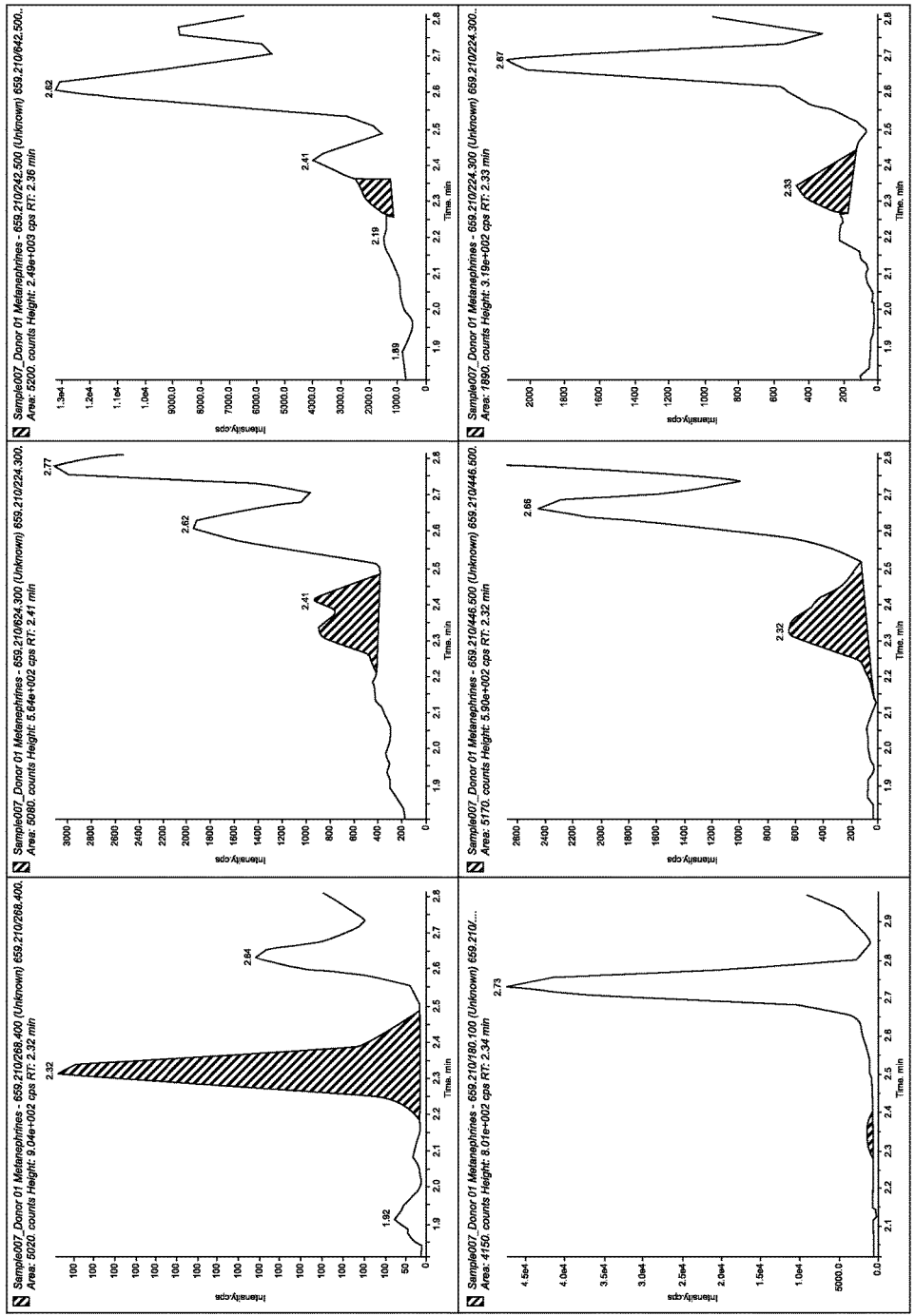
FIGS. 4A, 4B, 4C, and 4D provide the spectra for the various shifts in metanephrine and normetanephrine.
Figure 4B:
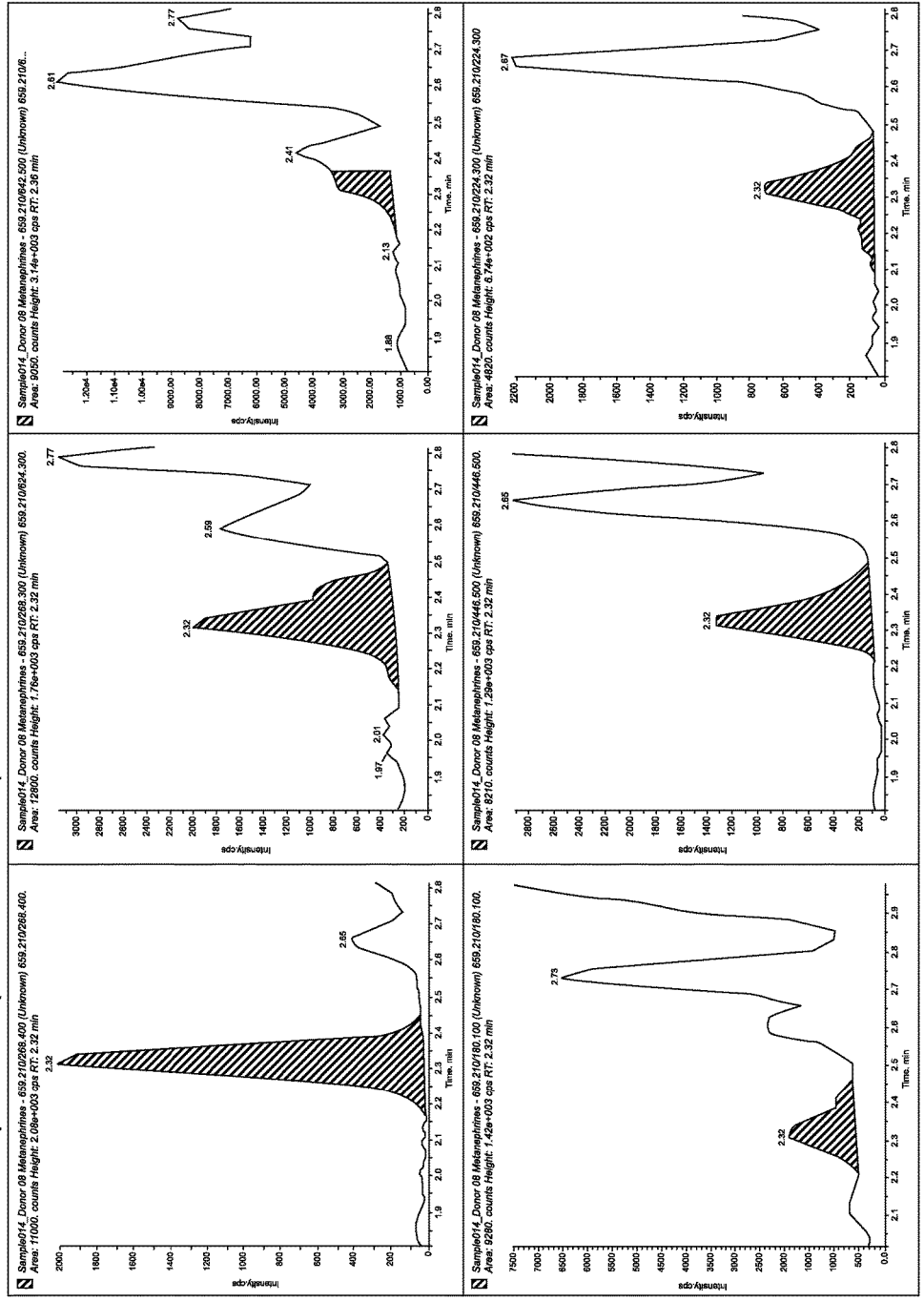
Figure 4C:
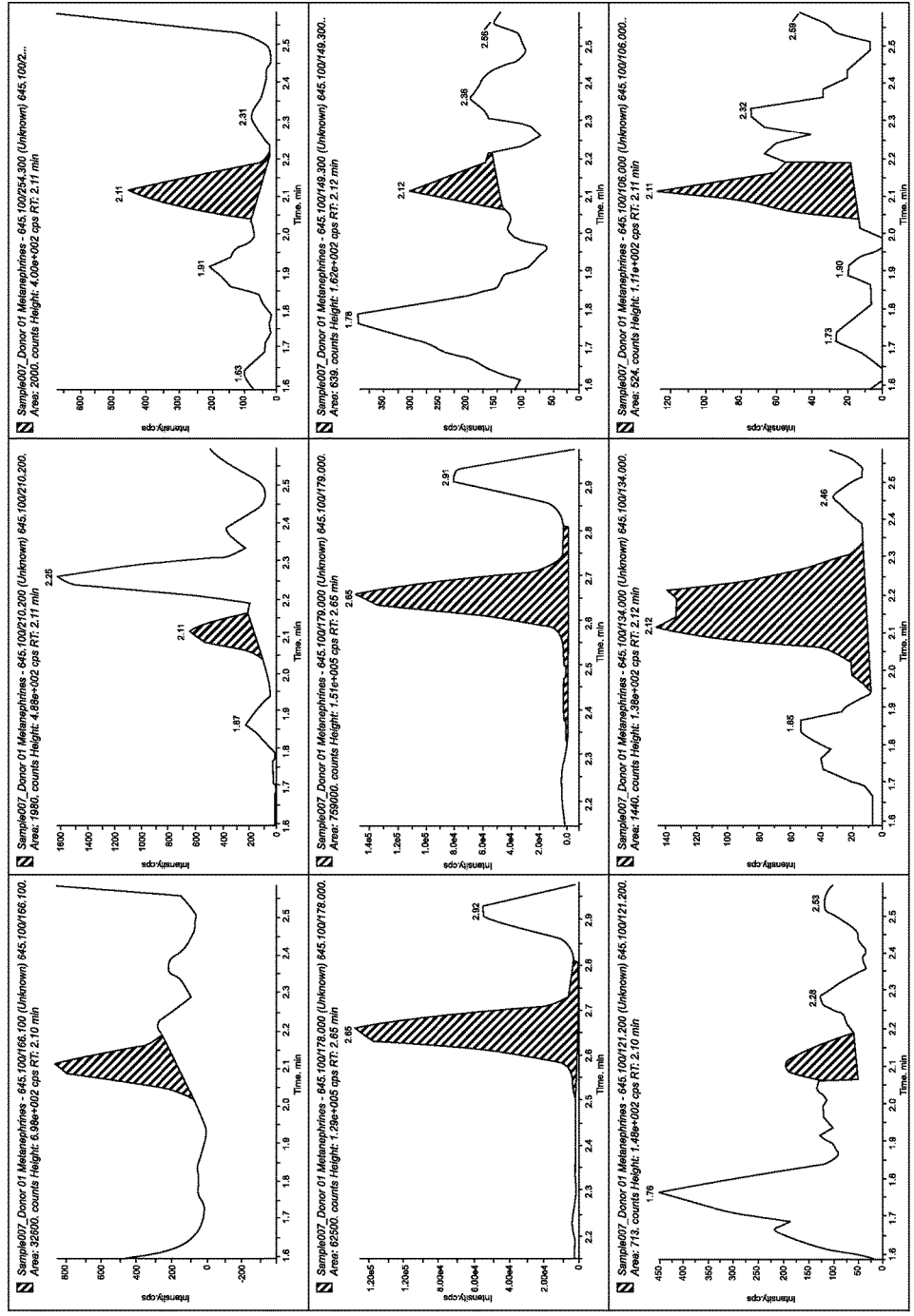
Figure 4D:
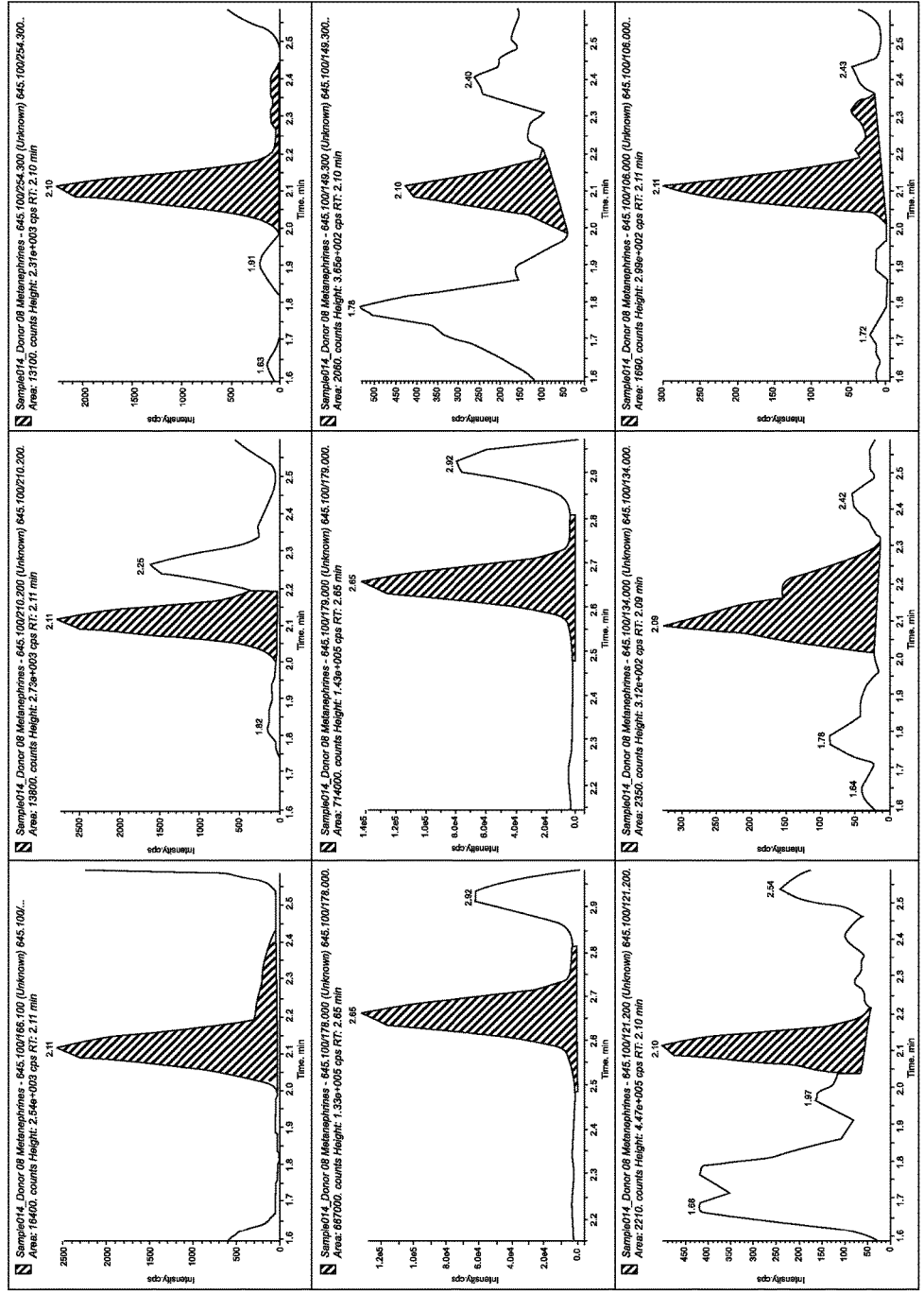
Figure 5A:
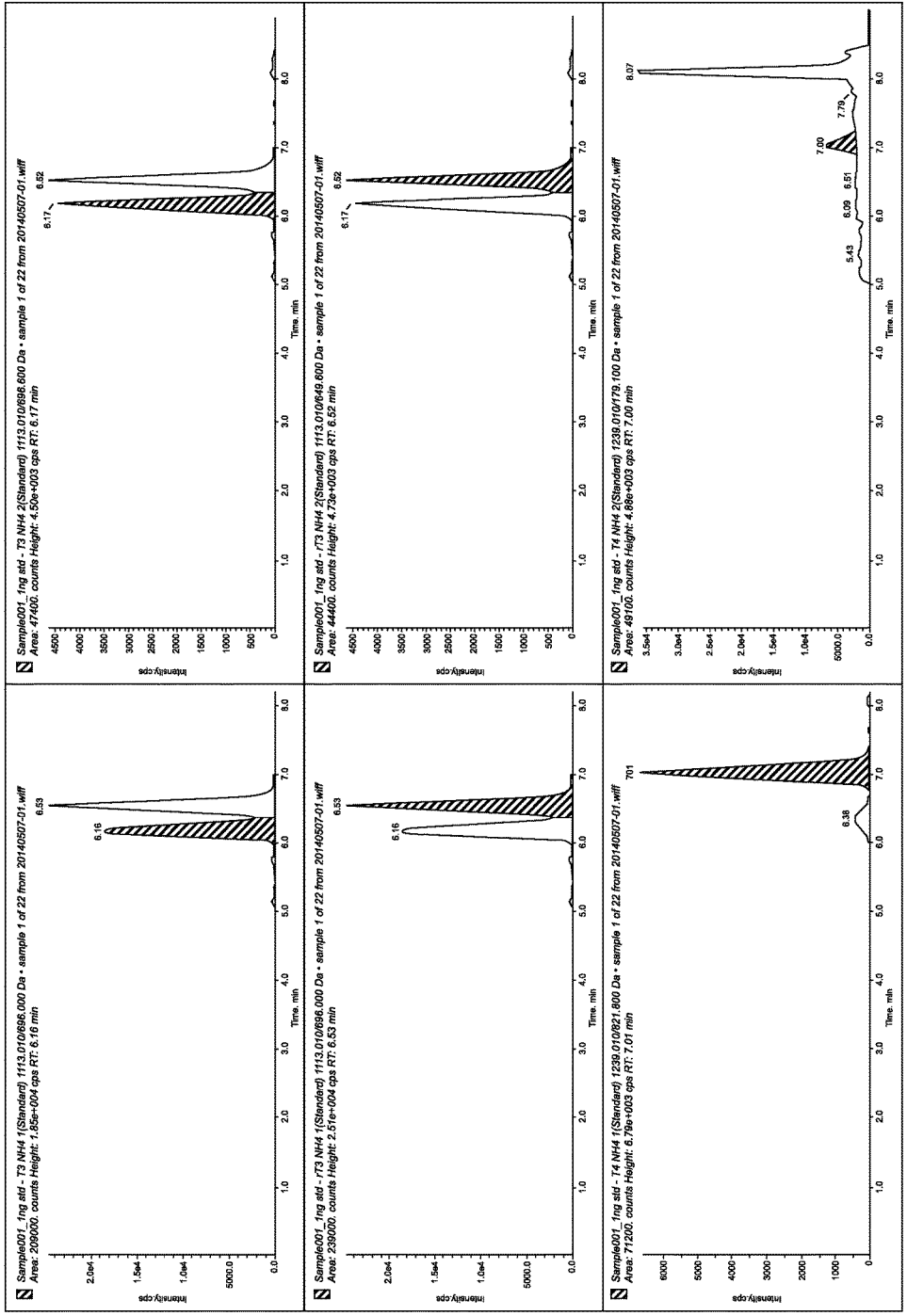
FIGS. 5A, 5B, 5C, and 5D provide the various peaks at each shift for the Thyroid hormones: plasma with 5 ng/ml equivalent (FIG. 5A), plasma blank (FIG. 5B), plasma 1 ng/ml (FIG. 5C), and 200 µL BSA with 1 ng/ml (FIG. 5D).
Figure 5B:
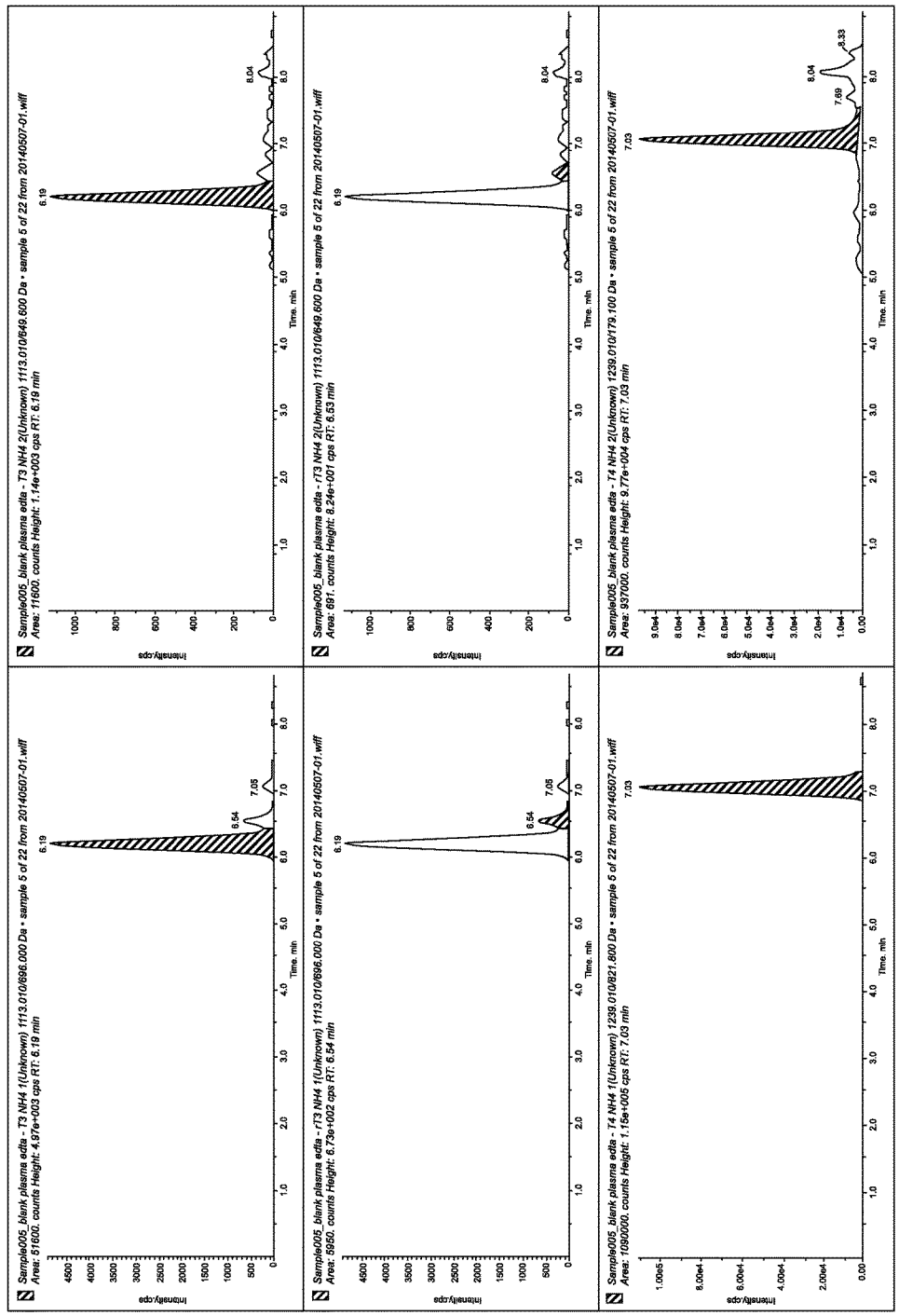
Figure 5C:
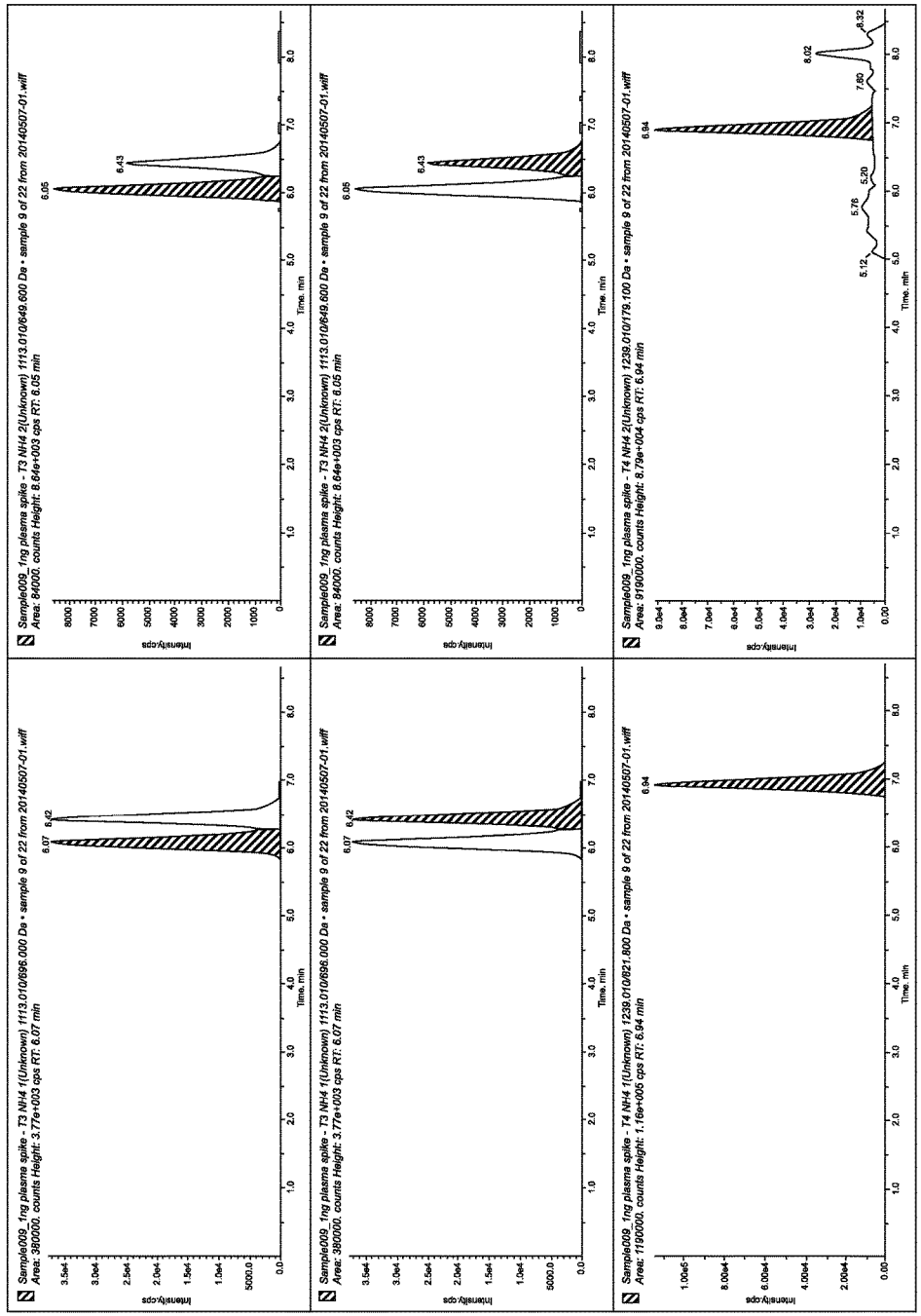
Figure 5D:
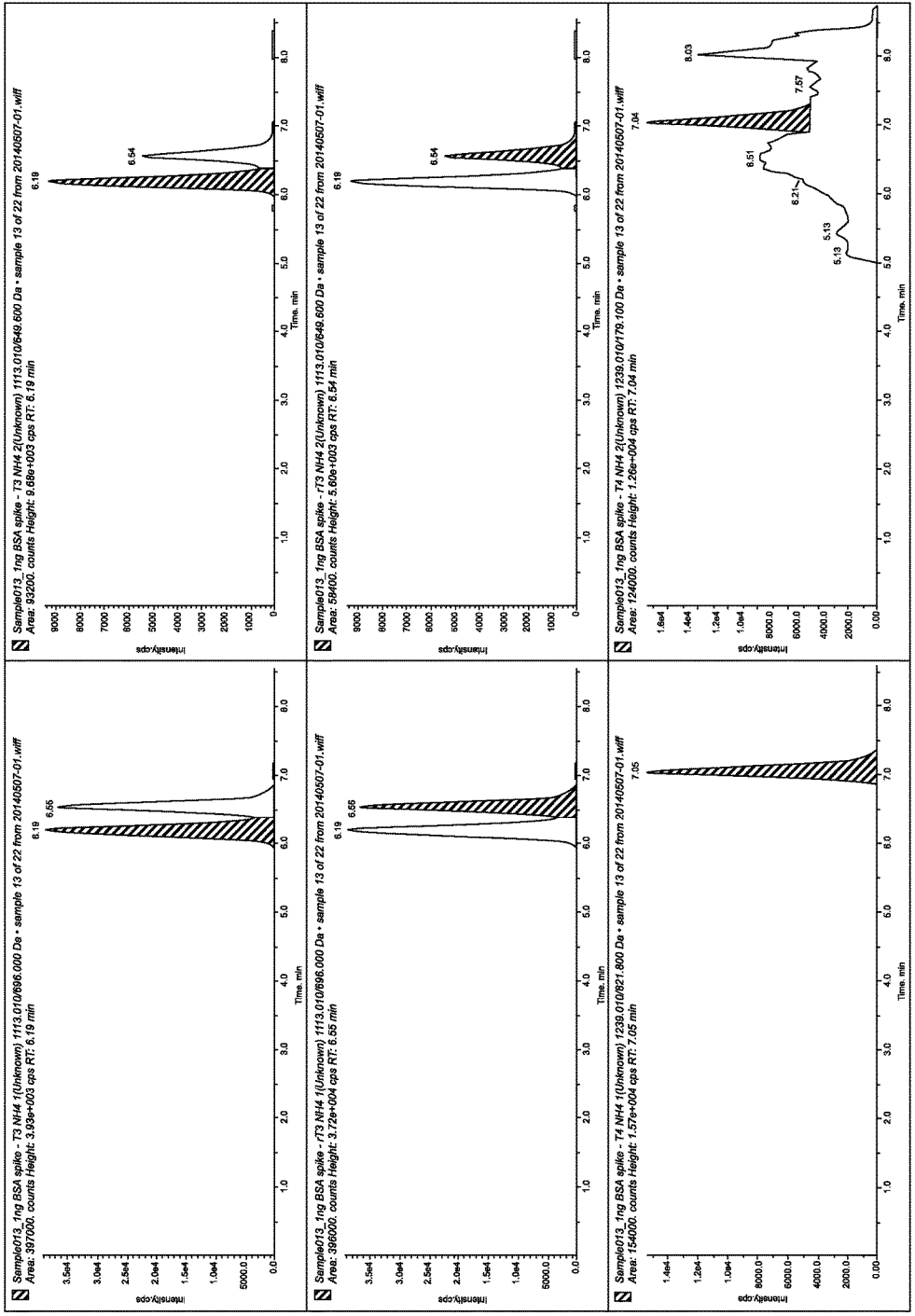
Figure 6A:
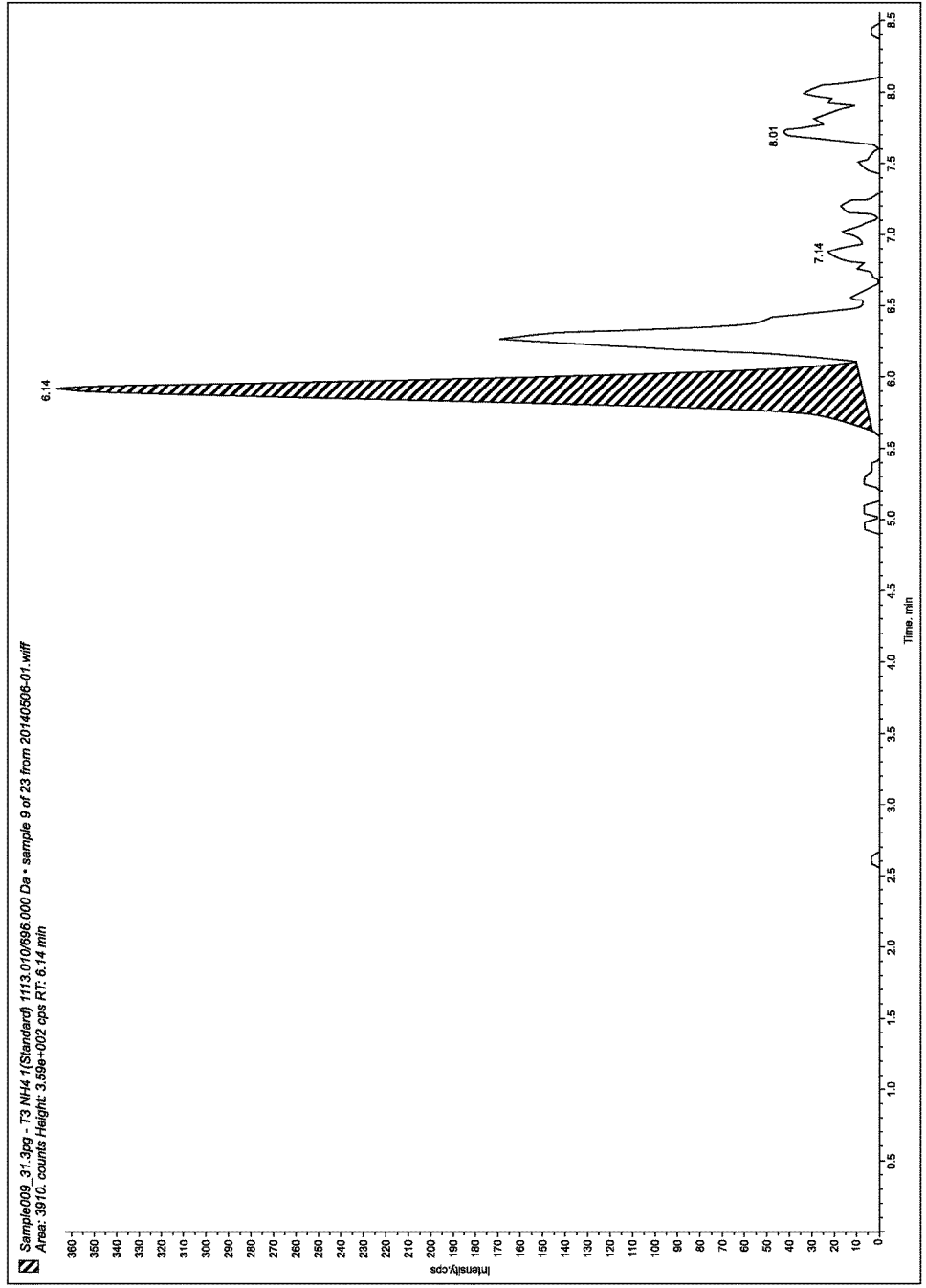
FIGS. 6A, 6B, and 6C provide data for each of the thyroid hormones T3 at 31.3 pg/ml (FIG. 6A), rT3 at 31.3 pg/mL (FIG. 6B), and T4 at 31.3 pg/ml (FIG. 6C).
Figure 6B:
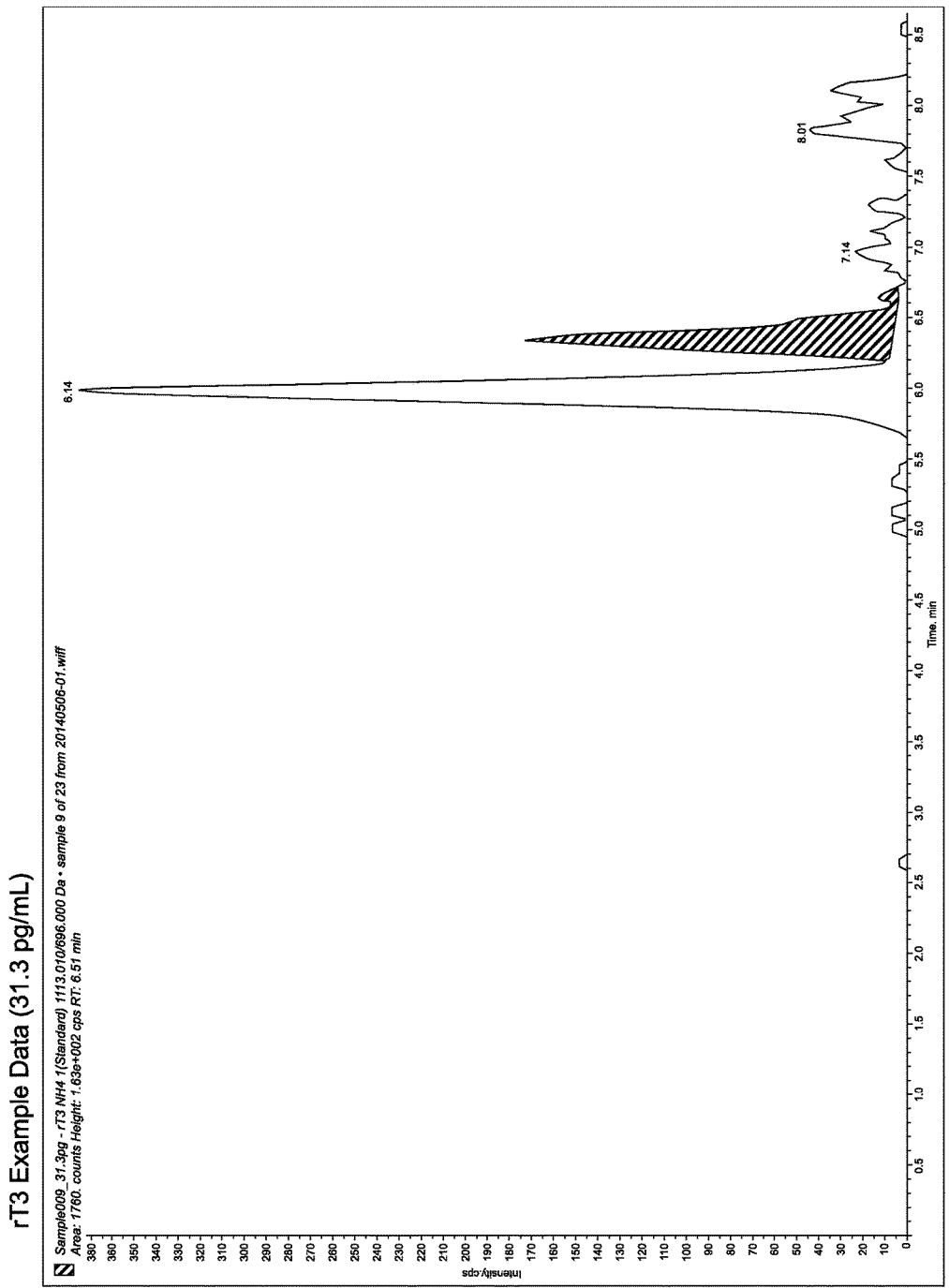
Figure 6C:
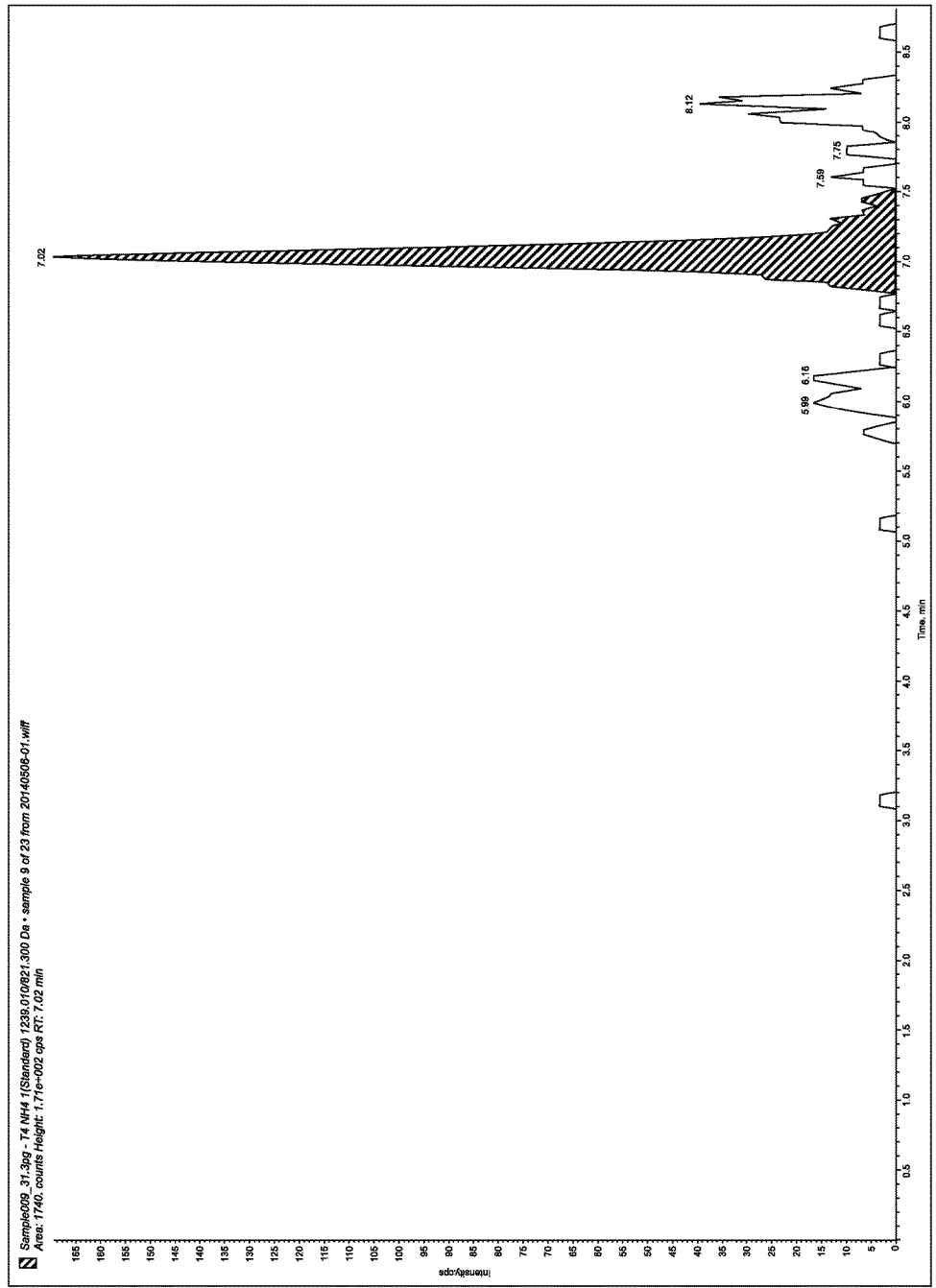

FIGS. 2A and 2B represent data obtained at 10 and 100 pg/ml. However, all concentrations were read, with two plasma samples each, and each sample being read in duplicate. The data summarized in Table 4 provide exemplary linearity regression data for the quantification of dopamine, Epinephrine and Norepinephrine in plasma.

TABLE 4

| Analyte | Extraction Efficiency (%)[1] | LLOQ | Linear Range | Mean C.V.[2] | Mean R^2[3] |
|---|---|---|---|---|---|
| Dopamine | 111.3 | 10 pg/ml | 10 pg/ml-100 ng/ml | 7.2 | 0.9983 |
| Epinephrine | 99 | 10 pg/ml | 10 pg/ml-100 ng/ml | 10.2 | 0.9989 |
| Norepinephrine | 82.5 | 10 pg/ml | 10 pg/ml-100 ng/ml | 8.8 | 0.9985 |

[1]Average Extraction Efficiency of Dopamine 837 > 180 & 837 > 137, Epinephrine 867 > 298 & 867 > 166, & Norepinephrine 853 > 196 & 853 > 152
[2]C.V. of Triplicates from Recovery Data (average for both ions)
[3]Quadratic Regression (1/x weighing) of Standard Curve

Example 2 Quantification of Metanephrines in Blood Plasma Metanephrines Method and Example Data Plasma samples were obtained from human patients' blood. Samples were drawn (plasma sodium heparin & EDTA) into pre-chilled Vacutainers. Vacutainers were inverted 5× and refrigerated until centrifuged. Plasma was separated in a refrigerated centrifuge (1000×g for 10 minutes) within 30 minutes of collection and then frozen immediately at −20° C. in plastic vials. Plasma was thawed and diluted before use in solid phase extraction. The blanks, calibration samples, and plasma samples were spiked with internal standards. Standard curves were generated with plasma solutions spiked with a known amount of metanephrine. The spiking solution was serially diluted before being added to the plasma taken from the same plasma sample.

CEREX® PWCX, 1 cc 10 mg, 96/pk (catalog number 675-0101R) were conditioned with 0.5 ml of methanol, followed by 0.5 ml of 10 mM Phosphate Buffer pH 6.8. 0.5 ml 10 mM Phosphate buffer was mixed with 100 μL of the Sample. Another 0.5 ml 10 mM Phosphate Buffer at pH 6.8 was added to the column. The Sample/buffer mix was loaded onto the column at a pressure of 2-3 psi. The column was washed with 1 ml deionized water at 2-3 psi and subsequently washed with 1 ml Acetonitrile at 6 psi. The sample was eluted from the column with 0.5 ml of Elution Buffer; 20 μl of 100 mg/ml FMOC-Cl in a 50:50 solution of 100 mM $K_2CO_3$:acetonitrile. The derivatization reaction was permitted to proceed for 12 minutes at room temperature. The derivatization reaction was stopped with 20 μL of 20:80 50 mM NH4CO3H:Acetonitrile. 25 μL of the solution obtained from the ammonium formate reaction was used directly as the sample injected in the LC-MS/MS analysis.

For LC-MS/MS analysis, 25 μL of the solution obtained from the ammonium formate reaction was automatically injected into a TARGA® C18 3 μm particle size 50×2.1 mm analytical column. A binary HPLC gradient was applied to the analytical column to separate the metanephrines from other analytes contained in the sample. Mobile phase A was 5.0 mM ammonium formate with 0.1% formic acid pH 3.0 and mobile phase B was Acetonitrile with 0.1% formic acid. The HPLC gradient proceeded at a temperature of 35° C. with a flow rate of 500 μl/min over five minutes as follows: 0.01 min, 50% B; 3.0 min, 100% B, 4.0 min 100% B, 4.5 min, 50% B, 5.0 min, 50% B.

MS/MS was performed using an API 5000 triple quadrupole mass spectrometer controlled by Analyst Software Version 1.52 (ABI-SCIEX, Toronto, Canada). Analyte exiting the HPLC analytical column through the mobile phase flowed to the heated nebulizer interface of the MS/MS analyzer. The solvent/analyte mixture was converted to vapor in the heated tubing of the interface. Analytes in the nebulized solvent were ionized by heated Electrospray Ionization source.

Ions passed to the first quadrupole (Q1), which selected ions with a mass to charge ratio of parent ions generated from one of the analytes. Ions entering quadrupole 2 (Q2) collided with argon gas to generate ion fragments, which were passed to quadrupole 3 (Q3) for further selection. After measurement of ions indicative of one of the analytes, Q1 was adjusted so that ions with a mass to charge ratio of parent ion from a second analyte were selected. These ions were collided with argon gas in Q2, and the ion fragments passed to Q3 for further selection. The following mass transitions were used for detection and quantitation of the metanephrines during validation on positive polarity from the same sample injection.

TABLE 5

| Ions Monitored | | | |
|---|---|---|---|
| Compound | Polarity | Precursor m/z | Product m/z |
| Metanephrine | (+) | 659.2* | 268.4* |
| | (+) | 659.2 | 624.3 |
| | (+) | 659.2 | 179.1 |
| | (+) | 659.2 | 642.5 |
| | (+) | 659.2 | 180.1 |
| | (+) | 659.2 | 178 |
| | (+) | 659.2* | 446.5* |
| | (+) | 659.2 | 224.3 |
| | (+) | 659.2 | 165 |
| Normetanephrine | (+) | 645.1* | 166.1* |
| | (+) | 645.1 | 210.2 |
| | (+) | 645.1* | 254.3* |
| | (+) | 645.1 | 178 |
| | (+) | 645.1 | 179 |
| | (+) | 645.1 | 149.3 |
| | (+) | 645.1 | 121.2 |
| | (+) | 645.1 | 134 |
| | (+) | 645.1 | 106 |

TABLE 6

| Recovery Data | | | |
|---|---|---|---|
| Sample | Analyte | Analyte Peak Area (counts) | % Recovery |
| Standard | Metanephrine 659 > 268 | 1860000 | |
| Elution - Rep 1 | | 1850000 | 99.5 |
| Elution - Rep 2 | | 1700000 | 91.4 |
| Standard | Metanephrine 659 > 446 | 1370000 | |
| Elution - Rep 1 | | 1190000 | 86.9 |
| Elution - Rep 2 | | 1130000 | 82.5 |
| Standard | Normetanephrine 645 > 166 | 1580000 | |
| Elution - Rep 1 | | 1520000 | 96.2 |
| Elution - Rep 2 | | 1570000 | 99.4 |
| Standard - Rep 1 | Normetanephrine 645 > 254 | 1300000 | |
| Standard - Rep 2 | | 1380000 | 106.2 |
| Standard - Rep 3 | | 1450000 | 111.5 |

Again, the percent recovery was very high, as shown by Table 6. FIGS. 4A-4D show the spectra for the metanephrines.

Example 3 Quantification of Thyroid Hormones in Blood Plasma Thyroid Hormones (T3, rT3, T4) Method and Example Data Sample preparation was done as in Example 1, except that samples were spiked with thyroid hormones and appropriate internal standards.

CEREX® PSCX 1cc 10 mg (catalog number 687-0101R, 96/pk) columns were conditioned with 1.0 mL of methanol, followed by 1.0 mL of 2% formic acid (aqueous). 0.5 mL of 13% acetonitrile in 2% Formic Acid (aq.) was mixed with 200 µL of the Sample. 0.5 mL of 13% acetonitrile in 2% Formic Acid was added to the column. The Sample/buffer mix was loaded onto the column at a pressure of 2-3 psi. The column was washed with 1 ml 50% acetonitrile (aqueous) at 3 psi and subsequently washed with 1 ml Acetonitrile at 6 psi. Columns were dried for 30 seconds with a stream of nitrogen at high pressure. The columns were washed with 1 ml 10 mM potassium carbonate pH 11.9, at 3 psi.

The sample was eluted from the column with 0.5 ml of elution buffer [100 mM potassium carbonate (aq., pH 11.9): Acetonitrile], 20 µL of 100 mg/ml FMOC-Cl in acetonitrile was added post elution. The derivatization reaction was permitted to proceed for 25 minutes at room temperature. The derivatization reaction was stopped with 20 µL of 20:80 50 mM $NH_4CO_3H$ (aq.): Acetonitrile. This reaction mixture was used directly for quantification without further treatment For LC-MS/MS analysis, 20 µL of the solution of the derivatization reaction mixture was injected into a TARGA® C18 3 µm particle size 50×2.1 mm analytical column. A binary HPLC gradient was applied to the analytical column to separate the thyroid hormones from other analytes contained in the sample. Mobile phase A was 20.0 mM ammonium formate pH 3.0 and mobile phase B was Acetonitrile with 0.1% formic acid. The HPLC gradient proceeded at a temperature of 40° C. with a flow rate of 500 µl/min over five minutes as follows: 0.01 min, 60% B; 7.5 min, 85% B, 7.6 min, 95% B; 7.9 min, 95% B, 8.0 min, 60% B; 9.0 min, 60% B.

MS/MS was performed using an API 5000 triple quadrupole mass spectrometer controlled by Analyst Software Version 1.52 (ABI-SCIEX, Toronto, Canada). Analyte exiting the HPLC analytical column through the mobile phase flowed to the heated nebulizer interface of the MS/MS analyzer. The solvent/analyte mixture was converted to vapor in the heated tubing of the interface. Analytes in the nebulized solvent were ionized by heated Electrospray Ionization source.

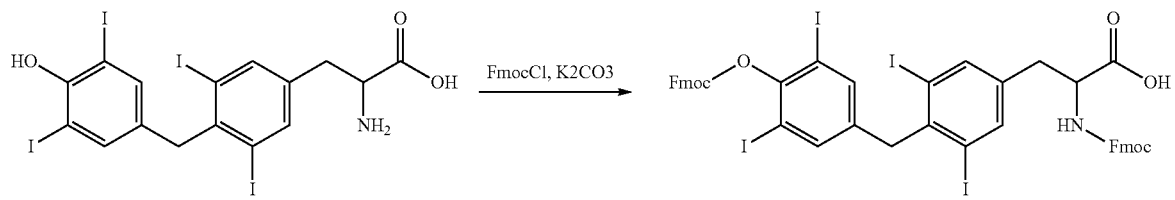

Thyroxine, T4
Chemical Formula: $C_{16}H_{13}I_4NO_3$
Exact Mass: 774.71

BisFmoc thyroxine [$T_4(Fmoc)_2$]
Chemical Formula: $C_{46}H_{33}I_4NO_7$
Exact Mass: 1218:84

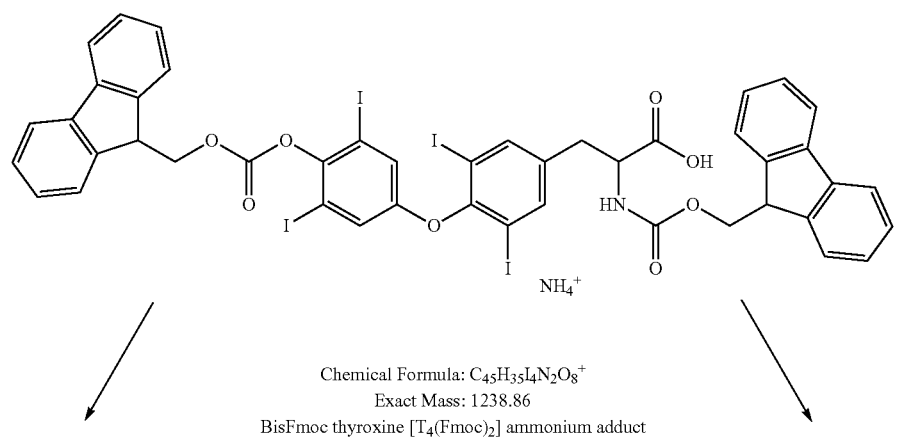

Chemical Formula: $C_{45}H_{35}I_4N_2O_8^+$
Exact Mass: 1238.86
BisFmoc thyroxine [$T_4(Fmoc)_2$] ammonium adduct

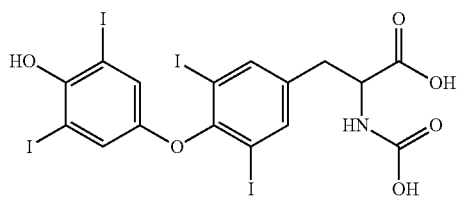

Chemical Formula: $C_{16}H_{11}I_4NO_6$
Exact Mass: 820.68

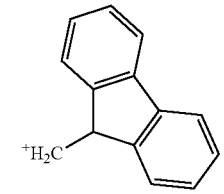

Chemical Formula: $C_{14}H_{11}^+$
Exact Mass: 179.09

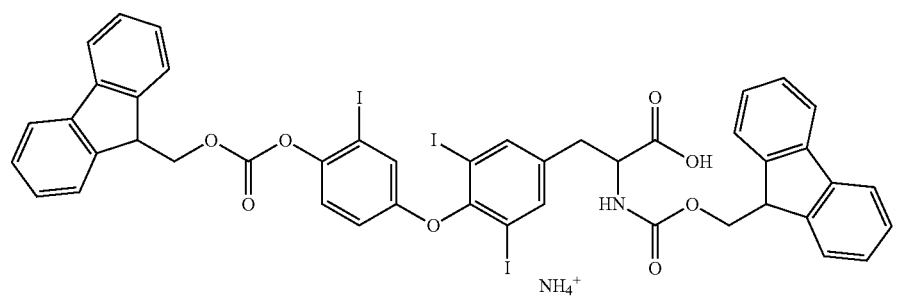

Chemical Formula: $C_{45}H_{36}I_3N_2O_8^+$
Exact Mass: 1112.96
BisFmoc 3,5,3'-triiodothyronine [T3(Fmoc)2] ammonium adduct

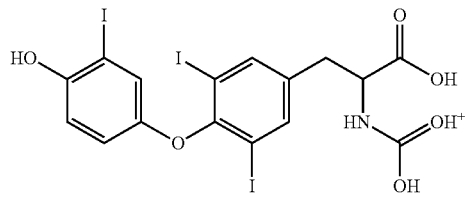

Chemical Formula: $C_{16}H_{13}I_3NO_6^+$
Exact Mass: 695.79

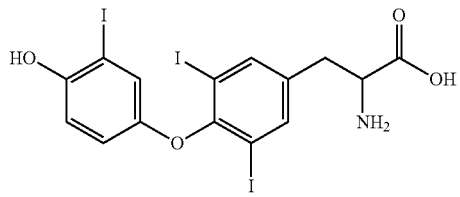

Chemical Formula: $C_{15}H_{12}I_3NO_4$
Exact Mass: 650.79

Ions passed to the first quadrupole (Q1), which selected ions with a mass to charge ratio of parent ions generated from one of the analytes. Ions entering quadrupole 2 (Q2) collided with argon gas to generate ion fragments, which were passed to quadrupole 3 (Q3) for further selection. After measurement of ions indicative of one of the analytes, Q1 was adjusted so that ions with a mass to charge ratio of parent ion from a second analyte were selected. These ions were collided with argon gas in Q2, and the ion fragments passed to Q3 for further selection. The following mass transitions were used for detection and quantitation of the thyroid hormones during validation on positive polarity from the same sample injection.

TABLE 7

Ions Monitored

| Compound | Polarity | | Precursor m/z | Product m/z |
|---|---|---|---|---|
| Triiodothyronine (T3) | (+) | Quantitative | 1113 | 696 |
| | (+) | Confirmatory | 1113 | 649.6 |
| Thyroxine (T4) | (+) | Quantitative | 1239 | 821 |
| | (+) | Confirmatory | 1239 | 179.1 |
| Reverse triiodothyronine (rT3) | (+) | Quantitative | 1113 | 696 |
| | (+) | Confirmatory | 1113 | 649.6 |
| 3,3',5-Triiodo-L-thyronine-$^{13}C_6$ (T3-$^{13}C_6$) | (+) | Quantitative | 1118.9 | 701.8 |
| | (+) | Confirmatory | 1118.9 | 655.9 |

TABLE 8

Absolute Recovery: 5 ng/ml in Plasma & BSA

| Sample | Analyte | Analyte Peak Area (counts) | IS Peak Area (counts) | Area Ratio | Mean (Area Ratio) | SD (Area Ratio) | % C.V. (Area Ratio) | % Recovery |
|---|---|---|---|---|---|---|---|---|
| Standard - Rep 1 | rT3 | 239000 | 314000 | 0.761 | 0.726 | 0.0317 | 4.4 | |
| Standard - Rep 2 | | 316000 | 454000 | 0.697 | | | | |
| Standard - Rep 3 | | 376000 | 506000 | 0.744 | | | | |
| Standard - Rep 4 | | 344000 | 491000 | 0.701 | | | | |
| Blank Plasma - Rep 1 | | 5950 | 490000 | 0.0121 | 0.013 | 0.0007 | 5.7 | |
| Blank Plasma - Rep 2 | | 5240 | 402000 | 0.0131 | | | | |
| Blank Plasma - Rep 3 | | 5040 | 430000 | 0.0117 | | | | |
| Blank Plasma - Rep 4 | | 5750 | 440000 | 0.0131 | | | | |
| Spiked Plasma - Rep 1 | | 381000 | 480000 | 0.794 | 0.839 | 0.0334 | 4.0 | 113.8 |
| Spiked Plasma - Rep 2 | | 361000 | 434000 | 0.832 | | | | |
| Spiked Plasma - Rep 3 | | 379000 | 437000 | 0.867 | | | | |
| Spiked Plasma - Rep 4 | | 374000 | 434000 | 0.861 | | | | |
| Spiked BSA - Rep 1 | | 396000 | 562000 | 0.705 | 0.648 | 0.0473 | 7.3 | 89.3 |
| Spiked BSA - Rep 2 | | 341000 | 536000 | 0.635 | | | | |
| Spiked BSA - Rep 3 | | 318000 | 537000 | 0.592 | | | | |
| Spiked BSA - Rep 4 | | 343000 | 519000 | 0.661 | | | | |
| Standard - Rep 1 | T3 | 209000 | 314000 | 0.665 | 0.779 | 0.0759 | 9.8 | |
| Standard - Rep 2 | | 367000 | 454000 | 0.808 | | | | |
| Standard - Rep 3 | | 416000 | 506000 | 0.822 | | | | |
| Standard - Rep 4 | | 402000 | 491000 | 0.819 | | | | |
| Blank Plasma - Rep 1 | | 51600 | 490000 | 0.105 | 0.107 | 0.0040 | 3.7 | |
| Blank Plasma - Rep 2 | | 42300 | 402000 | 0.105 | | | | |
| Blank Plasma - Rep 3 | | 48500 | 430000 | 0.113 | | | | |
| Blank Plasma - Rep 4 | | 46400 | 440000 | 0.105 | | | | |
| Spiked Plasma - Rep 1 | | 380000 | 480000 | 0.791 | 0.816 | 0.0261 | 3.2 | 91.0 |
| Spiked Plasma - Rep 2 | | 370000 | 434000 | 0.852 | | | | |
| Spiked Plasma - Rep 3 | | 352000 | 437000 | 0.805 | | | | |
| Spiked Plasma - Rep 4 | | 353000 | 434000 | 0.814 | | | | |
| Spiked BSA - Rep 1 | | 397000 | 562000 | 0.706 | 0.716 | 0.0198 | 2.8 | 91.9 |
| Spiked BSA - Rep 2 | | 399000 | 536000 | 0.744 | | | | |
| Spiked BSA - Rep 3 | | 375000 | 537000 | 0.699 | | | | |
| Spiked BSA - Rep 4 | | 370000 | 519000 | 0.713 | | | | |
| Standard - Rep 1 | T4 | 71200 | 314000 | 0.227 | 0.241 | 0.0141 | 5.8 | |
| Standard - Rep 2 | | 109000 | 454000 | 0.24 | | | | |
| Standard - Rep 3 | | 119000 | 506000 | 0.235 | | | | |
| Standard - Rep 4 | | 127000 | 491000 | 0.26 | | | | |
| Blank Plasma - Rep 1 | | 1090000 | 490000 | 2.23 | 2.343 | 0.1422 | 6.1 | |
| Blank Plasma - Rep 2 | | 1030000 | 402000 | 2.55 | | | | |
| Blank Plasma - Rep 3 | | 990000 | 430000 | 2.31 | | | | |
| Blank Plasma - Rep 4 | | 1000000 | 440000 | 2.28 | | | | |
| Spiked Plasma - Rep 1 | | 1190000 | 480000 | 2.48 | 2.640 | 0.1826 | 6.9 | 123.7 |
| Spiked Plasma - Rep 2 | | 1140000 | 434000 | 2.62 | | | | |
| Spiked Plasma - Rep 3 | | 1120000 | 437000 | 2.56 | | | | |
| Spiked Plasma - Rep 4 | | 1260000 | 434000 | 2.9 | | | | |
| Spiked BSA - Rep 1 | | 154000 | 562000 | 0.274 | 0.275 | 0.0168 | 6.1 | 114.3 |
| Spiked BSA - Rep 2 | | 142000 | 536000 | 0.264 | | | | |
| Spiked BSA - Rep 3 | | 160000 | 537000 | 0.299 | | | | |
| Spiked BSA - Rep 4 | | 137000 | 519000 | 0.263 | | | | |

Note:
Average blank plasma area ration subtracted from spiked plasma area ratio before recovery was calculated.

FIGS. 5A-5D and FIGS. 6A-6C provide exemplary spectra for the thyroid hormones. Table 9 provide exemplary linear regression data for quantification of thyroid hormones.

TABLE 9

Linearity - 33.1 pg/ml > 2 ng/ml in BSA

| Sample | Analyte Peak Area (counts) | IS Peak Area (counts) | Area Ratio | Calc. Conc. (pg/mL) | $R^2$[1] |
|---|---|---|---|---|---|
| T3 31.3 pg/ml Rep 1 | 3,660 | 956,000 | 0.00383 | 23 | 0.9994 |
| T3 31.3 pg/ml Rep 2 | 3,910 | 1,240,000 | 0.00314 | 11.9 | |
| T3 62.5 pg/ml Rep 1 | 7,500 | 1,420,000 | 0.00528 | 46.6 | |
| T3 62.5 pg/ml Rep 2 | 5,720 | 998,000 | 0.00574 | 54 | |
| T3 125 pg/ml Rep 1 | 9,740 | 1,030,000 | 0.0095 | 115 | |

TABLE 9-continued

Linearity - 33.1 pg/ml > 2 ng/ml in BSA

| Sample | Analyte Peak Area (counts) | IS Peak Area (counts) | Area Ratio | Calc. Conc. (pg/mL) | $\hat{R}2^1$ |
|---|---|---|---|---|---|
| T3 125 pg/ml Rep 2 | 9,610 | 916,000 | 0.0105 | 131 | |
| T3 250 pg/ml Rep 1 | 18,800 | 1,000,000 | 0.0188 | 266 | |
| T3 250 pg/ml Rep 2 | 20,700 | 1,150,000 | 0.018 | 254 | |
| T3 500 pg/ml Rep 1 | 36,300 | 1,020,000 | 0.0357 | 541 | |
| T3 500 pg/ml Rep 2 | 34,500 | 1,050,000 | 0.0328 | 494 | |
| T3 1 ng/ml Rep 1 | 64,400 | 1,010,000 | 0.0635 | 993 | |
| T3 1 ng/ml Rep 2 | 69,100 | 1,060,000 | 0.0655 | 1030 | |
| T3 2 ng/ml Rep 1 | 103,000 | 843,000 | 0.122 | 1940 | |
| T3 2 ng/ml Rep 2 | 116,000 | 912,000 | 0.127 | 2040 | |
| rT3 31.3 pg/ml Rep 1 | 1,060 | 956,000 | 0.00111 | 24.1 | 0.9935 |
| rT3 31.3 pg/ml Rep 2 | 1,760 | 1,240,000 | 0.00142 | 31.6 | |
| rT3 62.5 pg/ml Rep 1 | 3,400 | 1,420,000 | 0.00239 | 55.2 | |
| rT3 62.5 pg/ml Rep 2 | 3,530 | 998,000 | 0.00354 | 83.1 | |
| rT3 125 pg/ml Rep 1 | 5,380 | 1,030,000 | 0.00525 | 124 | |
| rT3 125 pg/ml Rep 2 | 4,890 | 916,000 | 0.00534 | 127 | |
| rT3 250 pg/ml Rep 1 | 11,400 | 1,000,000 | 0.0114 | 273 | |
| rT3 250 pg/ml Rep 2 | 10,300 | 1,150,000 | 0.00902 | 216 | |
| rT3 500 pg/ml Rep 1 | 22,900 | 1,020,000 | 0.0225 | 543 | |
| rT3 500 pg/ml Rep 2 | 22,200 | 1,050,000 | 0.0211 | 509 | |
| rT3 1 ng/ml Rep 1 | 40,700 | 1,010,000 | 0.0401 | 970 | |
| rT3 1 ng/ml Rep 2 | 41,700 | 1,060,000 | 0.0395 | 956 | |
| rT3 2 ng/ml Rep 1 | 76,700 | 843,000 | 0.091 | 2200 | |
| rT3 2 ng/m Rep 2 | 68,500 | 912,000 | 0.0751 | 1820 | |
| T4 31.3 pg/ml Rep 1 | 1,550 | 956,000 | 0.00162 | 37.7 | 0.9966 |
| T4 31.3 pg/ml Rep 2 | 1,740 | 1,240,000 | 0.0014 | 28.2 | |
| T4 62.5 pg/ml Rep 1 | 2,700 | 1,420,000 | 0.0019 | 49.7 | |
| T4 62.5 pg/ml Rep 2 | 2,240 | 998,000 | 0.00224 | 64.1 | |
| T4 125 pg/ml Rep 1 | 4,390 | 1,030,000 | 0.00428 | 152 | |
| T4 125 pg/ml Rep 2 | 3,670 | 916,000 | 0.004 | 140 | |
| T4 250 pg/ml Rep 1 | 7,030 | 1,000,000 | 0.007 | 268 | |
| T4 250 pg/ml Rep 2 | 7,660 | 1,150,000 | 0.00668 | 254 | |
| T4 500 pg/ml Rep 1 | 12,900 | 1,020,000 | 0.0127 | 512 | |
| T4 500 pg/ml Rep 2 | 12,500 | 1,050,000 | 0.0119 | 477 | |
| T4 1 ng/ml Rep 1 | 23,800 | 1,010,000 | 0.0234 | 972 | |
| T4 1 ng/ml Rep 2 | 24,000 | 1,060,000 | 0.0228 | 943 | |
| T4 2 ng/ml Rep 1 | 43,000 | 843,000 | 0.051 | 2150 | |
| T4 2 ng/ml Rep 2 | 40,900 | 912,000 | 0.0448 | 1890 | |
| T3 62.5 pg/ml Rep 2 | 5,720 | 998,000 | 0.00574 | 54 | |

[1]Quadratic Regression (1/x weighing) of Standard Curve

Example 4 Derivatized THC

The presently recited methods were also performed on THC. The THC was derivatized during elution from the SPE column as follows:

Quantification of
11-nor-9-carboxy-delta-9-tetrahydrocannabinol in
Urine Method and Example Data Urine hydrolysis: Combine urine sample (2 mL) with KOH (aq., 10M, 100 uL) at 60° C. for 15 min, add IS, and allow to cool to room temperature. Centrifuge at 2000 rpm for 2 minutes. The clear solution was taken to the next step.

Solid phase extraction column [narrow bore backed with sorbent (10BPC—SAX, 2.5 mg)] was equilibrated with methanol (0.5 mL) & a washing buffer ($H_2O$:Acetonitrile:$NH_4OH$=85:15:1, 0.5 mL). Hydrolyzed urine sample (previous step, 0.5 mL) was added and passed through the column in 2 min under a nitrogen pressure (<15 psi). The column was washed sequentially with the washing buffer ($H_2O$:Acetonitrile:$NH_4OH$=85:15:1, 0.5 mL), methanol (0.5 mL), ethyl acetate, then dried under a nitrogen stream at 30 psi for 3 min. The analyte is then eluted with the elution buffer [hexane:ethyl acetate:acetic acid (Glacial)=80:18:2, 100 µL], and dried under a nitrogen stream (40° C.).

Resuspend the dried extracted analyte with Fluorenylmethyloxycarbonyl chloride (FMOC-Cl, 1.6 mg/mL in ACN, 50 µL), vortexed, then, potassium carbonate (aq., 100 mM, 50 µl) was added, vortexed. Reaction was allowed for 25 minutes, then suspended with a stopping buffer [$NH_4CO_3H$ (aq., 50 mM):acetonitrile=1:4, 10 µL].

For LC-MS/MS analysis, 20 µL of the solution of the derivatization reaction mixture was injected into a TARGA® C18 3 µm particle size 50×2.1 mm analytical column. A binary HPLC gradient was applied to the analytical column to separate the thyroid hormones from other analytes contained in the sample. Mobile phase A was 20.0 mM ammonium formate pH 3.0 and mobile phase B was Acetonitrile with 0.1% formic acid. The HPLC gradient proceeded at a temperature of 40° C. with a flow rate of 500 µl/min over five minutes as follows: 0.01 min, 40% B; 3.0 min, 90% B; 4.0 min, 90% B; 4.1 min, 40% B, 5.0 min, 40% B.

MS/MS was performed using an API 5000 triple quadrupole mass spectrometer controlled by Analyst Software Version 1.52 (ABI-SCIEX, Toronto, Canada). Analyte exiting the HPLC analytical column through the mobile phase flowed to the heated nebulizer interface of the MS/MS analyzer. The solvent/analyte mixture was converted to vapor in the heated tubing of the interface. Analytes in the nebulized solvent were ionized by heated Electrospray Ionization source.

Ions passed to the first quadrupole (Q1), which selected ions with a mass to charge ratio of parent ions generated from one of the analytes. Ions entering quadrupole 2 (Q2) collided with argon gas to generate ion fragments, which were passed to quadrupole 3 (Q3) for further selection. After measurement of ions indicative of one of the analytes, Q1 was adjusted so that ions with a mass to charge ratio of parent ion from a second analyte were selected. These ions were collided with argon gas in Q2, and the ion fragments passed to Q3 for further selection. The following mass transitions were used for detection and quantitation of the thyroid hormones during validation on positive polarity from the same sample injection.

TABLE 12

Recovery of Analyte

| Sample Name | Peak Area (counts) | Recovery (%) |
|---|---|---|
| Sample008__1ng std 500ul 50-50ACN 4ul CMOS 700tem | 313000 | — |
| Sample013__1ng spike 500ul 50-50ACN 4ul CMOS 700tem | 267000 | 85.3 |

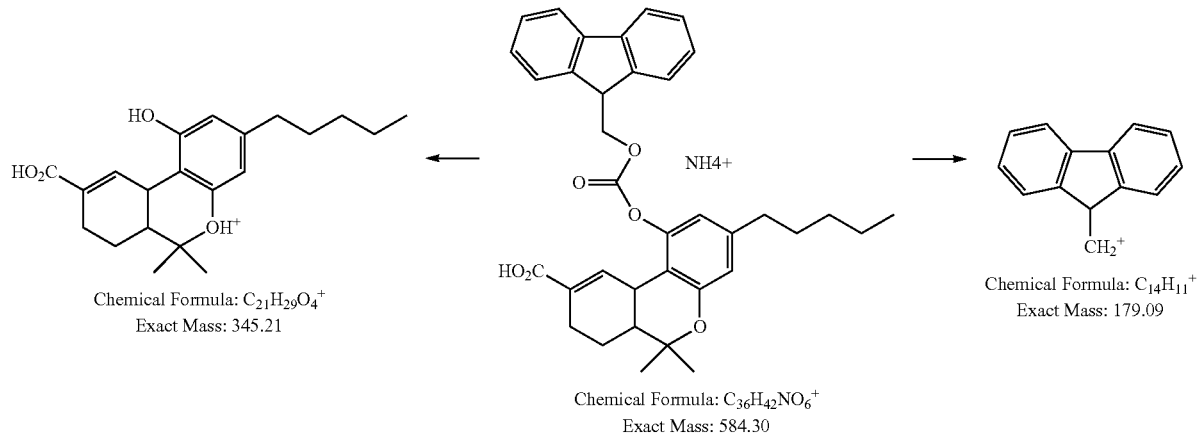

TABLE 10

Ions Monitored

| Compound | Polarity | | Precursor m/z | Product m/z |
|---|---|---|---|---|
| THC-9-Carboxylic acid | (+) | Quantitative | 584.2 | 345.5 |
| | (+) | Confirmatory | 584.2 | 179.3 |

Figure 7A:
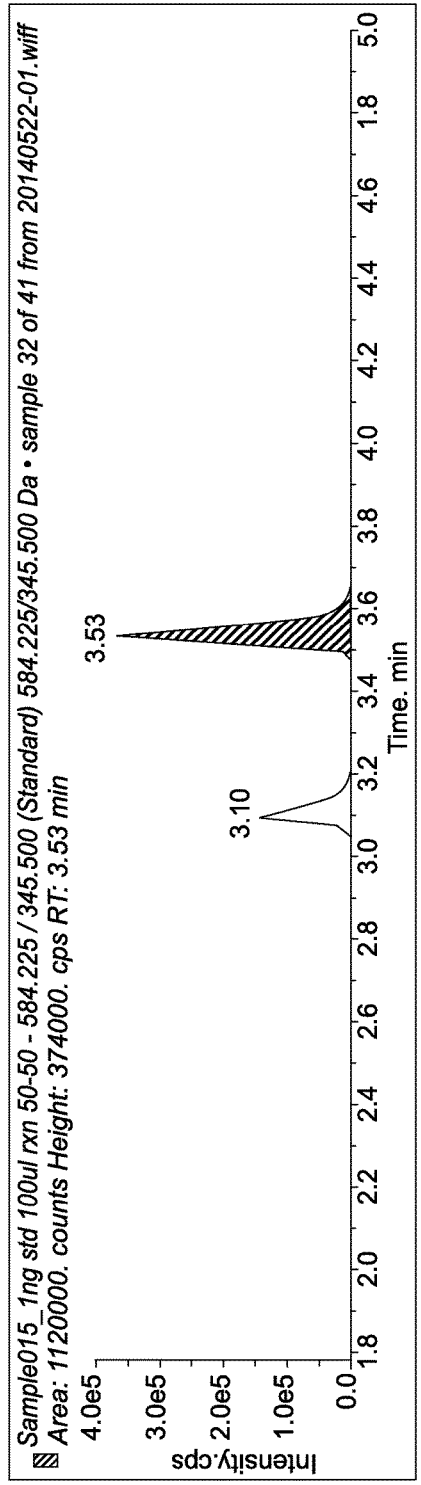
FIGS. 7A, 7B, and 7C provide the linearity data for the quantification of 11-nor-9-carboxy-delta-9-tetrahydrocannabinol in Urine; 1,000 pg/ml (FIG. 7A), 100 pg/ml (FIG. 7B), and 10 pg/ml (FIG. 7C).
Figure 7B:
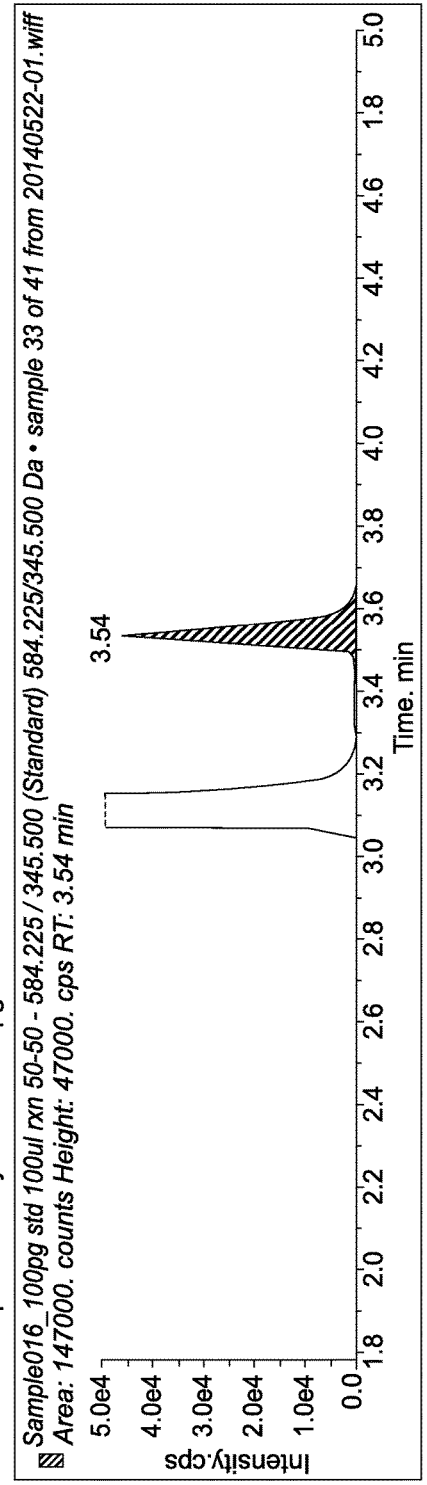
Figure 7C:
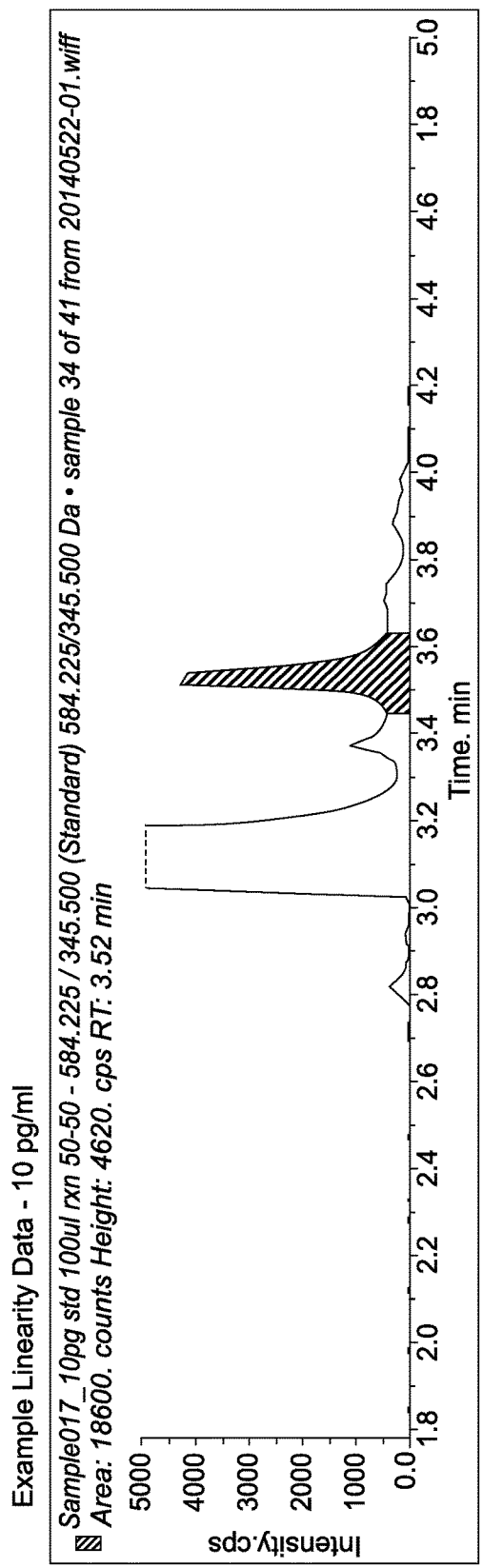

Table 11 shows the quadratic linear regression for of 11-nor-9-carboxy-delta-9-tetrahydrocannabinol in Urine at 10 to 1,000 ng/reactions. FIGS. 7A-7C show the chromatographs of example linearity data at 1000 pq/ml, 100 pq/ml, and 10 pq/ml.

TABLE 11

Linearity

| Sample Name | PeakArea (counts) | Analyte Conc. (pg/mL) | Calculated Conc. (pg/mL) | R^2[1] |
|---|---|---|---|---|
| Sample015__1ng std 100ul rxn 50-50 | 1120000 | 1000 | 1000 | 1.0000 |
| Sample016__100pg std 100ul rxn 50-50 | 147000 | 100 | 100 | |
| Sample017__10pg std 100ul rxn 50-50 | 18600 | 10 | 10 | |

[1]Quadratic Regression (1/x weighing) of Standard Curve

Figure 8A:
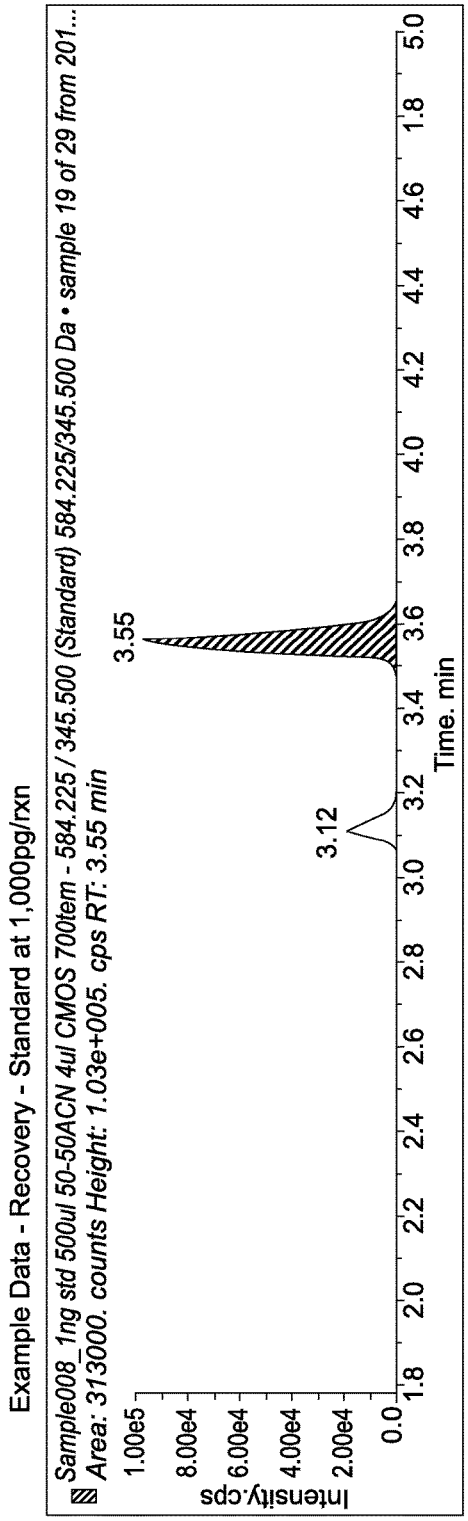
FIGS. 8A and 8B provide recovery data from the quantification of 11-nor-9-carboxy-delta-9-tetrahydrocannabinol in Urine: Recovery-1,000 pg/rxn of Standard (FIG. 8A) and Recovery of 1,000 pg/rxn Extracted Spike (FIG. 8B).
Figure 8B:
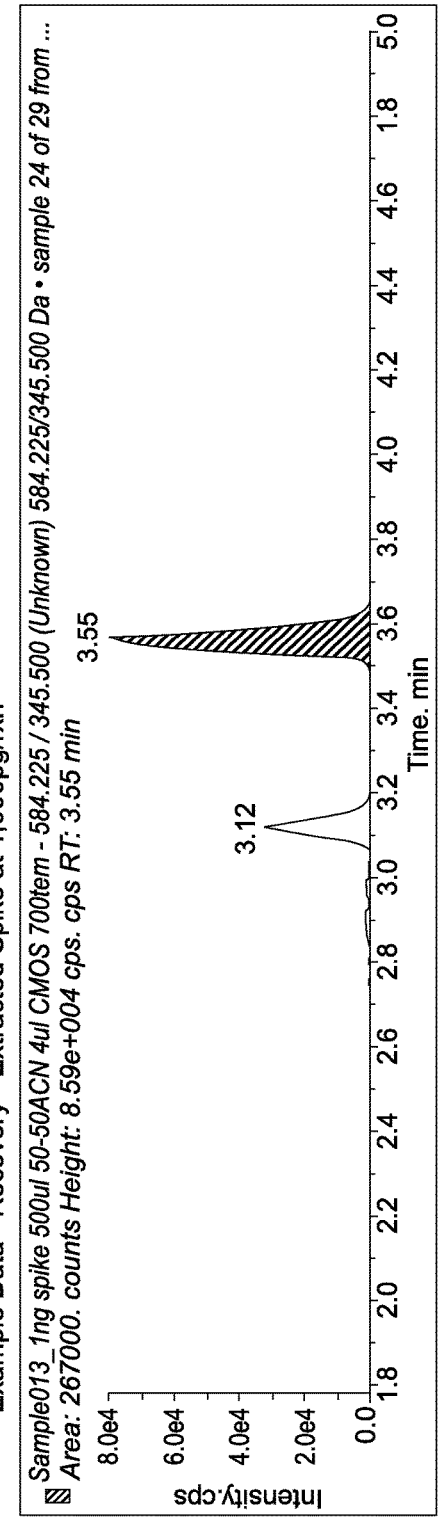

FIGS. 8A (standard) and 8B (the extracted sample) show the chromatogram of the recovery of the analyte. This data is also reflected in Table 12.

In view of the data presented herein, it is clear that the process simultaneously provides following benefits: short sample handling time, automation compatible, chemical protection via derivatization over oxidation, which resulted in high recovery in extraction; improvement in HPLC behavior due to high lipophilicity of the derivatives; and much improved MS/MS sensitivity due to much high molecular weight of the derivative, with LLOQ at 10 pg/mL, i.e. over 1000 fold improvement in quantification sensitivity. These benefits are unexpected in view of the high pH elution, as the stability of catecholamines declines as the pH rises, with destruction becoming extremely rapid in an alkaline medium.

It is also realized that the employment of high MS sensitive derivatization allows one to screen, optimize the process of solid phase extraction, including the choice of sorbent, loading buffer, washing solution, final elution buffer, as well as the process of each step.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit.

At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method for determining the presence of one or more analytes in a test sample, the method comprising: a) solid phase extracting of the one or more analytes from the test sample, wherein an elution buffer comprising a derivatizing agent is added for derivatizing and eluting the one or more analytes in a single step, and b) detecting the one or more derivatized analytes using liquid chromatography and mass spectrometry.

2. The method according to claim 1, wherein the one or more analytes is a compound having a primary amine, a secondary amine, or a phenolic hydroxyl group.

3. The method according to claim 2, wherein the one or more analytes is a monoamine neurotransmitter including catecholamine or one of its derivatives or metabolites, a sex hormone or one of its derivatives or metabolites, a cannabinoid or one of its derivatives or metabolites, a thyroid hormone or one of its derivatives or metabolites, an opiate, opioid or one of its derivatives or metabolites or an arylcyclohexylamine or one of its derivatives or metabolites, an amphetamine or one of its derivatives or metabolites.

4. The method according to claim 1, wherein the test sample is a biological sample, a soil sample, or a sample of food stuff.

5. The method according to claim 1, wherein the derivatizing agent is an acyl halide.

6. The method according to claim 5, wherein the acyl halide is an acyl chloride.

7. The method according to claim 6, wherein the acyl chloride is a compound of Formula II:

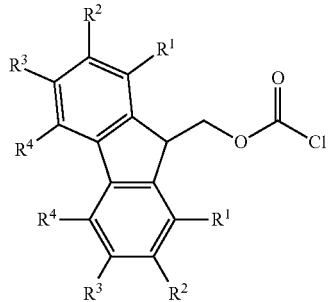

(II)

wherein $R^1$, $R^2$, $R^3$, and $R^4$ are each independently, H, fluorine, chlorine, bromine, iodine, a cyano group, an acetylene group, a propylene group, a vinyl group, a linear $C_{1-8}$ alkyl, a branched $C_{1-8}$ alkyl, a cyclic $C_{1-8}$ alkyl, a substituted vinyl group, a linear $C_{1-8}$ alkoxy, a branched $C_{1-8}$ alkoxy or cyclic $C_{1-8}$ alkoxy.

8. The method according to claim 6, wherein the acyl chloride is one of the following compounds:

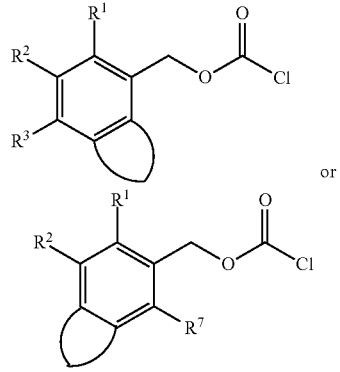

or wherein $R^1$, $R^2$, $R^3$, and $R^7$ are each independently, H, fluorine, chlorine, bromine, iodine, a cyano group, an acetylene group, a propylene group, a vinyl group, a linear $C_{1-8}$ alkyl, a branched $C_{1-8}$ alkyl, a cyclic $C_{1-8}$ alkyl, a substituted vinyl group, a linear $C_{1-8}$ alkoxy, a branched $C_{1-8}$ alkoxy or cyclic $C_{1-8}$ alkoxy, wherein the fused ring is substituted or unsubstituted and is selected from group consisting of a naphthalene, an isoquinoline, a quinzoline, a benzofuran, an indole, a benzimidazole, a 3,4-dihydro-1H-indene, and a 3,4,dihydro-2H-chromene, wherein the fused ring may be substituted by one or more halogen atoms, selected from the group consisting of fluorine, chlorine, bromine, and iodine, a cyano group, an acetylene group, a propylene group, a vinyl group, a linear $C_{1-8}$ alkyl, a branched $C_{1-8}$ alkyl, a cyclic $C_{1-8}$ alkyl, a substituted vinyl group, a linear $C_{1-8}$ alkoxy, a branched $C_{1-8}$ alkoxy or a cyclic $C_{1-8}$ alkoxy.

9. The method according to claim 7, wherein the acyl chloride is one of the following compounds:

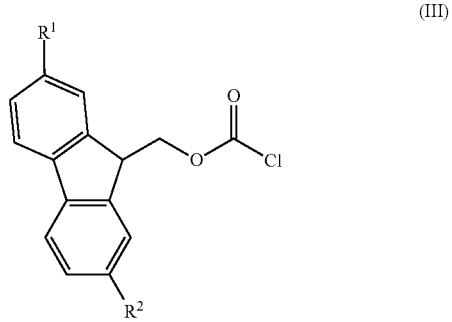

(III)

wherein $R^1$ and $R^2$ are each independently, H, fluorine, chlorine, bromine, iodine, a cyano group, an acetylene group, a propylene group, a vinyl group, a linear $C_{1-8}$ alkyl, a branched $C_{1-8}$ alkyl, a cyclic $C_{1-8}$ alkyl, a substituted vinyl group, a linear $C_{1-8}$ alkoxy, a branched $C_{1-8}$ alkoxy or cyclic $C_{1-8}$ alkoxy.

10. The method according to claim 9, wherein the acyl chloride is one of the following compounds:

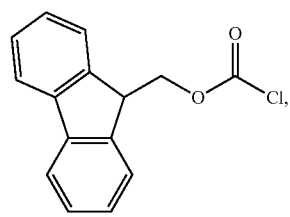

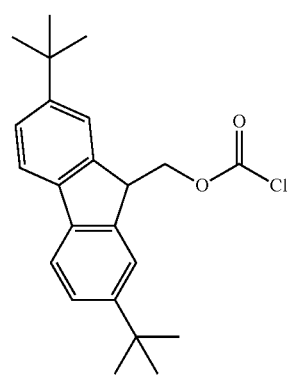

or

-continued

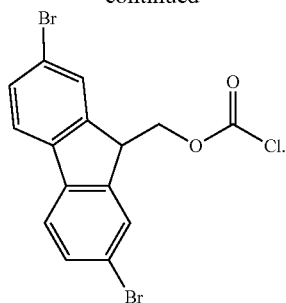

11. The method according to claim 6, wherein the acyl chloride is a compound of Formula VII:

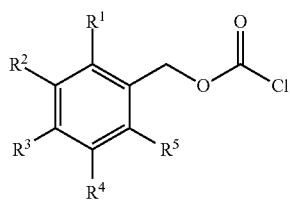

(VII)

wherein $R^1$, $R^2$, $R^3$, $R^4$, and $R^5$ are each independently H, a halogen atom such as a fluorine, or a chlorine, or a bromine, or an iodine, a cyano group, an acetylene group, a propylene group, a vinyl group, a linear $C_{1-8}$ alkyl, a branched $C_{1-8}$ alkyl, a cyclic $C_{1-8}$ alkyl, a substituted vinyl group, a linear $C_{1-8}$ alkoxy, a branched $C_{1-8}$ alkoxy or cyclic $C_{1-8}$ alkoxy.

12. The method according to claim 11, wherein the acyl chloride is one of the following compounds:

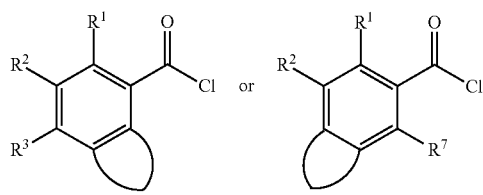

wherein the fused ring system may be an all carbocyclic or a heterocyclic aromatic system, having a 5-7 membered fused ring, or a nonaromatic carbocyclic, or heterocyclic fused ring system such as 3,4-dihydro-1H-indene, or a 3,4,dihydro-2H-chromene, or having a 4-8 membered fused ring, and wherein the fused ring may be substituted with one or more of a halogen atom, a cyano group, an acetylene group, a propylene group, a vinyl group, a linear $C_{1-8}$ alkyl, a branched $C_{1-8}$ alkyl, a cyclic $C_{1-8}$ alkyl, a substituted vinyl group, a linear $C_{1-8}$ alkoxy, a branched $C_{1-8}$ alkoxy or cyclic $C_{1-8}$ alkoxy.

13. The method according to claim 11, wherein the acyl chloride is the following compound:

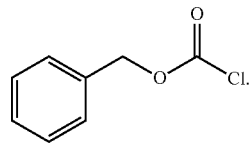 [SMILES: O=C(Cl)OCc1ccccc1]

14. The method according to claim 6, wherein the acyl chloride is a compound of Formula VIII:

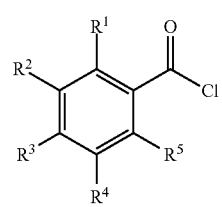

(VIII)

wherein $R^1$, $R^2$, $R^3$, $R^4$, and $R^5$ are each independently H, a halogen atom, such as, fluorine, or a chlorine, or a bromine, or an iodine, a cyano group, an acetylene group, a propylene group, a vinyl group, a linear $C_{1-8}$ alkyl, a branched $C_{1-8}$ alkyl, a cyclic $C_{1-8}$ alkyl, a substituted vinyl group, a linear $C_{1-8}$ alkoxy, a branched $C_{1-8}$ alkoxy or cyclic $C_{1-8}$ alkoxy.

15. The method according to claim 14, wherein the acyl chloride is one of the following compounds:

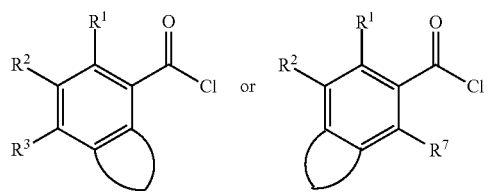

wherein the fused ring system may be an all carbocyclic or a heterocyclic aromatic system, having a 5-7 membered fused ring, or a nonaromatic carbocyclic, or heterocyclic fused ring system such as 3,4-dihydro-1H-indene, or a 3,4,dihydro-2H-chromene, or having a 4-8 membered fused ring, and wherein the fused ring may be substituted with one or more of a halogen atom, a cyano group, an acetylene group, a propylene group, a vinyl group, a linear $C_{1-8}$ alkyl, a branched $C_{1-8}$ alkyl, a cyclic $C_{1-8}$ alkyl, a substituted vinyl group, a linear $C_{1-8}$ alkoxy, a branched $C_{1-8}$ alkoxy or cyclic $C_{1-8}$ alkoxy.

16. The method according to claim 14, wherein the acyl chloride is the following compound:

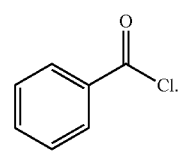

17. The method according to claim 1, wherein the derivatizing agent is a compound of Formula IX:

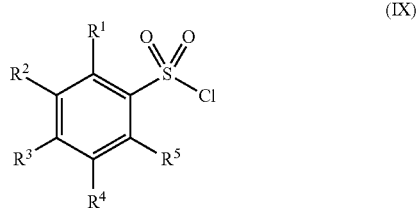
(IX)

wherein $R^1$, $R^2$, $R^3$, $R^4$, and $R^5$ are each independently, a hydrogen, a halogen atom, such as fluorine, chlorine, bromine, or iodine, a cyano group, an acetylene group, a propylene group, a vinyl group, a linear $C_{1-8}$ alkyl, a branched $C_{1-8}$ alkyl, a cyclic $C_{1-8}$ alkyl, a substituted vinyl group, a linear $C_{1-8}$ alkoxy, a branched $C_{1-8}$ alkoxy or cyclic $C_{1-8}$ alkoxy.

18. The method according to claim 17, wherein the derivatizing agent is one of the following compounds:

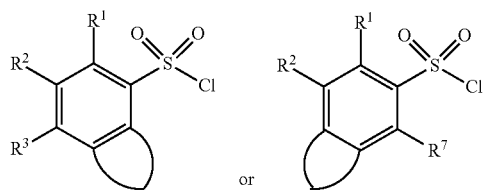

wherein the fused ring system may be an all carbocyclic or a heterocyclic aromatic system, such as a naphthalene, a quinolone, an isoquinoline, a quinzoline, a benzofuran, an indole, or a benzimidazole, having a 5-7 membered fused ring, or a nonaromatic carbocyclic, or heterocyclic fused ring system such as 3,4-dihydro-1H-indene, 3,4,dihydro-2H-chromene, having a 4-8 membered fused ring, and wherein the fused ring may be substituted by one or more of a halogen atoms, such as fluorine, chlorine, bromine, iodine, a cyano group, an acetylene group, a propylene group, a vinyl group, a linear $C_{1-8}$ alkyl, a branched $C_{1-8}$ alkyl, a cyclic $C_{1-8}$ alkyl, a substituted vinyl group, a linear $C_{1-8}$ alkoxy, a branched $C_{1-8}$ alkoxy or cyclic $C_{1-8}$ alkoxy.

19. The method according to claim 1, wherein the mass spectrometry comprises a tandem mass spectrometry technique or a LC-MS/MS technique.

20. The method according to claim 1, wherein the detection of the one or more analytes is qualitative or quantitative.

* * * * *